(12) United States Patent
Zhang et al.

(10) Patent No.: US 12,024,480 B2
(45) Date of Patent: Jul. 2, 2024

(54) POLYNITROSO COMPOUND, ITS PREPARATION AND ELECTROCHEMICAL USE

(71) Applicant: City University of Hong Kong, Kowloon (HK)

(72) Inventors: Qichun Zhang, Ma On Shan (HK); Chun-Sing Lee, Kowloon (HK); Fangyuan Kang, Yau Tsim Mong (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 18/059,516

(22) Filed: Nov. 29, 2022

(65) Prior Publication Data

US 2024/0182403 A1 Jun. 6, 2024

(51) Int. Cl.
| | |
|---|---|
| C07C 207/00 | (2006.01) |
| C07C 205/06 | (2006.01) |
| C07D 487/22 | (2006.01) |
| C07F 1/08 | (2006.01) |
| C07D 205/06 | (2006.01) |

(52) U.S. Cl.
CPC .......... *C07C 207/00* (2013.01); *C07C 205/06* (2013.01); *C07D 487/22* (2013.01); *C07F 1/08* (2013.01)

(58) Field of Classification Search
None
See application file for complete search history.

(56) References Cited

FOREIGN PATENT DOCUMENTS

| | | | |
|---|---|---|---|
| CN | 103779568 B | 5/2014 | |
| CN | 112928267 A | 6/2021 | |
| EP | 3203557 A1 | 8/2017 | |
| WO | 2018070941 A1 | 4/2018 | |

OTHER PUBLICATIONS

Šutalo, P., Pisačić, M., Biljan, I. & Kodrin, I. Benzene and triazine-based porous organic polymers with azo, azoxy and azodioxy linkages: a computational study. CrystEngComm, doi:10.1039/d2ce00186a (2022).
Matasovic, L. et al. Modulating electronic properties of dinitrosoarene polymers. Journal of Materials Chemistry C 10, 5433-5446, doi:10.1039/d2tc00760f (2022).
Wang, P. G. et al. Nitric Oxide Donors: Chemical Activities and Biological Applications. Chemical Reviews 102, 1091-1134, doi:10.1021/cr000040l (2002).
Lee, J., Chen, L., West, A. H. & Richter-Addo, G. B. Interactions of Organic Nitroso Compounds with Metals. Chemical Reviews 102, 1019-1066, doi:10.1021/cr0000731 (2002).
Kostin, G. A., Nikiforov, Y. A. & Kuratieva, N. V. Synthesis and Structure of Ruthenium Nitroso Complexes with Nitrate Anions and Pyridine as Ligands. Journal of Structural Chemistry 61, 86-94, doi:10.1134/s0022476620010096 (2020).
Chen, Z. et al. A nitroaromatic cathode with an ultrahigh energy density based on six-electron reaction per nitro group for lithium batteries. Proceedings of the National Academy of Sciences 119, doi:10.1073/pnas.2116775119 (2022).
Armstrong, A. R. & Bruce, P. G. Synthesis of layered LiMnO2 as an electrode for rechargeable lithium batteries. Nature 381, 499-500, doi:10.1038/381499a0 (1996).
Lin, F. et al. Metal segregation in hierarchically structured cathode materials for high-energy lithium batteries. Nature Energy 1, doi:10.1038/nenergy.2015.4 (2016).
Yan, P. et al. Tailoring grain boundary structures and chemistry of Ni-rich layered cathodes for enhanced cycle stability of lithium-ion batteries. Nature Energy 3, 600-605, doi:10.1038/s41560-018-0191-3 (2018).
Hong, Y.-S. et al. Hierarchical Defect Engineering for LiCoO2 through Low-Solubility Trace Element Doping. Chem 6, 2759-2769, doi:10.1016/j.chempr.2020.07.017 (2020).
Zhu, X. et al. LiMnO2 cathode stabilized by interfacial orbital ordering for sustainable lithium-ion batteries. Nature Sustainability 4, 392-401, doi:10.1038/s41893-020-00660-9 (2020).
Kohlmeyer, C., Klüppel, M. & Hilt, G. Synthesis of Nitrosobenzene Derivatives via Nitrosodesilylation Reaction. The Journal of Organic Chemistry 83, 3915-3920, doi: 10.1021/acs.joc.8b00262 (2018).
Deumal, M., Vela, S., Fumanal, M., Ribas-Arino, J. & Novoa, J. J. Insights into the magnetism and phase transitions of organic radical-based materials. Journal of Materials Chemistry C 9, 10624-10646, doi: 10.1039/d1tc01376a (2021).
Reva, I., Lapinski, L., Chattopadhyay, N. & Fausto, R. Vibrational spectrum and molecular structure of triphenylamine monomer: A combined matrix-isolation FTIR and theoretical study. Phys. Chem. Chem. Phys. 5, 3844-3850, doi:10.1039/b306489a (2003).
Talberg, H. J., Schäffer, C. E., Maki, A., Pohjonen, M.-L. & Koskikallio, J. The Crystal and Molecular Structure of the Monomeric C-Nitroso Compound N,N,N',N' Tetramethyl-1,5-diamino-4-nitrosobenzene. Acta Chemica Scandinavica 30a, 829-834, doi: 10.3891/acta.chem.scand.30a-0829 (1976).
Dhaneshwar, N. N., Naik, S. N. & Tavale, S. S. Structure of 4-nitrosodiphenylamine. Acta Crystallographica Section C Crystal Structure Communications 47, 217-218, doi: 10.1107/s0108270190006564 (1991).
Lewinski, K., Nitek, W. & Milart, P. Molecular complex of 2-[4-(dimethylamino)phenylimino]-3-oxo-N-phenylbutanamide and N,N-dimethyl-4-nitrosoaniline. Acta Crystallographica Section C Crystal Structure Communications 49, 188-190, doi:10.1107/s0108270192010461 (1993).

(Continued)

*Primary Examiner* — Joseph R Kosack
(74) *Attorney, Agent, or Firm* — Renner, Kenner, Greive, Bobak, Taylor & Weber

(57) ABSTRACT

A polynitroso compound including a monocyclic core or a polycyclic core attached with two or more of terminal nitroso groups thereon, such as Formula (A) to Formula (D), in particular, Formula (VII). A method for preparing the polynitroso compound of the present invention. An energy storage device with a cathode including the polynitroso compound of the present invention. Also an electrode material for an energy storage device including a polynitroso compound having a monocyclic core with at least one terminal nitroso group, such as Formula (A) to Formula (D), in particular, Formula (VII).

16 Claims, 45 Drawing Sheets

(56) References Cited

OTHER PUBLICATIONS

Wang, J., Liu, K., Ma, L. & Zhan, X. Triarylamine: Versatile Platform for Organic, Dye-Sensitized, and Perovskite Solar Cells. Chemical Reviews 116, 14675-14725, doi:10.1021/acs.chemrev. 6b00432 (2016).

Ishikawa, M., Kawai, M. & Ohsawa, Y. Synthesis and properties of electrically conducting polytriphenylamines. Synthetic Metals 40, 231-238, doi:10.1016/0379-6779(91)91778-9 (1991).

Smith, P. & Robertson, J. S. Electron paramagnetic resonance study of the reactions of the spin trap 3, 5-dibromo-4-nitrosobenzenesulfonate. Canadian Journal of Chemistry 66, 3190-3190, doi:10.1139/v88-493 (1988).

Chatgilialoglu, C. & Ingold, K. U. "Spontaneous" formation of radicals from nitroso compounds. Inadvertent photolysis vs. molecule assisted homolysis. Journal of the American Chemical Society 103, 4833-4837, doi:10.1021/ja00406a027 (2002).

Yuen, J. D. et al. Importance of Unpaired Electrons in Organic Electronics. J Polym Sci Pol Chem 53, 287-293 (2015).

Hattori, Y., Kusamoto, T. & Nishihara, H. Luminescence, Stability, and Proton Response of an Open-Shell (3,5-Dichloro-4-pyridyl)bis(2,4,6-trichlorophenyl)methyl Radical. Angewandte Chemie International Edition 53, 11845-11848, doi:10.1002/anie. 201407362 (2014).

Hattori, Y., Kusamoto, T. & Nishihara, H. Enhanced Luminescent Properties of an Open-Shell (3,5-Dichloro-4-pyridyl) bis(2,4,6-trichlorophenyl)methyl Radical by Coordination to Gold. Angewandte Chemie International Edition 54, 3731-3734, doi:10.1002/anie. 201411572 (2015).

Jiang, Q. et al. Room-Temperature Ferromagnetism in Perylene Diimide Organic Semiconductor. Advanced Materials 34, doi:10. 1002/adma.202108103 (2022).

Chen, Z. et al. Evolution of the electronic structure in open-shell donor-acceptor organic semiconductors. Nature Communications 12, doi:10.1038/s41467-021-26173-3 (2021).

Kye, H., Kang, Y., Jang, D., Kwon, J. E. & Kim, B.-G. p-Type Redox-Active Organic Electrode Materials for Next-Generation Rechargeable Batteries. Advanced Energy and Sustainability Research, doi:10.1002/aesr.202200030 (2022).

Su, C., Yang, F., Ji, L., Xu, L. & Zhang, C. Polytriphenylamine derivative with high free radical density as the novel organic cathode for lithium ion batteries. J. Mater. Chem. A 2, 20083-20088, doi:10.1039/c4ta03413a (2014).

Wu, M. et al. Chemical Design for Both Molecular and Morphology Optimization toward High-Performance Lithium-Ion Batteries Cathode Material Based on Covalent Organic Framework. Advanced Functional Materials 32, doi:10.1002/adfm.202107703 (2021).

"Li Q, Yu X, Li H. Batteries: From China's 13th to 14th Five-Year Plan. eTransportation, 2022, 14: 100201.Chen, et al., "A nitroaromatic cathode with an ultrahigh energy density based on six-electron reaction per nitro group for lithium batteries", PNAS, 2022, 119(6): e2116775119".

Grey C P, Hall D S. Prospects for lithium-ion batteries and beyond—a 2030 vision. Nature Communications, 2020, 11(1): 1-4.

Kim T, Song W, Son D Y, et al. Lithium-ion batteries: outlook on present, future, and hybridized technologies. Journal of materials chemistry A, 2019, 7(7): 2942-2964.

Li X. Lithium Ions Batteries Electrodes Materials, Design, Outlook and Future Perspectives//MATEC Web of Conferences. EDP Sciences, 2021, 353: 01022.

Banerjee A, Khossossi N, Luo W, et al. Promise and reality of organic electrodes from materials design and charge storage perspective. Journal of Materials Chemistry A, 2022.

Vereshchagin A A, Kalnin A Y, Volkov A I, et al. Key Features of TEMPO-Containing Polymers for Energy Storage and Catalytic Systems[J]. Energies, 2022, 15(7): 2699.

Huang W, Liu S, Li C, et al. Calix [8] quinone: A new promising macrocyclic molecule as an efficient organic cathode in lithium-ion batteries with a highly-concentrated electrolyte. EcoMat, 2022: e12214.

Lu Y, Hou X, Miao L, et al. Cyclohexanehexone with ultrahigh capacity as cathode materials for lithium-ion batteries[J]. Angewandte Chemie, 2019, 131(21): 7094-7098.

Lik A, Fritze L, Müller L, et al. Catalytic B-C coupling by Si/B exchange: A versatile route to π-conjugated organoborane molecules, oligomers, and polymers[J]. Journal of the American Chemical Society, 2017, 139(16):5692-5695.

Li Y, Rajasree SS, Lee GY, Yu J, Tang J-H, Ni R, et al. Anthracene-Triphenylamine-Based Platinum(II) Metallacages as Synthetic Light-Harvesting Assembly. Journal of the American Chemical Society. 2021;143(7):2908-19.

Sickinger A, Mecking S. Origin of the Anisotropy and Structure of Ellipsoidal Poly(fluorene) Nanoparticles. Macromolecules. 2021;54(11):5267-77.

Chen P, Lalancette RA, Jäkle F. π-Expanded Borazine: An Ambipolar Conjugated B-π-N Macrocycle. Angewandte Chemie International Edition. 2012;51(32):7994-8.

Z. Chen, H. Su, P. Sun, P. Bai, J. Yang, M. Li, Y. Deng, Y. Liu, Y. Geng and Y. Xu, Proceedings of the National Academy of Sciences, 2022, 119.

C. Kohlmeyer, M. Klüppel and G. Hilt, The Journal of Organic Chemistry, 2018, 83, 3915-3920.

B. P. Dash, R. Satapathy, E. R. Gaillard, J. A. Maguire and N. S. Hosmane, Journal of the American Chemical Society, 2010, 132, 6578-6587.

H. Kye, Y. Kang, D. Jang, J. E. Kwon and B.-G. Kim, Advanced Energy and Sustainability Research, 2022, DOI:10.1002/aesr. 202200030.

Lu, Y. & Chen, J. Prospects of organic electrode materials for practical lithium batteries. Nature Reviews Chemistry 4, 127-142, doi:10.1038/s41570-020-0160-9 (2020).

Mauger, A., Julien, C., Paolella, A., Armand, M. & Zaghib, K. Recent Progress on Organic Electrodes Materials for Rechargeable Batteries and Supercapacitors. Materials 12, doi:10.3390/ma12111770 (2019).

Xie, J. & Zhang, Q. Recent progress in rechargeable lithium batteries with organic materials as promising electrodes. Journal of Materials Chemistry A 4, 7091-7106, doi:10.1039/c6ta01069e (2016).

Sun, T., Xie, J., Guo, W., Li, D. S. & Zhang, Q. Covalent-Organic Frameworks: Advanced Organic Electrode Materials for Rechargeable Batteries. Advanced Energy Materials 10, doi:10.1002/aenm. 201904199 (2020).

Lyu, H., Sun, X.-G. & Dai, S. Organic Cathode Materials for Lithium-Ion Batteries: Past, Present, and Future. Advanced Energy and Sustainability Research 2, doi:10.1002/aesr.202000044 (2020).

Suga, T., Sugita, S., Ohshiro, H., Oyaizu, K. & Nishide, H. p- and n-Type Bipolar Redox-Active Radical Polymer: Toward Totally Organic Polymer-Based Rechargeable Devices with Variable Configuration. Advanced Materials 23, 751-754, doi:10.1002/adma. 201003525 (2011).

Janoschka, T., Hager, M. D. & Schubert, U. S. Powering up the Future: Radical Polymers for Battery Applications. Advanced Materials 24, 6397-6409, doi:10.1002/adma.201203119 (2012).

Friebe, C. & Schubert, U. S. High-Power-Density Organic Radical Batteries. Topics in Current Chemistry 375, doi:10.1007/s41061-017-0103-1 (2017).

Ou, Y., Xiong, Y., Hu, Z., Zhang, Y. & Dong, L. Emerging conjugated radical polymer cathodes with ultra-long cycle life for an entire polymer rechargeable battery. Journal of Materials Chemistry A 10, 10373-10382, doi:10.1039/d2ta01183b (2022).

Joo, Y., Agarkar, V., Sung, S. H., Savoie, B. M. & Boudouris, B. W. A nonconjugated radical polymer glass with high electrical conductivity. Science 359, 1391-1395, doi:10.1126/science.aao7287 (2018).

Rohland, P. et al. Redox-active polymers: The magic key towards energy storage—a polymer design guideline progress in polymer science. Progress in Polymer Science 125, doi:10.1016/j.progpolymsci. 2021.101474 (2022).

Xie, Y., Zhang, K., Monteiro, M. J. & Jia, Z. Conjugated Nitroxide Radical Polymers: Synthesis and Application in Flexible Energy Storage Devices. ACS Applied Materials & Interfaces 11, 7096-7103, doi:10.1021/acsami.8b21073 (2019).

(56) References Cited

OTHER PUBLICATIONS

Kolek, M. et al. Ultra-high cycling stability of poly(vinylphenothiazine) as a battery cathode material resulting from π-π interactions. Energy & Environmental Science 10, 2334-2341, doi:10.1039/c7ee01473b (2017).

Li, F., Wang, S., Zhang, Y. & Lutkenhaus, J. L. Electrochemical Energy Storage in Poly(dithieno[3,2-b:2',3'-d]pyrrole) Bearing Pendant Nitroxide Radicals. Chemistry of Materials 30, 5169-5174, doi:10.1021/acs.chemmater.8b01775 (2018).

Kim, T. S., Lim, J.-E., Oh, M.-S. & Kim, J.-K. Carbon conductor- and binder-free organic electrode for flexible organic rechargeable batteries with high energy density. Journal of Power Sources 361, 15-20, doi:10.1016/j.powsour.2017.06.059 (2017).

Nishide, H. & Suga, T. Organic Radical Battery. The Electrochemical Society Interface 14, 32-36, doi:10.1149/2.F04054if (2005).

Fletcher, D. A., Gowenlock, B. G. & Orrell, K. G. Structural investigations of C-nitrosobenzenes. Part 1. Solution state 1H NMR studies. Journal of the Chemical Society, Perkin Transactions 2, 2201-2206, doi:10.1039/a703760k (1997).

Gao, Y., Yang, S., Xiao, W., Nie, J. & Hu, X.-Q. Radical chemistry of nitrosoarenes: concepts, synthetic applications and directions. Chemical Communications 56, 13719-13730, doi:10.1039/d0cc06023b (2020).

Bianchi, P. & Monbaliu, J.-C. M. Three decades of unveiling the complex chemistry of C-nitroso species with computational chemistry. Organic Chemistry Frontiers 9, 223-264, doi:10.1039/d1qo01415c (2022).

Yamamoto, H. & Kawasaki, M. Nitroso and Azo Compounds in Modern Organic Synthesis: Late Blooming but Very Rich. Bulletin of the Chemical Society of Japan 80, 595-607, doi:10.1246/bcsj.80.595 (2007).

Deboer, T. J. Spin-Trapping in Early and Some Recent Nitroso Chemistry. Can J Chem 60, 1602-1609 (1982).

Biljan, I. & Vančik, H. Aromatic C-Nitroso Compounds and Their Dimers: A Model for Probing the Reaction Mechanisms in Crystalline Molecular Solids. Crystals 7, doi:10.3390/cryst7120376 (2017).

Klyuchnikov, O. R., Khairutdinov, F. G. & Klyuchnikov, Y. O. Preparation and vulcanizing properties of 1,3,5-trinitrosobenzene. Russ J Appl Chem+ 77, 1382-1385 (2004).

Vančik, H. Aromatic C-nitroso Compounds. (2013).

Beaudoin, D. & Wuest, J. D. Dimerization of Aromatic C-Nitroso Compounds. Chemical Reviews 116, 258-286, doi:10.1021/cr500520s (2016).

Vančik, H. et al. Solid State Photochromism and Thermochromism in Nitroso Monomer-Dimer Equilibrium. The Journal of Physical Chemistry B 106, 1576-1580, doi:10.1021/jp0115289 (2002).

Biljan, I., Kralj, M., Misic Radic, T., Svetlicic, V. & Vancik, H. Dimerization of Nitrosobenzene Derivatives on an Au(111) Surface. J Phys Chem C 115, 20267-20273 (2011).

Gallo, G., Mihanović, A., Rončević, I., Dinnebier, R. & Vančik, H. Crystal structure and ON-OFF polymerization mechanism of poly(1,4-phenyleneazine-N,N-dioxide), a possible wide bandgap semiconductor. Polymer 214, doi:10.1016/j.polymer.2020.123235 (2021).

Greer, M. L., Sarker, H., Mendicino, M. E. & Blackstock, S. C. Azodioxide Radical Cations. Journal of the American Chemical Society 117, 10460-10467 (1995).

Bibulic, P., Roncevic, I., Varga, K., Mihalic, Z. & Vancik, H. Structure and topochemistry of azodioxide oligomers in solid state. Journal of Molecular Structure 1104, 85-90 (2016).

Beaudoin, D., Maris, T. & Wuest, J. D. Constructing monocrystalline covalent organic networks by polymerization. Nature Chemistry 5, 830-834, doi:10.1038/nchem.1730 (2013).

Gowenlock, B. G. & Richter-Addo, G. B. Dinitroso and polynitroso compounds. Chemical Society Reviews 34, doi:10.1039/b500855g (2005).

Li, M. et al. 2D Redox-Active Covalent Organic Frameworks for Supercapacitors: Design, Synthesis, and Challenges. Small 17, doi:10.1002/smll.202005073 (2021).

Bibulic, P., Rončević, I., Špadina, M., Biljan, I. & Vančik, H. Isothermal and Isoconversional Modeling of Solid-State Nitroso Polymerization. The Journal of Physical Chemistry A 124, 10726-10735, doi:10.1021/acs.jpca.0c08382 (2020).

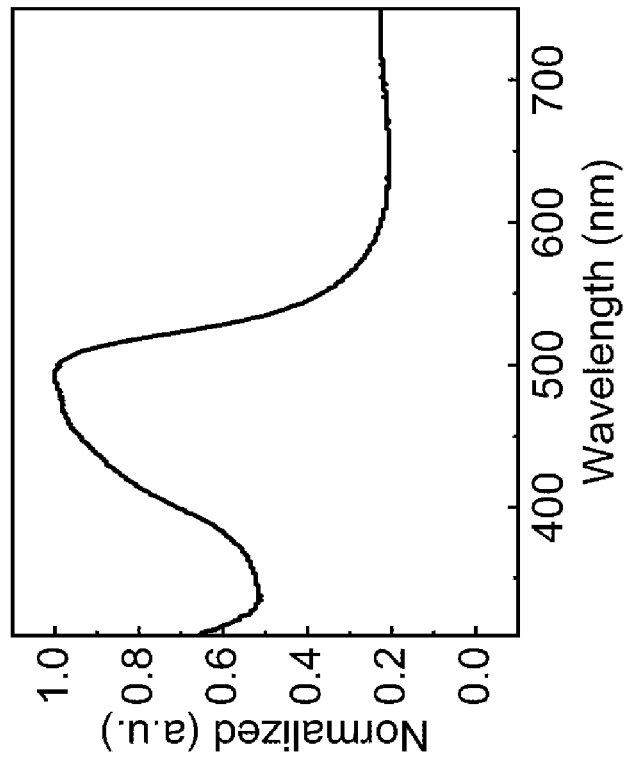
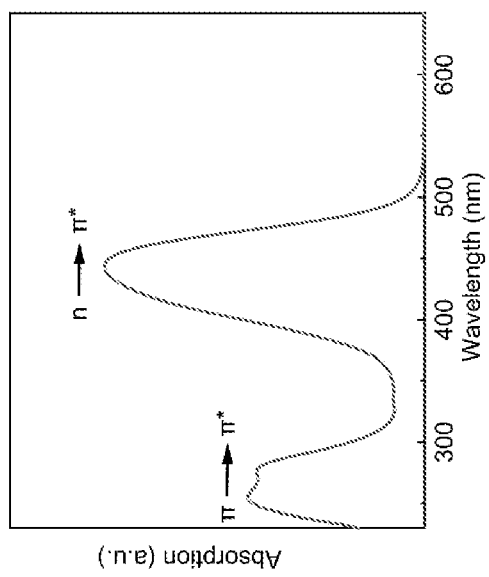
Fig. 21B
Fig. 21A

POLYNITROSO COMPOUND, ITS PREPARATION AND ELECTROCHEMICAL USE

FIELD OF THE INVENTION

The present invention is related to a novel polynitroso compound in particular but not exclusive to a polynitrosoarene compound. The present invention also relates to the preparation of the polynitroso compound as well as the use of it as an electrode material in particular but not exclusive to a cathode material for an energy storage device in particular but not exclusive to a rechargeable lithium-ion battery.

BACKGROUND

Lithium-ion batteries (LIBs) have become one of the most important devices in the energy storage field. However, their performance has been strictly restricted by the limited specific energy capacity (theoretical: <300 mAh g$^{-1}$) and low energy density of the inorganic cathode materials.

Compared with inorganic cathode materials, organic cathode materials are believed to provide high theoretical specific capacities, structural diversity, environmental friendliness, and potentially sustainable production. One of the organic cathode material examples may be the materials made of open-shell radicals such as nitroxide radicals. Although these materials are believed to have robust stability, swift electron-transfer rate, promising reversibility, high redox potential, etc., they often suffer from low intrinsic conductivity and high dissolution in organic electrolytes, rendering them limited rate performance with rapid capacity fading, and therefore seldom being used in direct electrode fabrication.

It has been reported that by tethering the radical motifs onto a conjugated or nonconjugated polymer backbone, it may enhance the electrical conductivity and reduce solubility of the radical motifs. However, with the introduction of polymer backbone, it not only incurs inherent issues such as synthetic complexity and poor processability, but also makes the simple redox energy-storage mechanism elusive. In addition, the redundant polymer moieties would inevitably lead to a tremendous cost towards the theoretical capacity (~only 110-130 mAhg$^{-1}$) resulting in a low energy density and severely hampering their further applications in energy storage devices.

Accordingly, there is a strong need in developing novel radical materials that may act as a standalone electrode material and as a material that may improve the overall performance of the energy storage device, to meet the ever-increasing energy storage demands.

SUMMARY OF THE INVENTION

In a first aspect of the present invention, there is provided a polynitroso compound for use in an energy storage device, comprising a monocyclic core or a polycyclic core attached with two or more of terminal nitroso groups thereon.

In an embodiment, the polynitroso compound comprises a structure having a formula of:

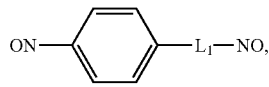

Formula (A)

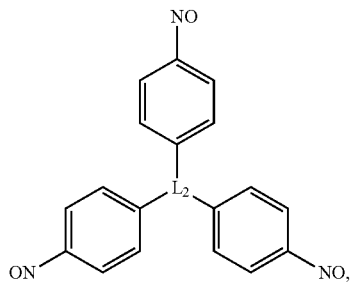

Formula (B)

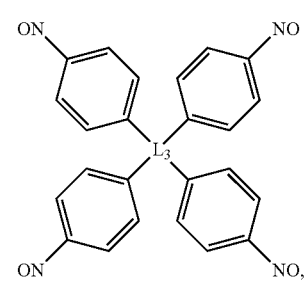

Formula (C)

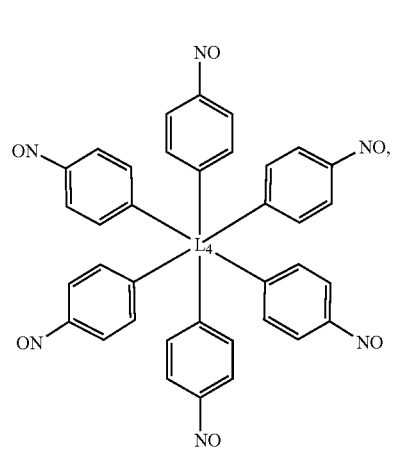

Formula (D)

with $L_1$ to $L_4$ being a linking group, and wherein: $L_1$, if present, is a benzenoid; $L_2$ and $L_3$ are independently selected from an atom, an alkenyl group, a benzenoid, or a macrocycle; and $L_4$ is selected from a benzenoid or a macrocycle.

In an embodiment, wherein $L_1$ comprises

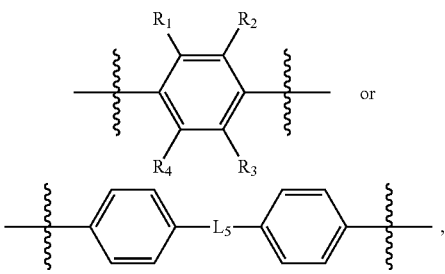

with $R_1$ to $R_4$ being independently selected from a hydrogen atom, an unsubstituted or substituted linear or branched C1-C6 alkyl group, an aryl group, a halogen, and adjacent $R_1$ to $R_4$ may form a fused heterocyclic or carbocyclic ring; and $L_5$, if present, being an unsubstituted or substituted C2-C4 alkenyl group, a heterocyclic or carbocyclic ring.

It is preferred that $R_1$ to $R_4$ are identical and are selected from a hydrogen atom, an unsubstituted linear or branched C1-C6 alkyl group, a halogen and adjacent $R_1$ to $R_4$ may form a fused 6-membered carbocyclic ring; and $L_5$, if present, being a non-fused 6-membered carbocyclic ring or a fused 6-membered carbocyclic ring.

Preferably, the polynitroso compound comprises a structure having a formula of:

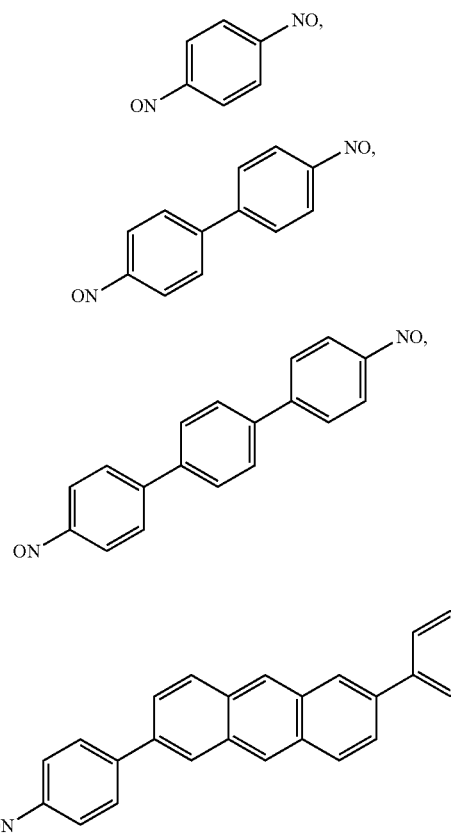

Formula (I)

Formula (II)

Formula (III)

Formula (IV)

Formula (V)

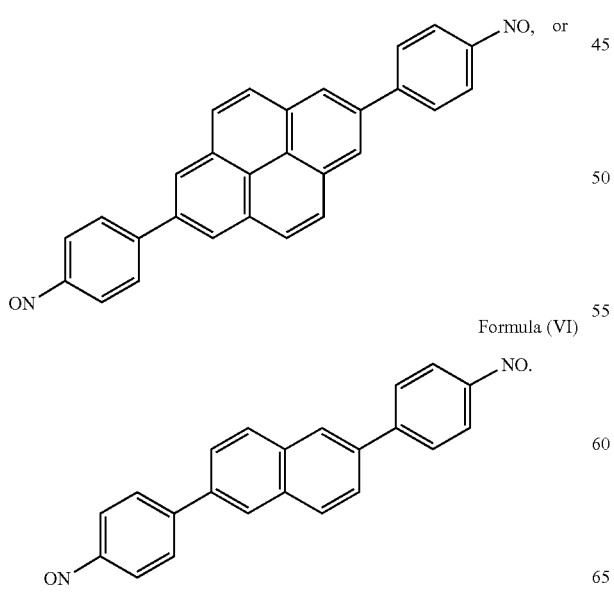

Formula (VI)

In an embodiment, $L_2$ comprises a nitrogen atom, or

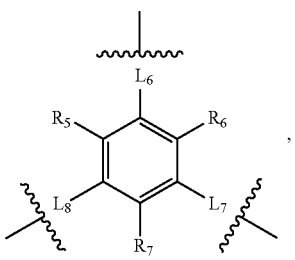

with $R_5$ to $R_7$ being independently selected from a hydrogen atom, an unsubstituted or substituted linear or branched C1-C6 alkyl group, or a halogen; and $L_6$ to $L_8$, if present, being identical and a carbocyclic ring.

It is preferred that $R_5$ to $R_7$ are identical and are selected from a hydrogen atom, an unsubstituted linear or branched C1-C6 alkyl group or a halogen; and $L_6$ to $L_8$, if present, is a 6-membered carbocyclic ring.

Preferably, the polynitroso compound comprises a structure having a formula of:

Formula (VII)

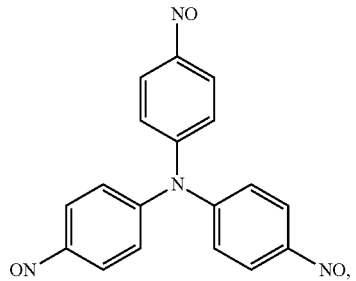

Formula (VIII)

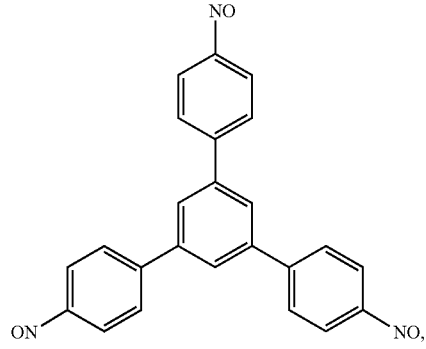

Formula (IX)

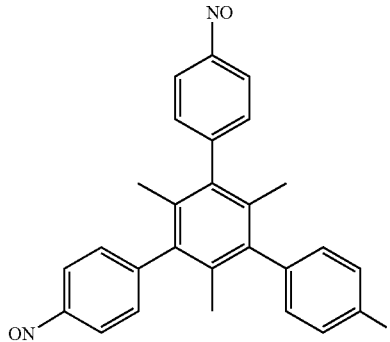

Formula (X)

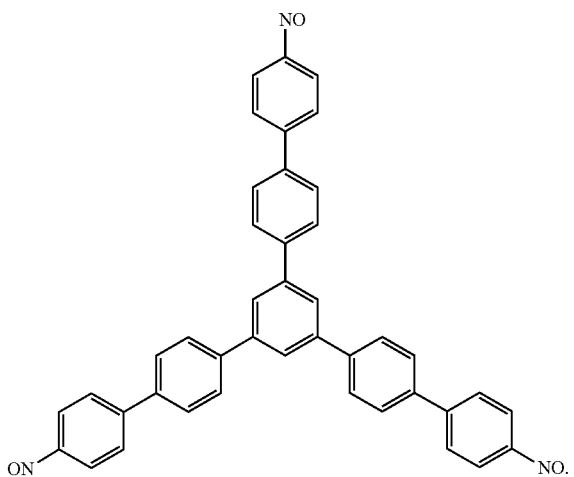

In an embodiment, L₃ comprises a carbon atom, a C2-C4 alkenyl group,

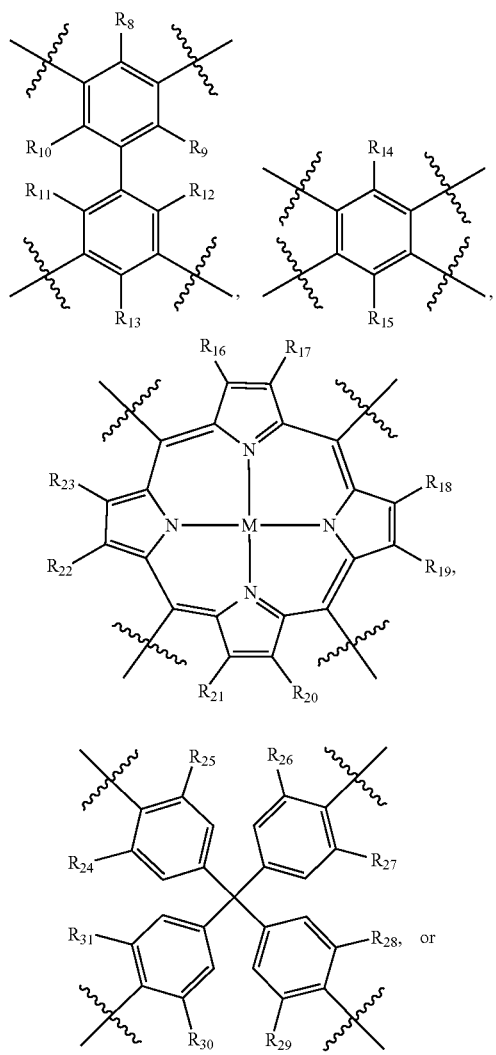

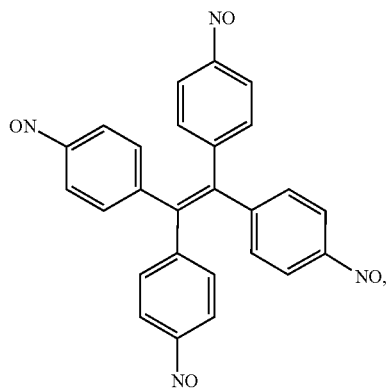

with $R_8$ to $R_{15}$ being independently selected from a hydrogen atom, a halogen or an unsubstituted or substituted linear or branched C1-C6 alkyl group;

$R_{16}$ to $R_{23}$ being independently selected from a hydrogen atom, an unsubstituted or substituted linear or branched C1-C6 alkyl group, an aryl group, a halogen, and adjacent $R_{16}$ to $R_{23}$ may form a fused heterocyclic or carbocyclic ring; M being $H_2$ or a metal atom;

$R_{24}$ to $R_{31}$ being independently selected from a hydrogen atom, a halogen and an unsubstituted or substituted linear or branched C1-C6 alkyl group;

$R_{32}$ to $R_{41}$ being independently selected from a hydrogen atom, an unsubstituted or substituted linear or branched C1-C6 alkyl group, a halogen, and adjacent $R_{32}$ to $R_{41}$ may form a fused heterocyclic or carbocyclic ring.

It is preferred that $R_8$ to $R_{13}$ are identical and are selected from a hydrogen atom, and an unsubstituted linear or branched C1-C6 alkyl group;

$R_{14}$ and $R_{15}$ are identical and are selected from a hydrogen atom, and an unsubstituted linear or branched C1-C6 alkyl group;

$R_{16}$ to $R_{23}$ are identical and are selected from a hydrogen atom, an unsubstituted linear or branched C1-C6 alkyl group, and adjacent $R_{16}$ to $R_{23}$ may form a fused 6-membered carbocyclic ring; M being $H_2$ or a metal atom selected from iron, nickel, copper, zinc or manganese;

$R_{24}$ to $R_{31}$ are identical and are selected from a hydrogen atom, and an unsubstituted linear or branched C1-C6 alkyl group; and $R_{32}$ to $R_{41}$ are identical and are selected from a hydrogen atom, an unsubstituted linear or branched C1-C6 alkyl group, and adjacent $R_{32}$ to $R_{41}$ may form a fused 6-membered carbocyclic ring.

Preferably, the polynitroso compound comprises a structure having a formula of:

Formula (XI)

Formula (XII)
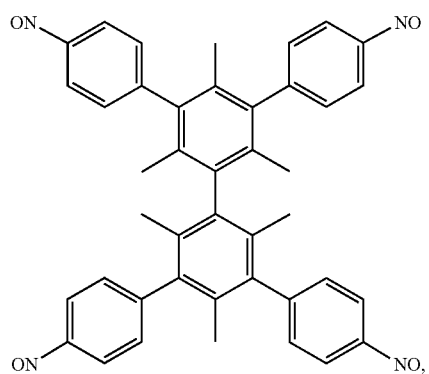
Formula (XIII)
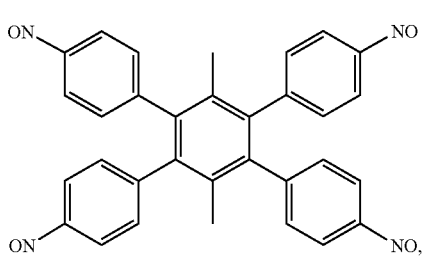
Formula (XIV)
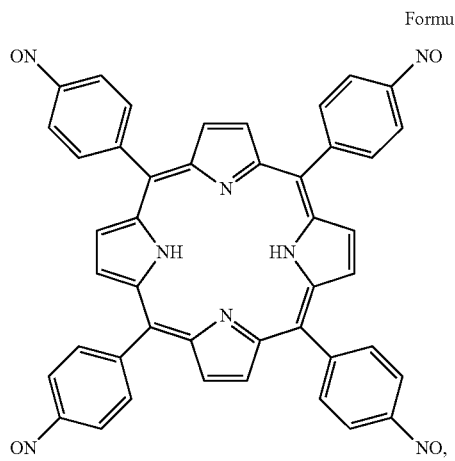
Formula (XV)
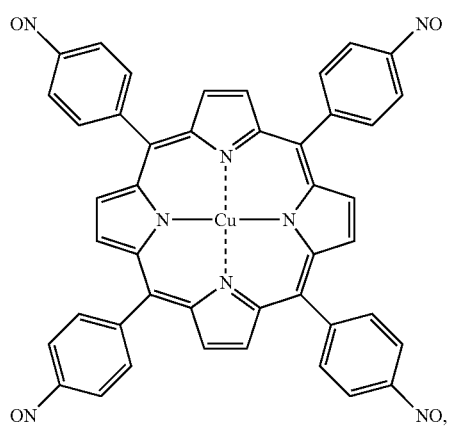
Formula (XVI)
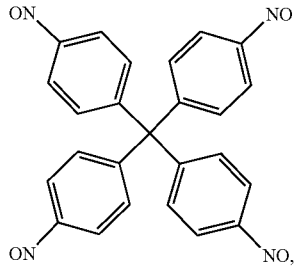
Formula (XVII)
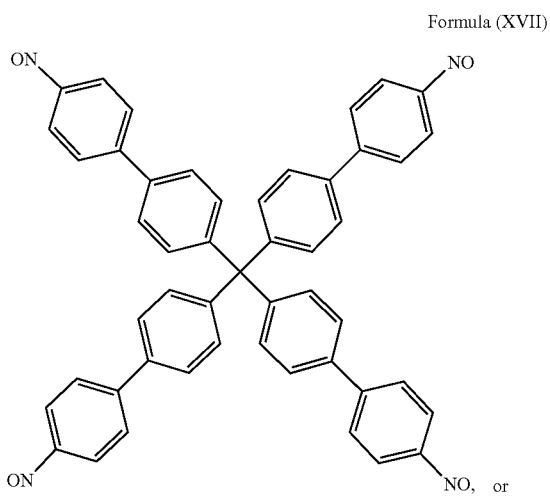
or
Formula (XVIII)
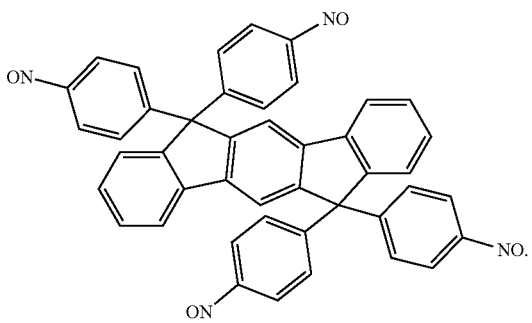
In an embodiment, $L_4$ comprises a 6-membered carbocyclic ring. Preferably, the polynitroso compound comprises a structure having a formula of:

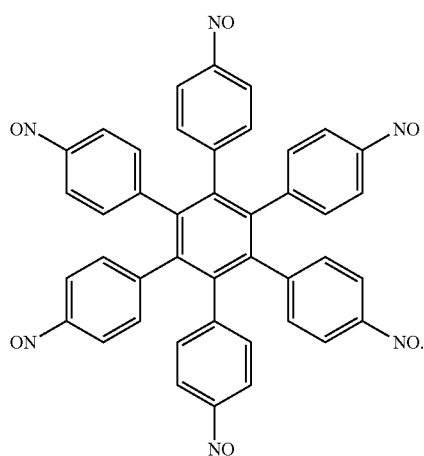

Formula (XIX)

In an embodiment, the polynitroso compound comprises monomeric form, polymeric form, and a combination thereof.

In an embodiment, the polynitroso compound is a compound radical. Preferably, the compound radical remains active for at least 6 months.

In an embodiment, the energy storage device comprises a rechargeable lithium-ion battery.

In a second aspect of the present invention, there is provided a method for preparing the polynitroso compound in accordance with the first aspect of the present invention, comprising the steps of:
a) providing a precursor compound comprising two or more terminal trifluoroborate groups or silyl groups; and
b) conducting nitrosation to the precursor compound with a nitrosating agent.

In an embodiment, the terminal trifluoroborate group comprises trifluoroborate salt.

Preferably, the trifluoroborate salt is potassium trifluoroborate.

In an embodiment, the terminal silyl groups is trimethylsilyl group.

In an embodiment, the nitrosating agent comprises a nitrosonium salt. It is preferred that the nitrosonium salt is selected from the group consisting of nitrosyl bromide, nitrosyl chloride, nitrosylsulfuric acid, posattium nitrite, sodium nitrite, silver nitrite, nitrosonium tetrafluoroborate, and a combination thereof.

In an embodiment, the nitrosation is conducted under a neutral or acidic condition.

It is preferred that the acidic condition is adjusted by hydrochloric acid, hydrobromic acid, sulfuric acid or a combination thereof.

In an embodiment, the precursor compound is provided in form of a reaction solvent mixture.

Preferably, the reaction solvent is selected from the group consisting of 1,2-dichlorobenzene, dichloromethane, 1,2-dichloroethane, tetrahydrofuran, n-hexane, heptane, ethyl acetate, toluene, acetonitrile and a combination thereof.

In an embodiment, the reaction solvent is acetonitrile.

It is preferred that step b) comprises the step of preparing a reaction mixture of the precursor compound and the nitrosating agent at a mole ratio of A:B, where A is from about 2 to about 4, and B is from about 3 to about 10.

The present invention in the third aspect provides an energy storage device with a cathode comprising the polynitroso compound in accordance with the first aspect of the present invention.

In an embodiment, the energy storage device has a stabilized discharge capacity from about 270 mA h g$^{-1}$ to about 117 mA h g$^{-1}$ at a current density from about 50 mA g$^{-1}$ to about 1 A g$^{-1}$ over a voltage window of about 1.3 V to about 4.3 V.

In an embodiment, the energy storage device has a specific capacity of about 300 mA h g$^{-1}$ after 100 charge/discharge cycles under a current density of about 100 mA g$^{-1}$.

In an embodiment, the energy storage device has about 85% capacity retention after about 1000 charge/discharge cycles under a current density of about 1 A g$^{-1}$.

It is preferred that the energy storage device is a rechargeable lithium-ion battery.

According to the fourth aspect of the invention, there is provided an electrode material for an energy storage device comprising a polynitroso compound having a monocyclic core with at least one terminal nitroso group.

It is preferred that the polynitroso compound comprising a structure having a formula of.

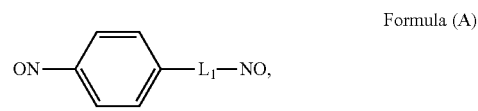

Formula (A)

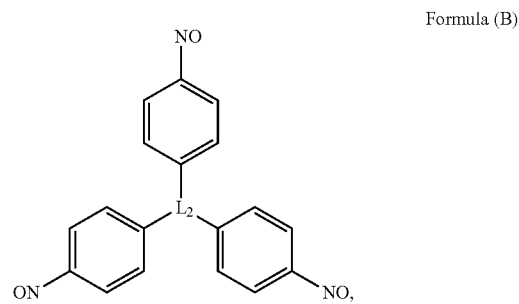

Formula (B)

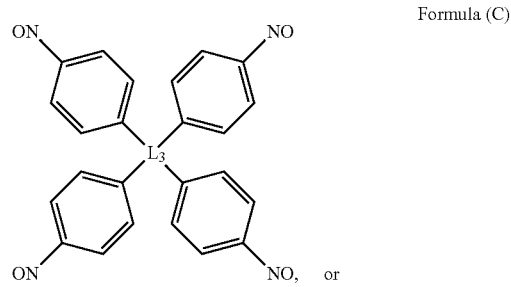

Formula (C)

-continued

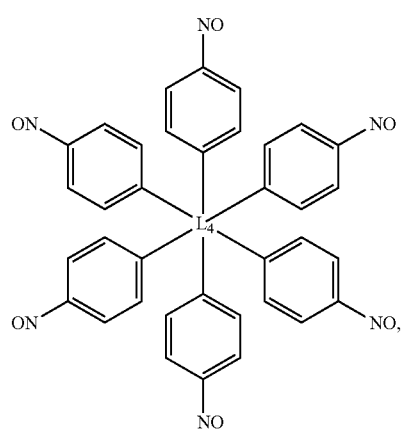

Formula (D)

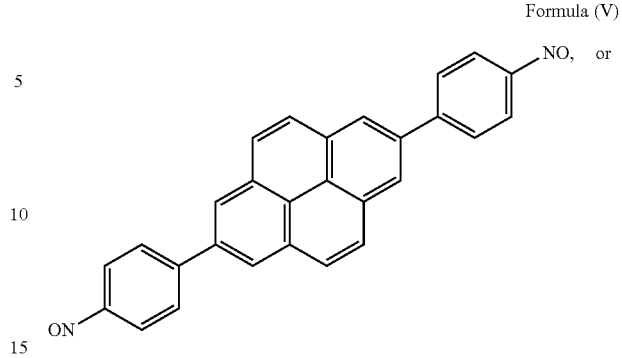

Formula (V)

with L₁ to L₄ being a linking group, and wherein: $L_1$, if present, is a benzenoid; $L_2$ and $L_3$ are independently selected from an atom, an alkenyl group, a benzenoid, or a macrocycle; and $L_4$ is selected from a benzenoid or a macrocycle.

In an embodiment, the polynitroso compound comprises a structure having a formula of:

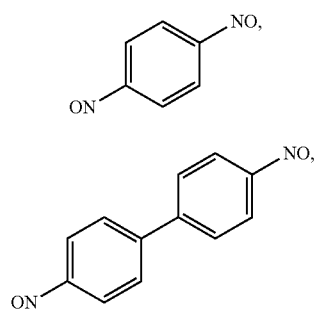

Formula (I)

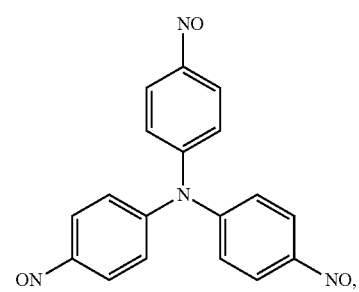

Formula (VI)

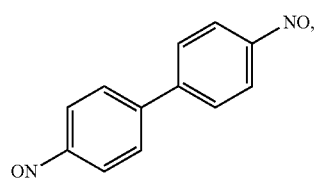

Formula (II)

In an embodiment, the polynitroso compound comprising a structure having a formula of:

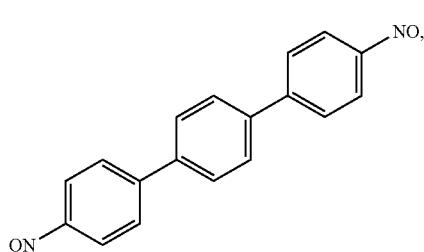

Formula (III)

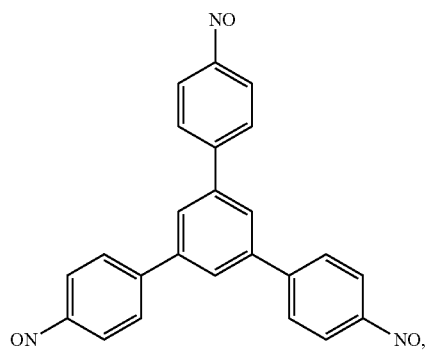

Formula (VII)

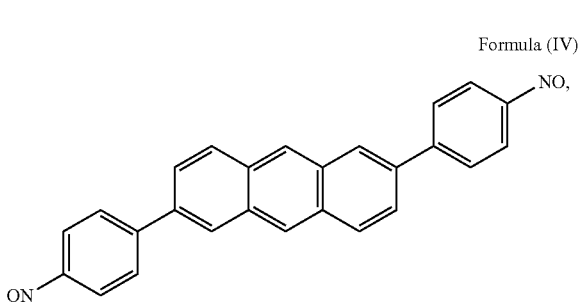

Formula (IV)

Formula (VIII)

Formula (IX)
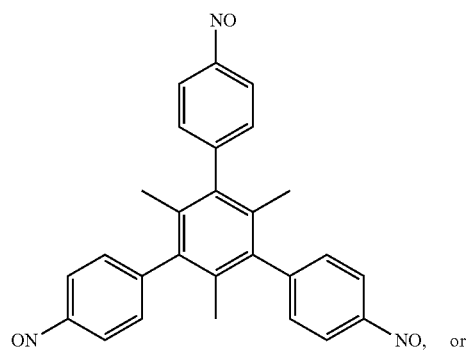
or
Formula (X)
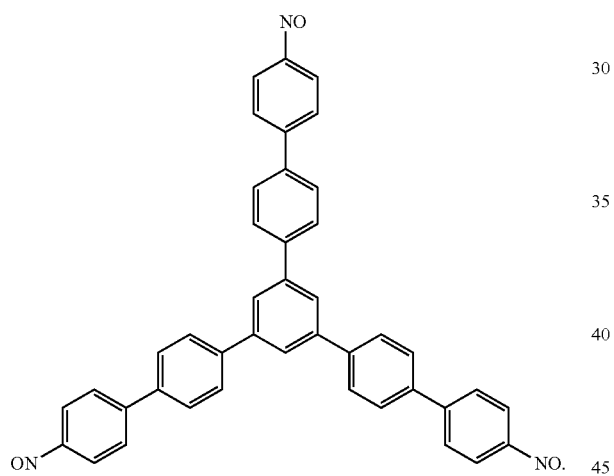
In an embodiment, the polynitroso compound comprises a structure having a formula of:
Formula (XI)
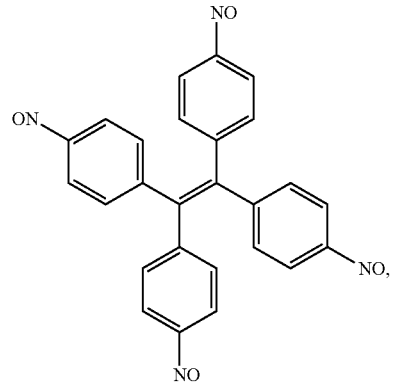
Formula (XII)
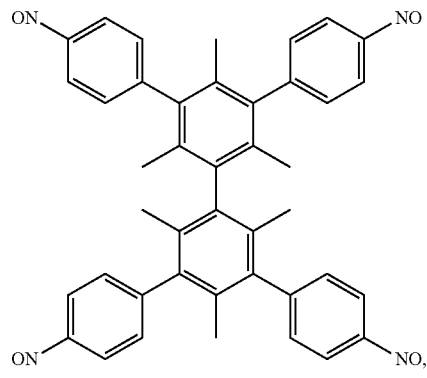
Formula (XIII)
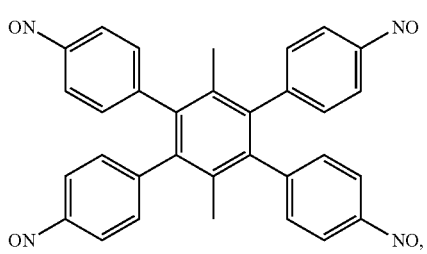
Formula (XIV)
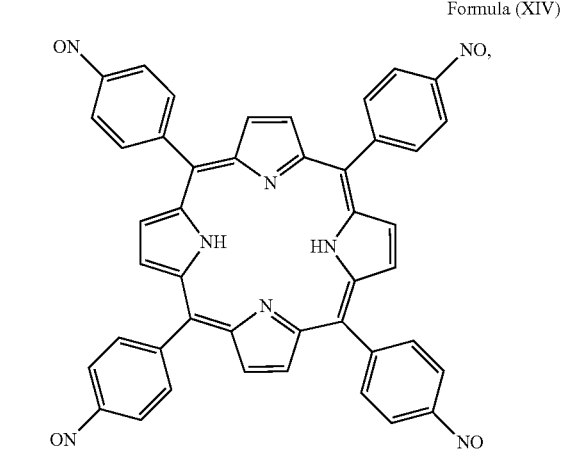
Formula (XV)
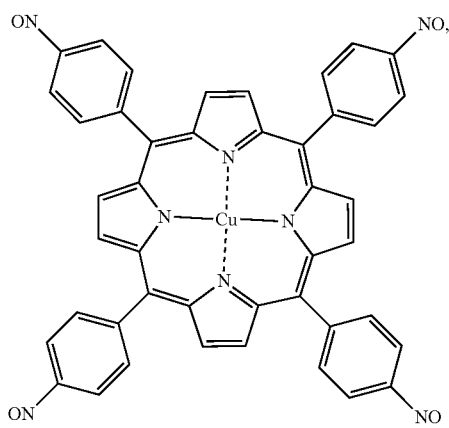

Formula (XVI)

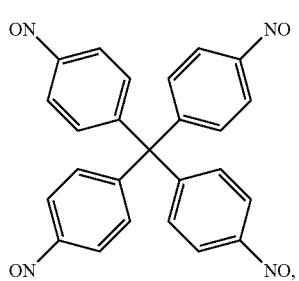

Formula (XVII)

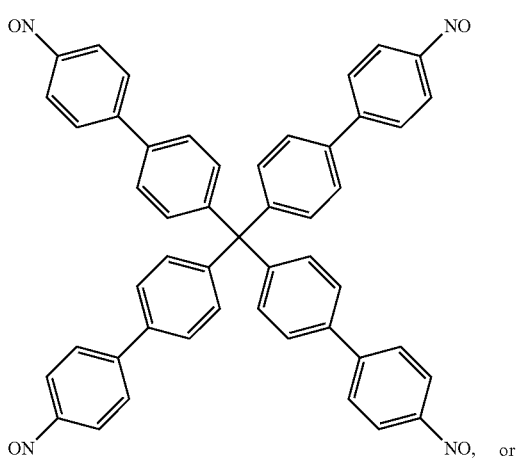

or

Formula (XVIII)

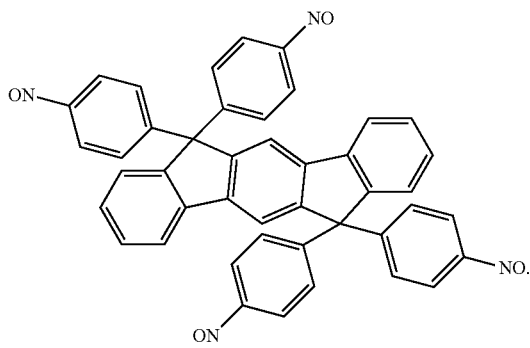

In an embodiment, the polynitroso compound comprises a structure having a formula of Formula (XIX)

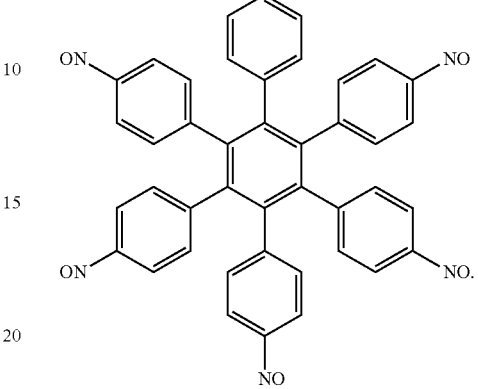

Preferably, the electrode material is a cathode material.

BRIEF DESCRIPTION OF THE DRAWINGS

FIG. 21A is an UV/Vis absorption spectrum of TPA-3NO in chloroform ($10^{-5}$ M).

FIG. 21B is an UV/Vis absorption spectrum of TPA-3NO in film.

DESCRIPTION OF THE PREFERRED EMBODIMENTS

Figure 1:
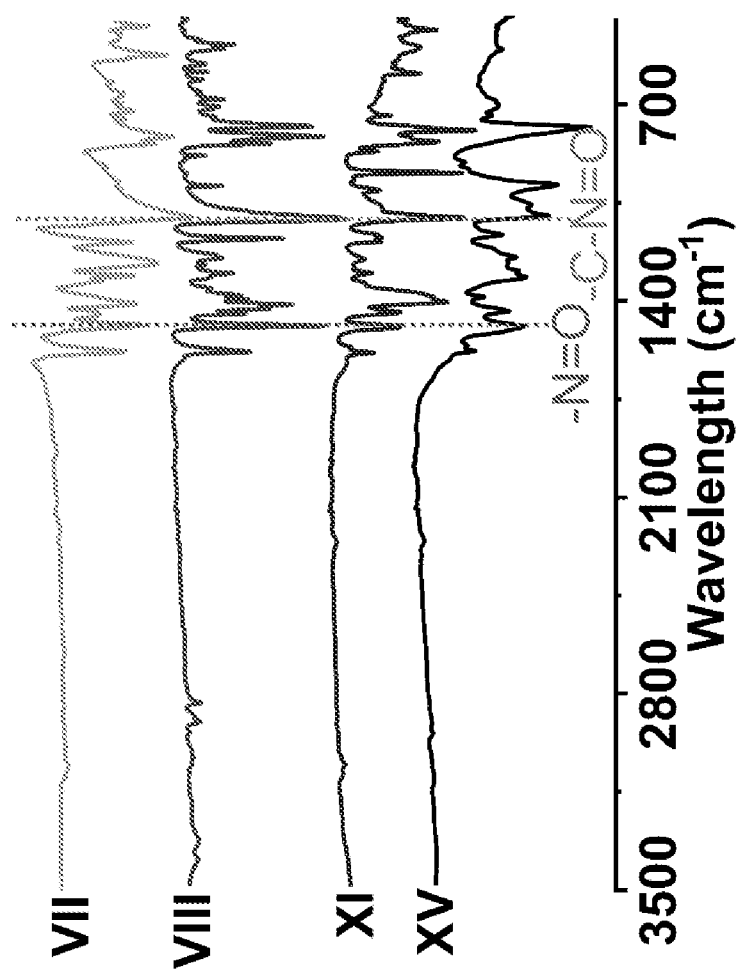
FIG. 1 shows a Fourier-transform infrared (FT-IR) spectra of polynitroso compounds VII, VIII, XI, and XV.

Unless otherwise specifically provided, all tests herein are conducted at standard conditions which include a room and testing temperature of 25° C., sea level (1 atm.) pressure, pH 7, and all measurements are made in metric units. Furthermore, all percentages, ratios, etc. herein are by weight, unless specifically indicated otherwise. It is understood that unless otherwise specifically noted, the materials compounds, chemicals, etc. described herein are typically commodity items and/or industry-standard items available from a variety of suppliers worldwide.

Unless otherwise defined, all technical terms used herein have the same meaning as commonly understood by one skilled in the art to which the invention belongs.

As used herein, the forms "a", "an", and "the" are intended to include the singular and plural forms unless the context clearly indicates otherwise.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

It is believed that nitroso (NO) group can either be oxidized into a nitro group via the 2 e$^-$ process or reduced to amine directly by a 4 e$^-$ process. The multiple electrons transformation processes impart its potential application in LIBs. For example, it is believed that the theoretical specific capacity of one NO group may be as high as about 3573 mAh g$^{-1}$ based on the 4 e$^-$ reduction process. Without intending to be limited by theory, the inventors have, through their own researches, trials, and experiments, devised a class of polynitroso compounds, particularly polynitrosoarenes, that is chemically stable in ambient atmosphere, and is characterized by (open-shell) radical character. In particular, it is unexpectedly found that the radical character of the polynitroso compounds was remained substantially unchanged over a long period of time.

In an example embodiment, the radical character of the polynitroso compounds may remain active for at least 6 months. The polynitroso compounds as described herein thus potentially to be used as an organic radical cathode material for rechargeable batteries such as LIBs, organic radical battery (ORBs), and the like.

According to the invention, there is provided a polynitroso compound for use in an energy storage device, comprising a monocyclic core or a polycyclic core attached with two or more of terminal nitroso groups thereon. As used herein, the term "polynitroso compound" generally denotes an organic compound having at least one or more than one nitroso (NO) group, such as two or more, two to three, two to four, two to five, two to six, two to seven, two to eight nitroso groups and the like. In particular, the polynitroso compound may have two to six nitroso groups. In the embodiments of the present invention, the polynitroso compound may have two, three, four, or six nitroso groups. The nitroso groups are particularly terminal nitroso groups. The phrase "terminal" shall be understood in the art that it describes a chemical functional group, such as the nitroso group as described herein is located/tethered/bonded to/at the end of a carbon chain or at the peripheral of a cyclic ring. In particular, these terminal nitroso groups are attached to (preferably by way of covalent bond) to the monocyclic or polycyclic core.

The monocyclic core may generally refer to a group of atoms being connected to form a single ring structure. The atoms within the monocyclic core may be all being carbon (i.e., carbocyclic core), or being both carbon and non-carbon atoms (i.e., heterocyclic core). The ring size of the monocyclic core may vary from, for example, three to eight, three to seven, three to six, three to five, or three to four. Depending on the ring size, the monocyclic core may also have varying number of saturated and unsaturated bonds (i.e., double bond and triple bond). In particular, the monocyclic core may include unsubstituted or substituted C3-C10 carbocycles, unsubstituted or substituted C2-C5 heterocycles, unsubstituted or substituted macrocycles, monoaromatic hydrocarbons and the like.

The carbocycles may include unsubstituted C3-C10 cycloalkanes, cycloalkenes, cycloalkynes or their derivatives which are substituted with, such as methyl, ethyl, isopropyl, hydroxyl, halogen, phenyl and the like. Examples of unsubstituted C3-C10 cycloalkanes, cycloalkenes, and cycloalkynes may include cyclopropane, cyclobutane, cyclopetane, cyclohexane, cyclopentene, cyclopentadiene, cyclohexene, cyclohexadiene, cyclononyne, cyclodecyne and the like.

The unsubstituted C2-C5 heterocycles may include three-membered rings with one heteroatom, four-membered ring with one or two heteroatom(s), five-membered ring with one to three heteroatom(s), and six-membered ring with one to three heteroatom(s). The heteroatoms may be selected from nitrogen, oxygen, sulphur, and a combination thereof.

Examples may include aziridine, 2H-azirine, oxirane, thiirane, azetidine, oxetane, thietane, pyrrolidine, pyrroline, furan, pyrrole, oxazole, isothiazole, piperidine, pyridine, piperazine, pyrazine, trizaine, dithiane, etc. In an embodiment where the C2-C5 heterocycles are substituted, the substituent(s) may be methyl, ethyl, isopropyl, hydroxyl, halogen, phenyl and the like.

Macrocycles may refer to organic compounds containing a ring with twelve or more atoms. The macrocycles may particularly refer to heterocyclic macrocycles, such as crown ether, calixarenes, porphyrins, cyclodextrins and the like, which may or may not be substituted with one or more of methyl, ethyl, isopropyl, hydroxyl, halogen, phenyl, carboxyl and the like.

Monocyclic aromatic hydrocarbons particularly refer to benzene or its derivatives such as those substituted with one or more of methyl, ethyl, isopropyl, hydroxyl, halogen, amine, and the like. Examples of benzene derivatives may include toluene, ethylbenzene, p-xylene, m-xylene, mesitylene, durene, 2-phenylhexane, phenol, aniline and the like.

The polycyclic core, as used herein, may generally refer a group of single ring structures being connected/bonded together by fusing (i.e., edge-to-edge), tethering, and a combination thereof. In particular, the polycyclic core may include polycyclic cycloalkanes, polycyclic aromatic hydrocarbons, heterocyclic aromatic compounds with multiple rings and the like.

Examples of the polycyclic core may include tricyclohexylamine, triphenylamine, tetracyclohexylmethane, tetraphenylmethane, biphenyl, triphenylbenzene, naphthalene, fluorene, 6,12-dihydroindeno[1,2-b]fluorine, anthracene, phenanthrene, phenalene, tetracene, chrysene, pyrene, triphenyl, tetraphenylethene and the like, or any of the above substituted with one or more of, such as methyl, ethyl, isopropyl, hydroxyl, halogen, amine, phenyl and the like.

In particular embodiments, the polynitroso compound may comprise a structure having a formula of.

Formula (A)

ON—⟨⟩—$L_1$—NO,

Formula (B)

[structure with NO groups and $L_2$ linker]

Formula (C)

[structure with NO groups and $L_3$ linker]

or

Formula (D)

[structure with NO groups and $L_4$ linker]

with $L_1$ to $L_4$ being a linking group, and wherein:
$L_1$, if present, is a benzenoid; $L_2$ and $L_3$ are independently selected from an atom, an alkenyl group, a benzenoid, or a macrocycle; and $L_4$ is selected from a benzenoid or a macrocycle.

The term "benzenoid" generally denotes an organic compound with at least one benzene ring. For example, it may be a benzene, or its derivatives as described herein, or a polycyclic cycloalkanes, polycyclic aromatic hydrocarbons, heterocyclic aromatic compounds with multiple rings as described herein. The atom is preferably the one with its electronic valance being fully occupied after linking the nitrosoarene moieties. For example, referring to Formula (B) and (C), it would be preferred that $L_2$ and $L_3$, to be a nitrogen atom and a carbon atom, respectively. The alkenyl group may be an unsubstituted or substituted C2-C4 alkenyl group, such as an ethenyl, propenyl, butenyl with or without being substituted with methyl, ethyl, isopropyl, hydroxyl, halogen, amine, phenyl and the like. The macrocycle may be the one as described herein.

In an embodiment, $L_1$ may comprise

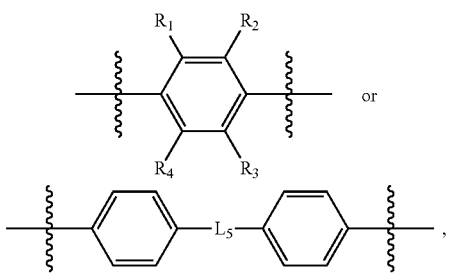

or with $R_1$ to $R_4$ being independently selected from a hydrogen atom, an unsubstituted or substituted linear or branched C1-C6 alkyl group, an aryl group, a halogen, and adjacent $R_1$ to $R_4$ may form a fused heterocyclic or carbocyclic ring; and $L_5$, if present, being an unsubstituted or substituted C2-C4 alkenyl group, a heterocyclic or carbocyclic ring.

In an embodiment where $R_1$ to $R_4$ being an unsubstituted or substituted linear or branched C1-C6 alkyl group, the alkyl group may refer to a linear or branched chain of hydrocarbons having 1 to 6 carbon atoms with or without a substituted with one or more of a halogen such as fluoride, chloride, bromide and iodide, a hydroxyl group, a phenyl group, an amino group, etc. Examples of linear or branched C1-C6 alkyl group may include methyl, ethyl, propyl, butyl, pentyl, hexyl, iso-propyl, isobutyl, sec-butyl, tert-pentyl, 3-pentyl, and the like.

In an embodiment where $R_1$ to $R_4$ being an aryl group, the aryl group may refer to an aromatic hydrocarbon, particularly those derived from benzene such as phenyl, naphthyl, tolyl, xylyl, hydroxyphenyl, halophenyl (i.e., a phenyl group substituted with, such as fluoride, chloride, bromide, or iodide) and the like.

In an embodiment where $R_1$ to $R_4$ being a halogen, it may be and selected from, such as fluoride, chloride, bromide, and iodide. The halogen on $R_1$ to $R_4$, if present, is preferably identical.

In an embodiment, adjacent $R_1$ to $R_4$ may form a fused heterocyclic or carbocyclic ring. That is, for example, $R_1$ and $R_2$ and/or $R_3$ and $R_4$ may form a fused heterocyclic or carbocyclic ring. In particular, the fused heterocyclic ring may be C2-C5 heterocycles as described herein whereas the fused carbocyclic ring may be an unsubstituted C3-C10 cycloalkanes, cycloalkenes, cycloalkynes or their derivatives as described herein or a benzene or its derivatives as described herein.

Preferably, $R_1$ to $R_4$ are identical and are selected from a hydrogen atom, an unsubstituted linear or branched C1-C6 alkyl group, such as an unsubstituted linear or branched C1-C3 alkyl group such as methyl, ethyl, propyl, isopropyl, a halogen as described herein and adjacent $R_1$ to $R_4$ may form a fused 6-membered carbocyclic ring such as benzene or cyclohexane; and $L_5$, if present, being a non-fused 6-membered carbocyclic ring such as a benzene, cyclohexane, cyclohexene, cyclohexa-1,3-diene, cyclohexa-1,4-diene, or a fused 6-membered carbocyclic ring such as naphthalene, anthracene, phenanthrene, phenalene, tetracene, chrysene, pyrene and the like.

As specific embodiments, the polynitroso compound having a structure of Formula (A) may comprise a structure having a formula of:

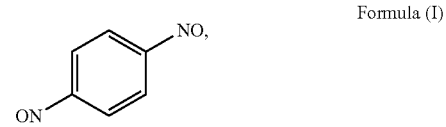

Formula (I)

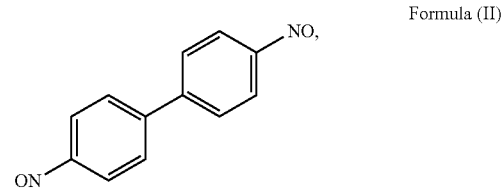

Formula (II)

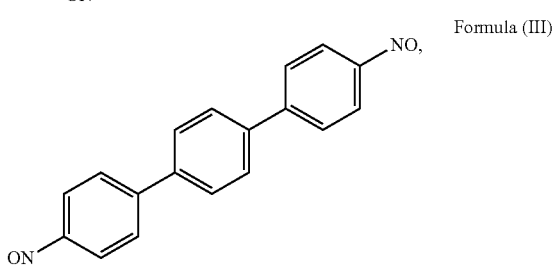

Formula (III)

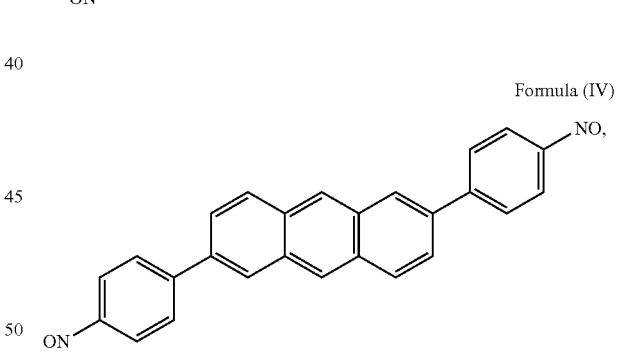

Formula (IV)

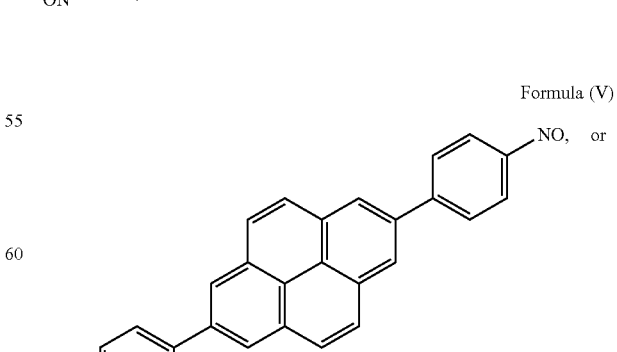

Formula (V)

Formula (VI)

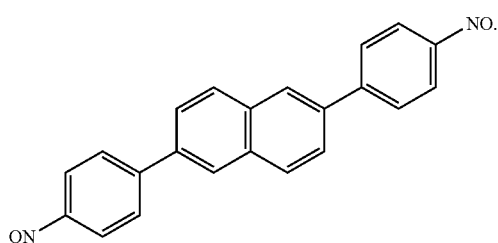

In an embodiment, L$_2$ may comprise a nitrogen atom or

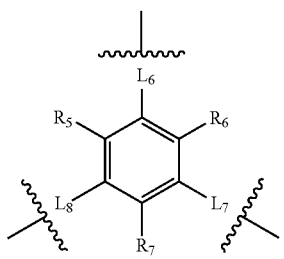

with R$_5$ to R$_7$ being independently selected from a hydrogen atom, an unsubstituted or substituted linear or branched C1-C6 alkyl group, or a halogen; and
L$_6$ to L$_8$, if present, being identical and a carbocyclic ring.

The unsubstituted or substituted linear or branched C1-C6 alkyl group may refer to a linear or branched chain of hydrocarbons having 1 to 6 carbon atoms with or without substituted with one or more of a halogen such as fluoride, chloride, bromide and iodide, a hydroxyl group, a phenyl group, an amino group, etc. Examples of linear or branched C1-C6 alkyl group may include the one as described above. The halogen on R$_5$ to R$_7$ may be fluoride, chloride, bromide or iodide and it is preferred that, if present, they are identical. The carbocyclic ring may be an unsubstituted or substituted C3-C10 carbocycles or mono-aromatic hydrocarbons as described herein.

In particular, R$_5$ to R$_7$ are identical and are selected from a hydrogen atom, an unsubstituted linear or branched C1-C6 alkyl group such as an unsubstituted linear or branched C1-C3 alkyl group such as methyl, ethyl, propyl, isopropyl or a halogen as described herein; and
  L$_6$ to L$_8$, if present, is a 6-membered carbocyclic ring such as a benzene, cyclohexane, cyclohexene, cyclohexa-1,3-diene, cyclohexa-1,4-diene.

As specific embodiments, the polynitroso compound having a structure of Formula (B) may comprise a structure having a formula of:

Formula (VII)

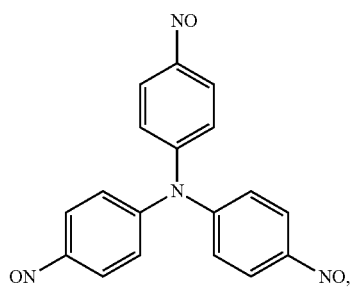

Formula (VIII)

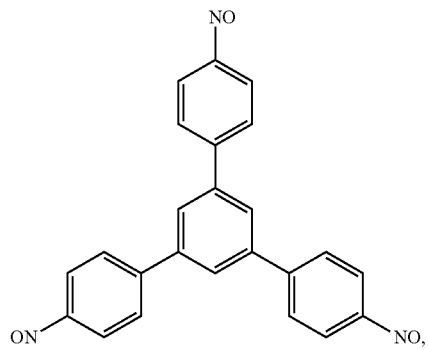

Formula (IX)

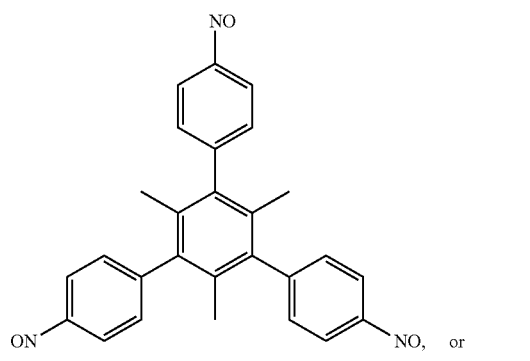

or

Formula (X)

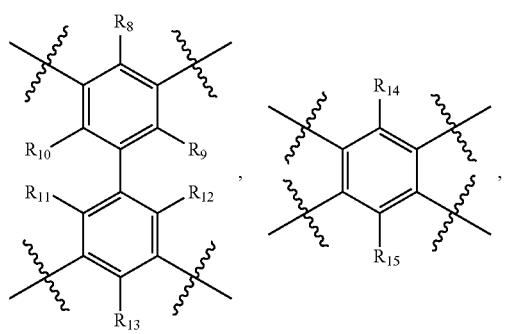

In an embodiment, L$_3$ may comprise a carbon atom, a C2-C4 alkenyl group,

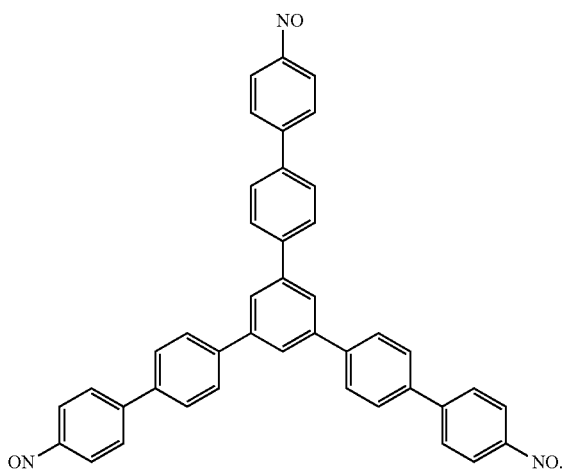

-continued

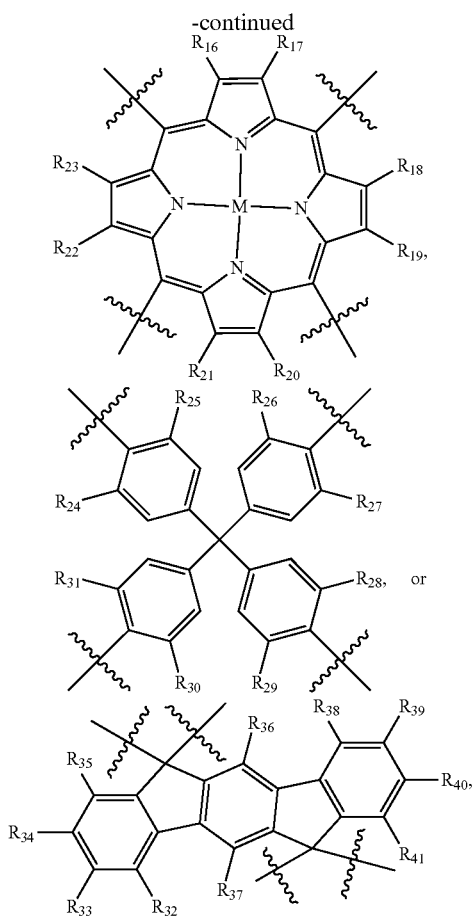

with $R_8$ to $R_{15}$ being independently selected from a hydrogen atom, a halogen or an unsubstituted or substituted linear or branched C1-C6 alkyl group; $R_{16}$ to $R_{23}$ being independently selected from a hydrogen atom, an unsubstituted or substituted linear or branched C1-C6 alkyl group, an aryl group, a halogen, and adjacent $R_{16}$ to $R_{23}$ may form a fused heterocyclic or carbocyclic ring; M being $H_2$ or a metal atom; $R_{24}$ to $R_{31}$ being independently selected from a hydrogen atom, a halogen and an unsubstituted or substituted linear or branched C1-C6 alkyl group; $R_{32}$ to $R_{41}$ being independently selected from a hydrogen atom, an unsubstituted or substituted linear or branched C1-C6 alkyl group, a halogen, and adjacent $R_{32}$ to $R_{41}$ may form a fused heterocyclic or carbocyclic ring.

The C2-C4 alkenyl group may be an unsubstituted or substituted alkenyl group with 2 to 4 carbon atoms, such as an ethenyl, propenyl, butenyl with or without being substituted with methyl, ethyl, isopropyl, hydroxyl, halogen, amine, phenyl and the like.

The unsubstituted or substituted linear or branched C1-C6 alkyl group on $R_8$ to $R_{41}$ may refer to a linear or branched chain of hydrocarbons having 1 to 6 carbon atoms with or without substituted with one or more of a halogen such as fluoride, chloride, bromide and iodide, a hydroxyl group, a phenyl group, an amino group, etc. Examples of linear or branched C1-C6 alkyl group may include the one as described above. The halogen on $R_8$ to $R_{41}$ may be fluoride, chloride, bromide or iodide and it is preferred that, if present, the halogen within each of the following groups are identical: $R_8$ to $R_{13}$, $R_{14}$ and $R_{15}$, $R_{16}$ to $R_{23}$, and $R_{32}$ to $R_{41}$.

The aryl group on $R_{16}$ to $R_{23}$, if present, may refer to an aromatic hydrocarbon, particularly those derived from benzene such as phenyl, naphthyl, tolyl, xylyl, hydroxyphenyl, halophenyl and the like.

Adjacent $R_{16}$ to $R_{23}$ and $R_{32}$ to $R_{41}$ may form a fused heterocyclic or carbocyclic ring. That is, for example, one or more of the following pairs may form a fused heterocyclic or carbocyclic ring: $R_{16}$ and $R_{17}$, $R_{18}$ and $R_{19}$, $R_{20}$ and $R_{21}$, $R_{22}$ and $R_{23}$, $R_{32}$ and $R_{33}$, $R_{33}$ and $R_{34}$, $R_{34}$ and $R_{35}$, $R_{38}$ and $R_{39}$, $R_{39}$ and $R_{40}$, and $R_{40}$ and $R_{41}$. The fused heterocyclic ring may be C2-C5 heterocycles as described herein whereas the fused carbocyclic ring may be an unsubstituted C3-C10 cycloalkanes, cycloalkenes, cycloalkynes or their derivatives as described herein or a benzene or its derivatives as described herein. M in $L_3$ may be $H_2$ or a metal atom. In an embodiment where M is $H_2$, it means that two hydrogen atoms are provided to bond to two nitrogen atoms in the adjacent nitrogen-containing five-membered rings to form —NH bonding, i.e., forming pyrroles. The metal atom may be selected from iron, cobalt, nickel, copper, zinc, titanium, vanadium, chromium, manganese, molybdenum, zirconium, cadmium, antimony, niobium, palladium or platinum.

In particular, $R_8$ to $R_{13}$ are identical and are selected from a hydrogen atom, and an unsubstituted linear or branched C1-C6 alkyl group such as an unsubstituted linear or branched C1-C3 alkyl group such as methyl, ethyl, propyl, isopropyl;

$R_{14}$ and $R_{15}$ are identical and are selected from a hydrogen atom, and an unsubstituted linear or branched C1-C6 alkyl group; such as an unsubstituted linear or branched C1-C3 alkyl group such as methyl, ethyl, propyl, isopropyl;

$R_{16}$ to $R_{23}$ are identical and are selected from a hydrogen atom, an unsubstituted linear or branched C1-C6 alkyl group such as an unsubstituted linear or branched C1-C3 alkyl group such as methyl, ethyl, propyl, isopropyl, and adjacent $R_{16}$ to $R_{23}$ may form a fused 6-membered carbocyclic ring such as benzene or cyclohexane; M being $H_2$ or a metal atom selected from iron, nickel, copper, zinc or manganese;

$R_{24}$ to $R_{31}$ are identical and are selected from a hydrogen atom, and an unsubstituted linear or branched C1-C6 alkyl group such as an unsubstituted linear or branched C1-C3 alkyl group such as methyl, ethyl, propyl, isopropyl; and $R_{32}$ to $R_{41}$ are identical and are selected from a hydrogen atom, an unsubstituted linear or branched C1-C6 alkyl group such as an unsubstituted linear or branched C1-C3 alkyl group such as methyl, ethyl, propyl, isopropyl, and adjacent $R_{32}$ to $R_{41}$ may form a fused 6-membered carbocyclic ring such as benzene and cyclohexane.

As specific embodiments, the polynitroso compound having a structure of Formula (C) may comprise a structure having a formula of:

Formula (XI)
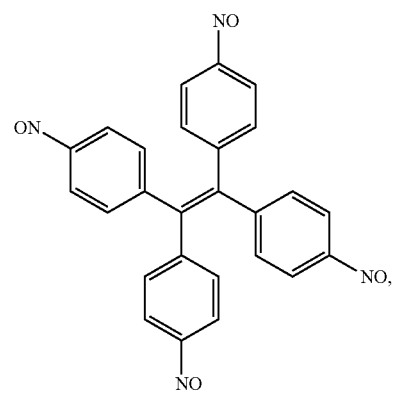
Formula (XV)
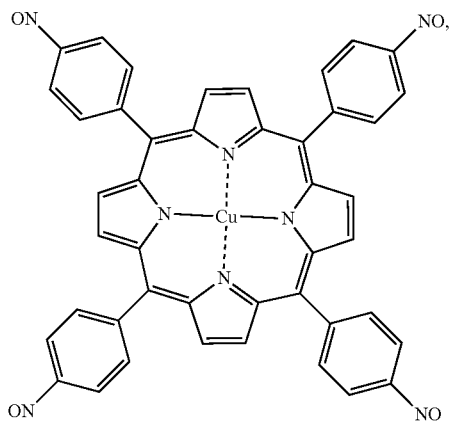
Formula (XII)
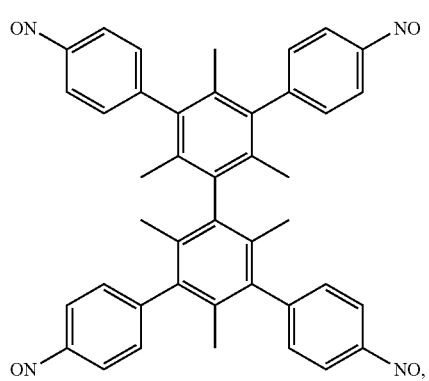
Formula (XVI)
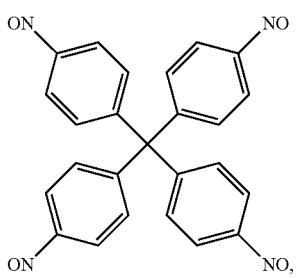
Formula (XIII)
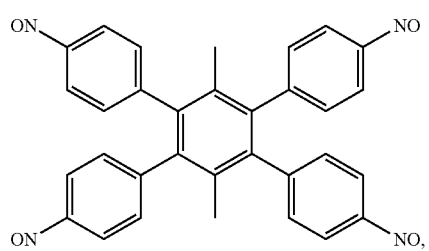
Formula (XVII)
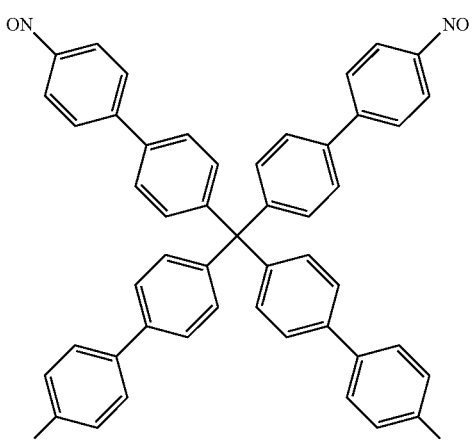
Formula (XIV)
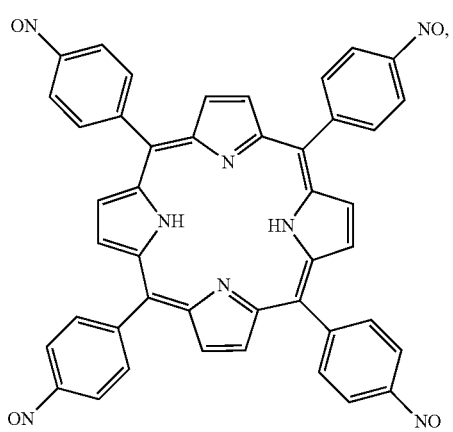
Formula (XVIII)
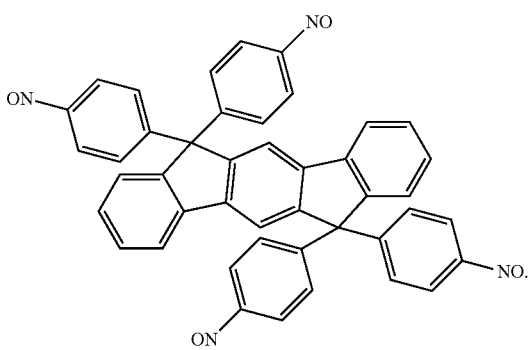
In an embodiment, $L_4$ may comprise a 6-membered carbocyclic ring such as benzene, cyclohexane, cyclohexene, cyclohexa-1,3-diene, cyclohexa-1,4-diene. As a specific embodiment, the polynitroso compound having a structure of Formula (D) may comprise a structure having a formula of.

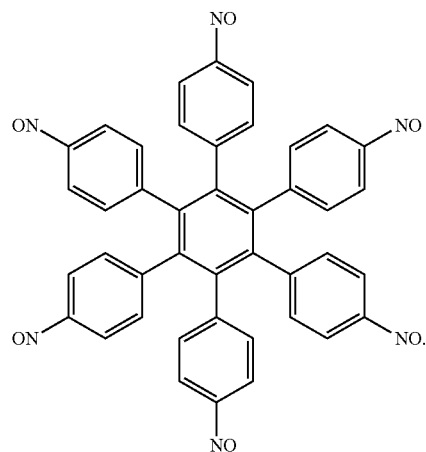

Formula (XIX)

The polynitroso compounds of the present invention may comprises monomeric form, polymeric form, and a combination thereof. The phrase "polymeric" generally denotes that two or more molecules of the polynitroso compound may be joined by chemical bonds such as covalent or intermolecular bond. For example, the polynitorso compound may be arranged in dimeric form (i.e. two molecules of polynitroso compound are joined by intermolecular bond such as cis- or trans-azodioxy bond), trimeric form, tetrameric form, pentameric form, hexameric form, etc.

Figure 2:
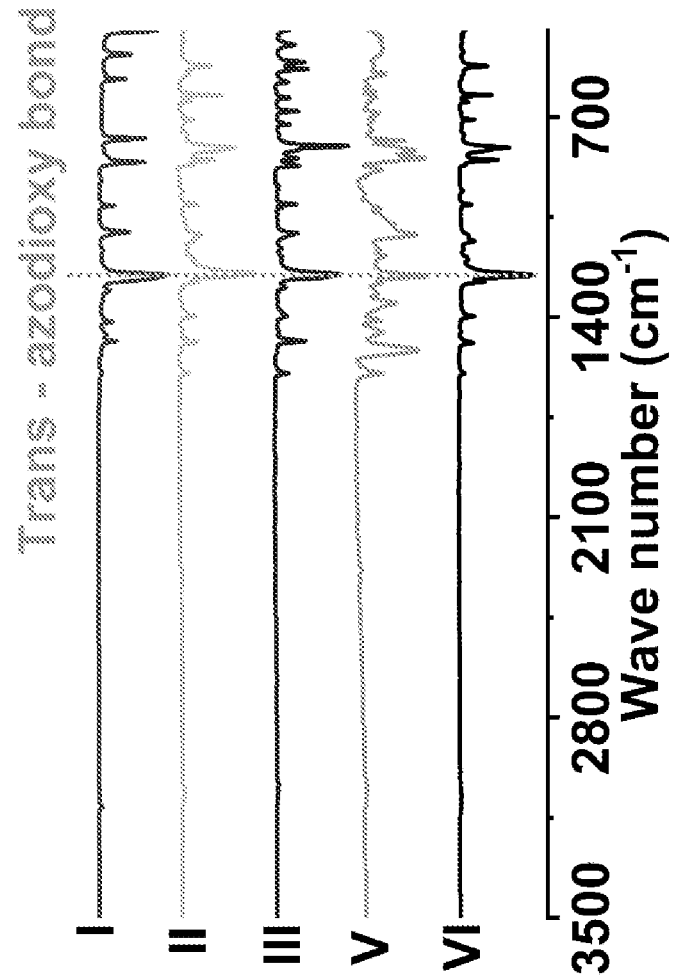
FIG. 2 is a FT-JR spectra of the polynitroso compounds I, II, III, V and VI.

The monomeric form or polymeric form of the polynitroso compound may be characterized by FTIR spectroscopy. For example, in an embodiment where the polynitroso compound is in monomeric form, it may be characterized by the IR absorption peaks at about 1485 cm$^{-1}$ and 1101 cm$^{-1}$, which are corresponding to the N=O and C—N=O stretching, respectively (FIG. 1). In another embodiment where the polynitroso compound is in polymeric form, it may be characterized by the IR absorption peaks at about 1255 cm$^{-1}$, corresponding to the stretching of trans-azodioxy bonds (FIG. 2).

Figure 3:
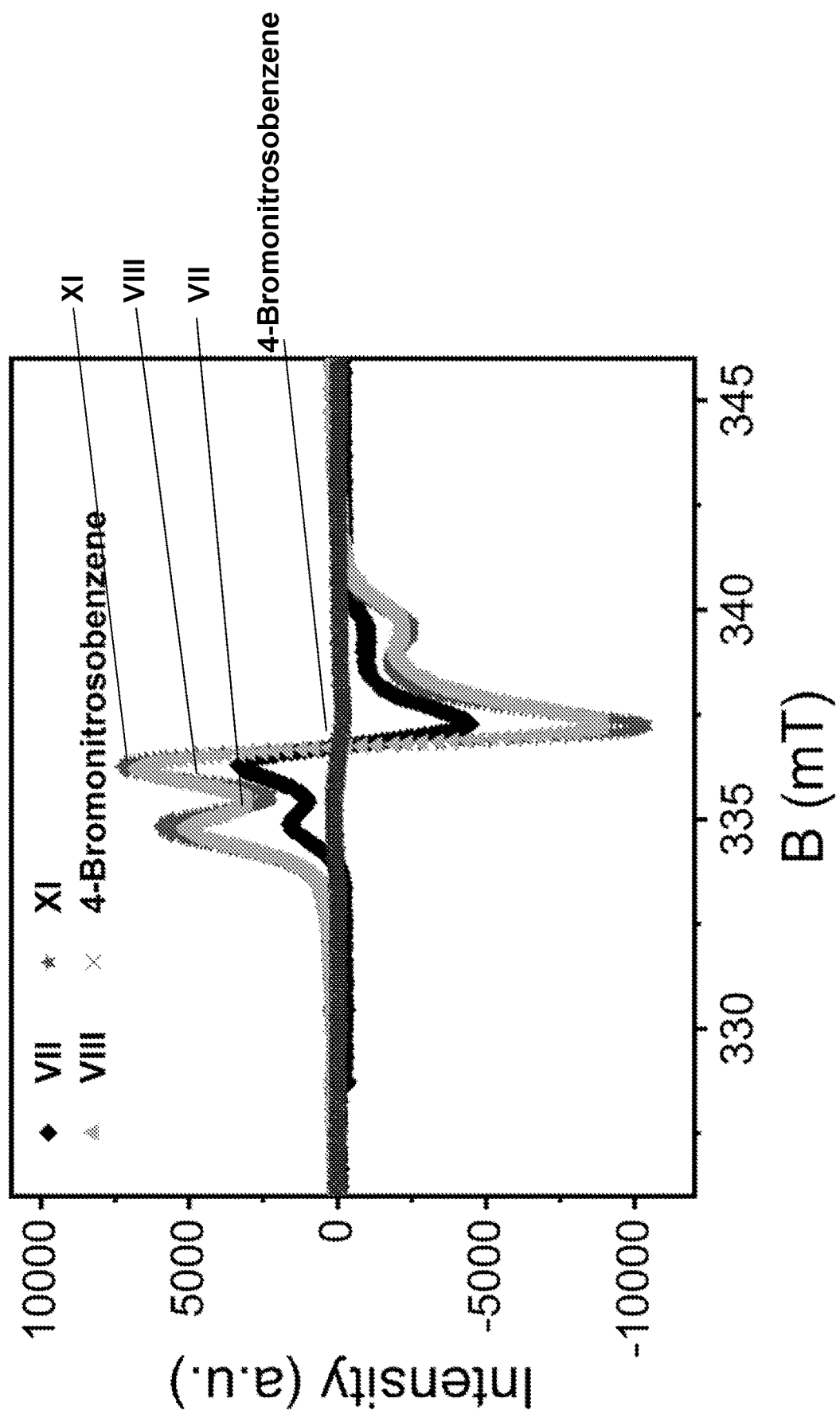
FIG. 3 is an electron paramagnetic resonances (EPR) spectra of polynitroso compounds VII, VIII, and XI.

As mentioned herein, it is believed the polynitorso compound of the present invention possess radical character. In other words, the polynitroso compound of the present invention is a compound radical. The term "compound radical" generally describes a chemical species, in particular, a compound molecule having at least one unpaired electron. The radical nature/character of the polynitroso compound may be characterized by electron paramagnetic resonances (EPR) spectroscopy. Referring to FIG. 3, for example, when the polynitroso compound possesses radical nature (or is radically active), sharp peaks would be observed in the EPR spectrum and a g value of about 2.005 would be obtained. If otherwise, no such peak would be observed (FIG. 3, 4-bromonitrosobenzene).

It is believed that the radical activity of polynitroso compound of the present invention may last for at least 6 months. That said, the polynitroso compound, as a compound radical, may remain active for at least 6 months. In an example embodiment, the polynitroso compound (as a compound radical) may remain active from about 6 months. It is believed that such a long-lasting radical activity would make the polynitroso compound of the present invention particularly suitable for use in energy storage device, such as rechargeable batteries such as rechargeable lithium-ion battery, rechargeable organic radical battery, etc.

A method for preparing the polynitroso compound is described below, i.e., for preparing a polynitroso compound comprising a structure having a formula of:

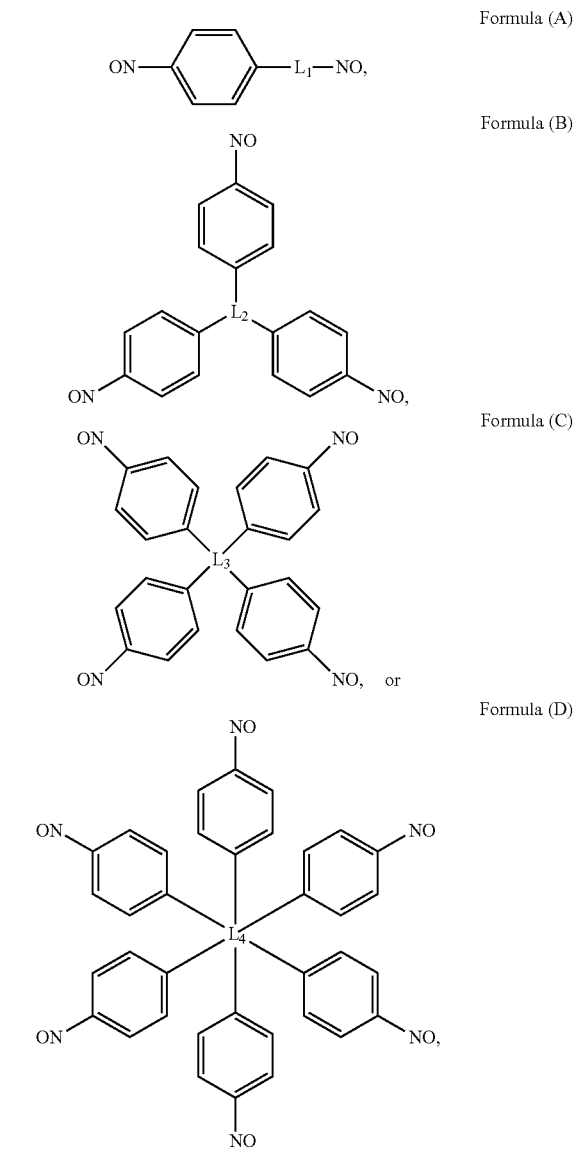

Formula (A)

Formula (B)

Formula (C)

Formula (D)

with $L_1$ to $L_4$ as defined herein.

The method comprises the steps of:
a) providing a precursor compound comprising two or more terminal trifluoroborate groups or silyl groups; and
b) conducting nitrosation to the precursor compound with a nitrosating agent.

In an embodiment, the precursor compound may be a compound having a structure similar to Formula (A) to Formula (D), with the nitroso groups being replaced with terminal trifluoroborate groups or silyl groups. The terminal trifluoroborate group may comprise trifluoroborate salt such as potassium trifluoroborate whereas the terminal silyl groups may be a trimethylsilyl (TMS) group.

In particular embodiments, the precursor compound may comprise a structure having a formula of:

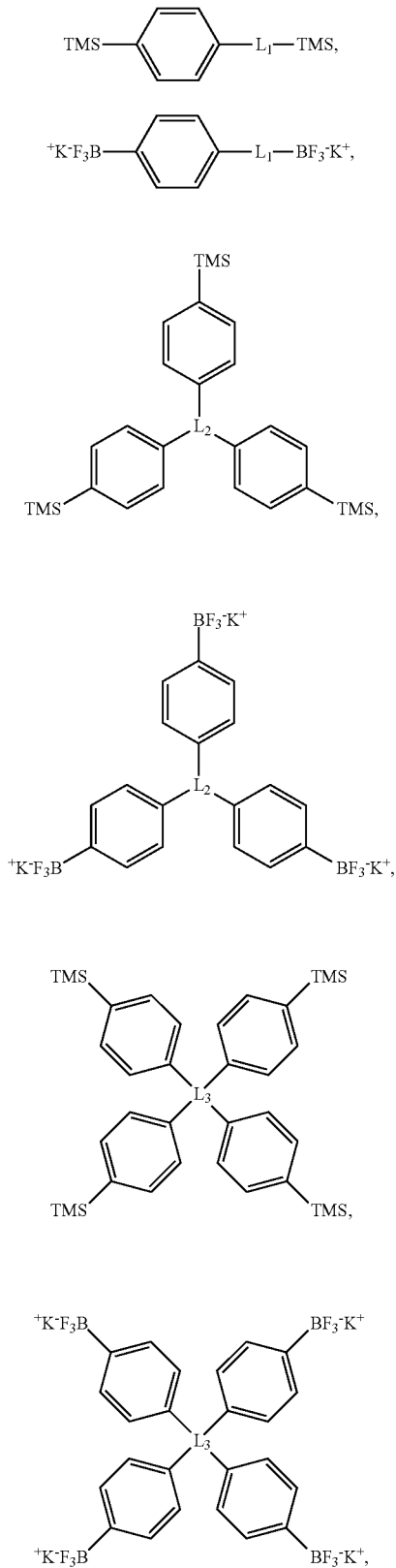

Formula (A1)

Formula (A2)

Formula (B1)

Formula (B2)

Formula (C1)

Formula (C2)

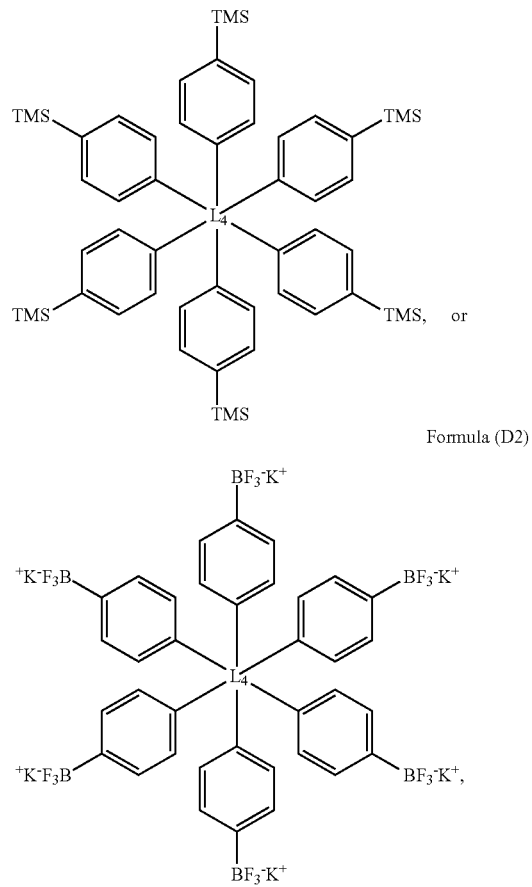

Formula (D1)

Formula (D2)

with $L_1$ to $L_4$ as defined herein.

In an embodiment, step a) may optionally comprise the step of preparing the precursor compound having a structure of Formula (A1), Formula (B1), Formula (C1) or Formula (D1) from their corresponding bromo-precursor compounds. In particular, the bromo-precursor may be the one with the TMS groups being replaced with bromide. As an exemplary embodiment, when the precursor compound is the one with a structure of Formula (B1), the corresponding bromo-precursor compound may have a structure of Formula (B3):

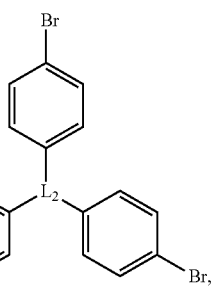

Formula (B3)

with $L_2$ as defined herein.

In particular, the conversion of the bromo-precursor compound to the precursor compound with a structure of Formula (A1), Formula (B1), Formula (C1) or Formula (D1) may be conducted in the presence of an organolithium agent such as methyllithium, n-butyllithium, sec-butyllithium, isopropyllithium, tert-butyllithium, phenyllithium, etc. As a specific embodiment, the organolithium agent may be n-butyllithium (n-BuLi).

In another embodiment, step a) may optionally comprise the step of preparing the precursor compound having a structure of Formula (A2), Formula (B2), Formula (C2) or Formula (D2) from their corresponding boronic acid-precursor compounds. As an exemplary embodiment, when the precursor compound is the one with structure of Formula (B2), the corresponding boronic acid-precursor compound may have a structure of Formula (B4):

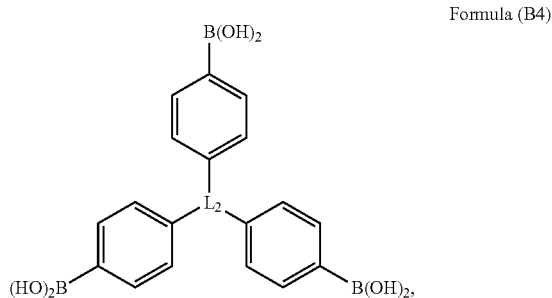

Formula (B4)

with $L_2$ as defined herein.

In particular, the conversion of the boronic acid-precursor compound to the precursor compound with a structure of Formula (A2), Formula (B2), Formula (C2) or Formula (D2) may be conducted in the presence of a fluorinating agent such as n-Bu$_4$NHF$_2$.

In an alternative embodiment, the boronic acid-precursor compound such as the one with Formula (B4), may react with an organohalide such as an organobromide, in particular, an organobromide substituted with a (terminal) TMS group such as an orgnobromide intermediate having a structure of Formula (a):

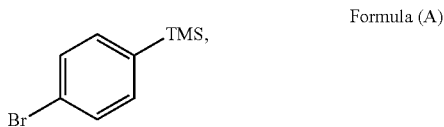 [SMILES: C[Si](C)(C)c1ccc(Br)cc1]

Formula (A)

to form a precursor compound having a structure of Formula (B1)':

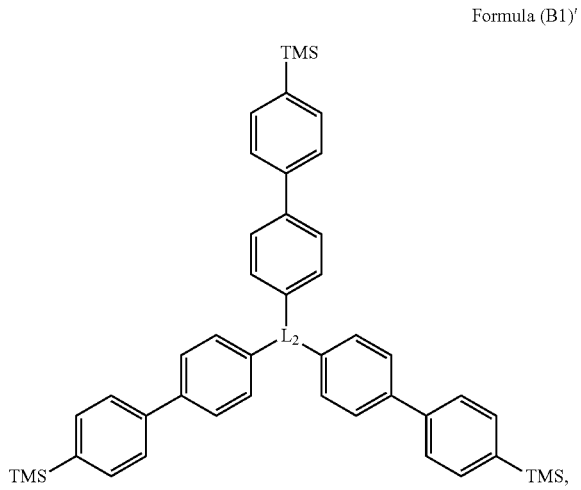

Formula (B1)' with $L_2$ as defined herein.

In particular, the reaction between the orgnobromide intermediate and the boronic acid-precursor compound may be by way of a Suzuki (coupling) reaction. It would be understood in the art that such reaction is a cross-coupling reaction, where the coupling partners, the boronic acid precursor compound such as the one with a structure of Formula (B4) in an embodiment and an organohalide such as the orgnobromide intermediate having a structure of Formula (a) in an embodiment, would form a single C—C bond in the presence of a palladium(0) catalyst such as PdCl$_2$(PPh$_3$)$_2$, Pd(PPh$_3$)$_4$, Pd(OAc)$_2$(PPh$_3$)$_2$, and the like.

Step b) particularly comprises the steps of:
i) preparing a reaction mixture of the precursor compound and the nitrosating agent in a reaction solvent;
ii) stirring the reaction mixture for at least about 30 min for at least about 20° C.; and
iii) isolating the polynitroso compound having a structure of Formula (A), Formula (B), Formula (C), or Formula (D) and optionally purifying the polynitroso compound.

In an embodiment, the precursor compound may be provided in form of a solvent mixture. That is, the precursor compound may be in form of a mixture with at least a part of the reaction solvent.

In particular, the reaction solvent may be selected from the group consisting of 1,2-dichlorobenzene, dichloromethane, 1,2-dichloroethane, tetrahydrofuran, n-hexane, heptane, ethyl acetate, toluene, acetonitrile and a combination thereof. As a specific embodiment, the reaction solvent is acetonitrile.

The nitrosating agent may be a nitrosonium salt. In particular, the nitrosoium salt may be selected from the group consisting of nitrosyl bromide (NOBr), nitrosyl chloride (NOCl), nitrosylsulfuric acid (NOHSO$_4$), posattium nitrite (KNO$_2$), sodium nitrite (NaNO$_2$), silver nitrite (AgNO$_2$), nitrosonium tetrafluoroborate (BF$_4$NO), and a combination thereof. As a specific embodiment, the nitrosating agent is BF$_4$NO.

The nitrosation maybe conducted under a neutral or acidic condition. In an embodiment where the nitrosation is conducted under an acidic condition, the acidic condition may be adjusted by hydrochloric acid, hydrobromic acid, sulfuric acid or a combination thereof.

The reaction mixture of the precursor compound and the nitrosating agent in step bi) may be of a predefined mole ratio. In particular, the precursor compound and the nitrosating agent may be mixed at a mole ratio of A:B. Preferably, A is from about 2 to about 4, from about 1.9 to about 4, from about 2.1 to about 4, from about 2 to about 3.9, from about 2 to about 4.1, or from 1.9 to about 4.1. It is also preferred that B is from about 3 to about 10, from about 3 to about 10.2, from about 3 to about 10.1, from about 2.9 to about 10, from about 2.9 to about 10.1, from about 2.9 to about 10.2, from about 3.3 to about 10.2, or from about 3.4 to about 10.2.

In preferred embodiments, the precursor compound and the nitrosating agent in step bi) may be mixed at a predefined mole ratio so as to obtain the polynitroso compound having a particular structure. In one example embodiment, where A:B being 2:3.4, the polynitroso compound with a structure of Formula (A) may be preferably obtained. In another example embodiment, where A:B being 3:5.1, the polynitroso compound with a structure of Formula (B) may be preferably obtained. In a further example embodiment, where A:B being 4:6.8, the polynitroso compound with a structure of Formula (C) may be preferably obtained. In a still further example embodiment, where A:B being 4:10.2, the polynitroso compound with a structure of Formula (D) may be preferably obtained.

"Isolating" the polynitroso compound means at least partially separating the compound from other components such as side products, the reactants and the reaction solvent present in the reaction mixture after step bii).

Step (iii) may in particular comprise filtering the reaction mixture for obtaining a filtrate, subjecting the reaction mixture to centrifugation, allowing the polynitroso compound to form precipitate in water such as cold water or a salt solution such as sodium chloride potassium chloride, sodium carbonate, sodium bicarbonate, sodium acetate, or ammonium chloride solutions and the like, adding a precipitation solvent to the filtrate for obtaining a precipitate and washing the precipitate with a washing solvent.

The purification step in step biii) may be performed by column chromatograph, such as silica-gel column chromatography, alumina column chromatography, recrystallization and the like.

The polynitroso compound obtained after step biii) may be optionally dried at about room temperature to about 50° C., about 50° C.-70° C., about 70° C.-90° C., about 90° C.-110° C. under vacuum for a period of about 4 hours to 6 hours, about 6 hours to 8 hours, about 8 hours to 12 hours, about 8 hours to 14 hours, about 10 hours to 12 hours.

As specific embodiments, the method may be used for preparing polynitroso compounds having a structure of Formula (I) to Formula (XIX) as described herein.

Another aspect of the present invention pertains to an electrode material for an energy storage device comprising a polynitroso compound having a monocyclic core with at least one terminal nitroso group.

In particular, the polynitroso compound may comprise a structure having a formula of:

Formula (A)
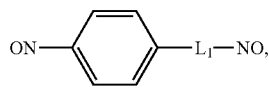

Formula (B)
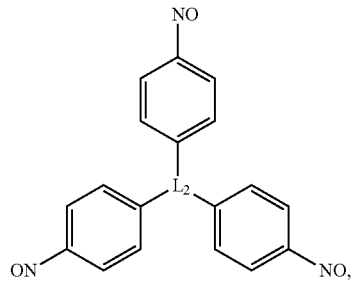

Formula (C)
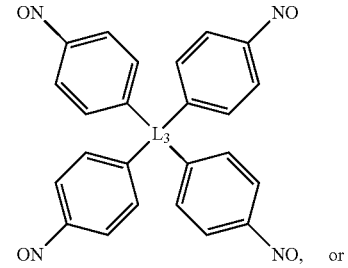

or

Formula (D)
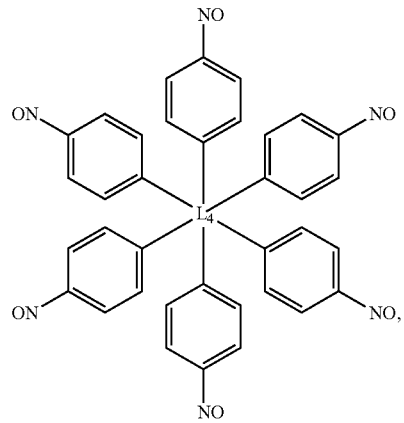

with $L_1$ to $L_4$ as defined herein.

In an embodiment where the polynitroso compound has a structure of Formula (A), the polynitroso compound may comprise a structure having a formula of:

Formula (I)
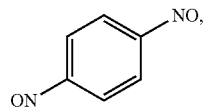

Formula (II)
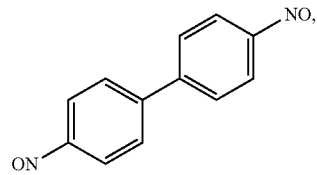

Formula (III)
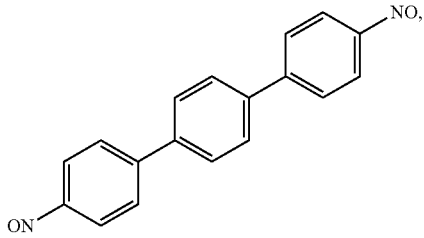

Formula (IV)
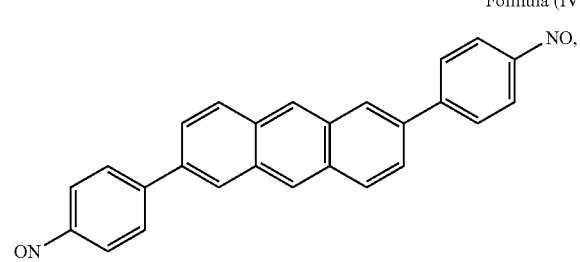

Formula (V)

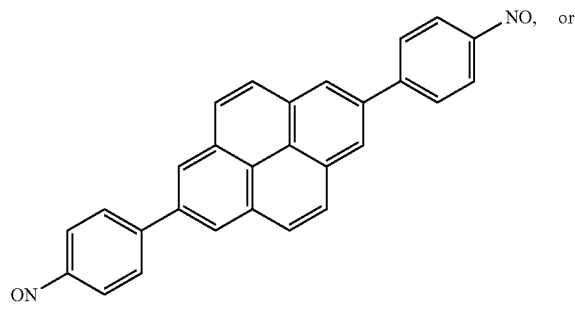

or

Formula (VI)

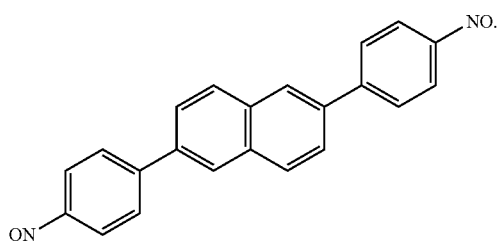

In an embodiment where the polynitroso compound has a structure of Formula (B), the polynitroso compound may comprise a structure having a formula of:

Formula (VII)

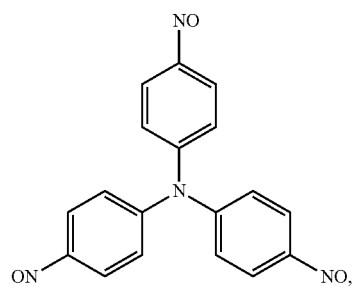

Formula (VIII)

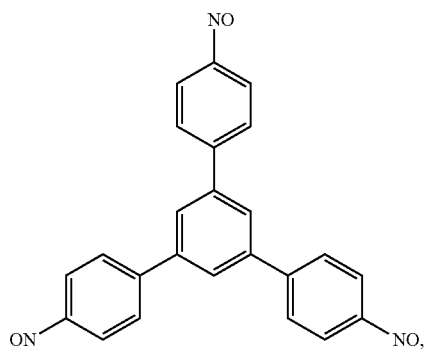

Formula (IX)

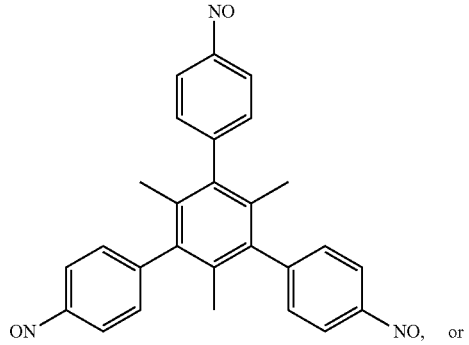

or

Formula (X)

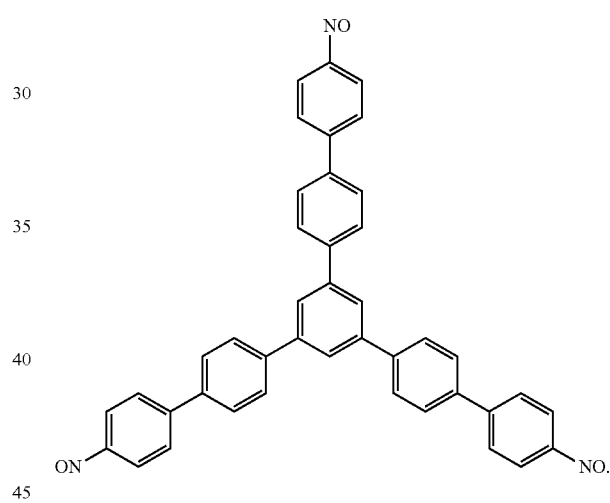

In an embodiment where the polynitroso compound has a structure of Formula (C), the polynitroso compound may comprise a structure having a formula of:

Formula (XI)

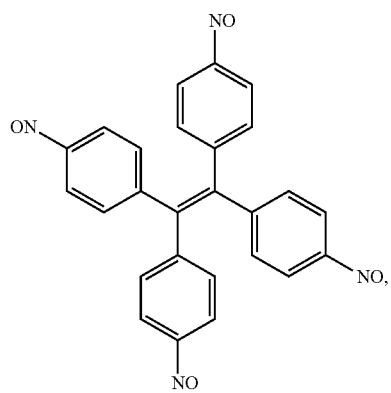

Formula (XII)
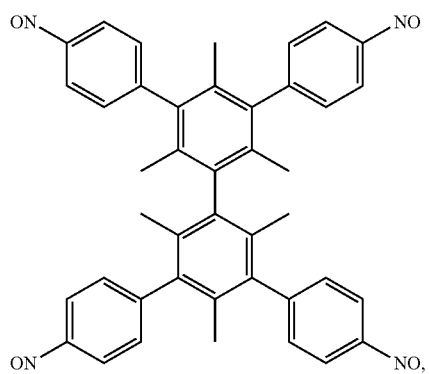
Formula (XIII)
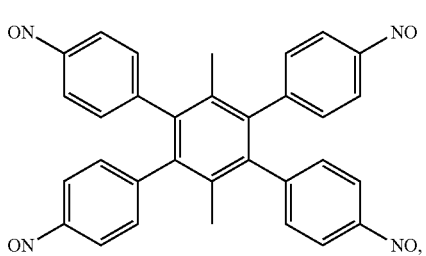
Formula (XIV)
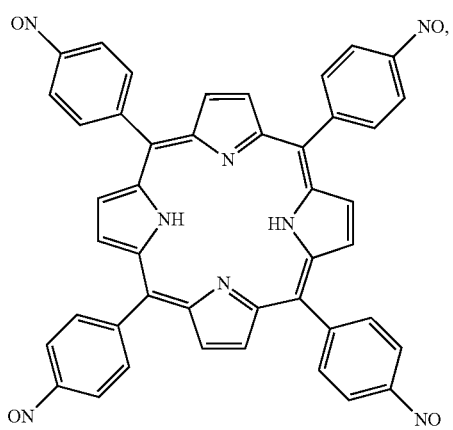
Formula (XV)
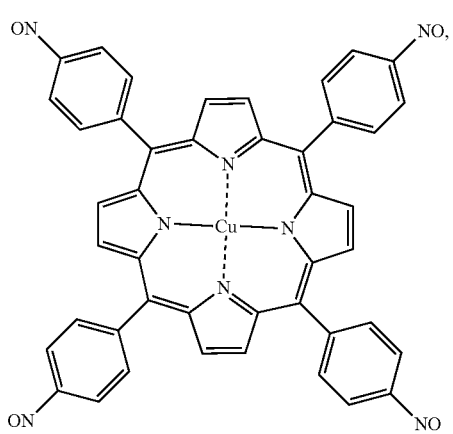
Formula (XVI)
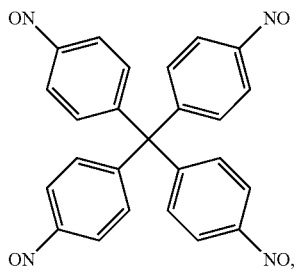
Formula (XVII)
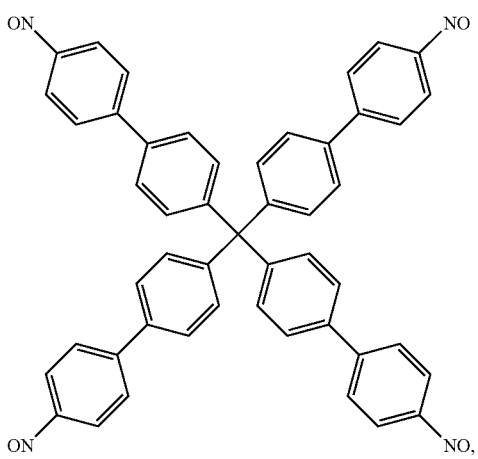
Formula (XVIII)
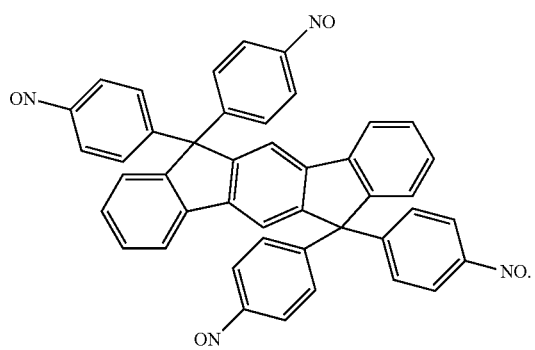
In an embodiment where the polynitroso compound has a structure of Formula (D), the polynitroso compound may comprise a structure having a formula of:

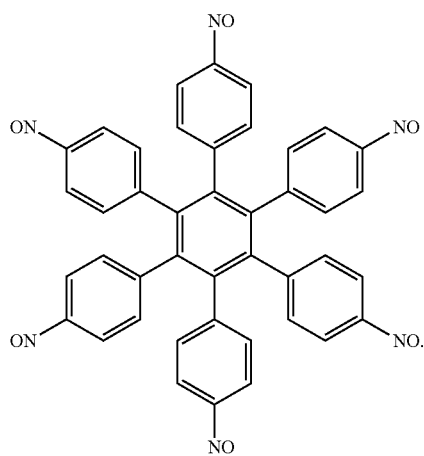

Formula (XIX)

As a specific embodiment, the polynitroso compounds, in particular the polynitroso compounds that have a structure of Formula (VII) may be used as a cathode material for a $L_1$-ion battery. For example, the polynitroso compound, in particular, the polynitroso compound having a structure of Formula (VII) may be mixed with a conductive material such as a conductive carbon such as Ketjen Black, and a binder such as polyvinylidene fluoride (PDVF) at a predefined weight ratio such as about 3:5:2, in the presence of a solvent such as 1-methyl-2-pyrrolidinone (NMP), to form slurry. The slurry may then coated on a metal sheet such as an aluminium sheet using, for example, a coater. The as-formed assembly (i.e., the crude cathode) may then dried under vacuum at about 60° C., about 65° C., about 70° C., about 75° C., about 80° C., about 85° C., about 90° C., about 95° C., about 100° C., about 105° C., or about 110° C. for about 6 to 16 hours, about 6 to 9 hours, about 6 to 12 hours, about 9 to 12 hours, about 9 to 16 hours, preferably for about 12 hours, to remove the solvent.

The cathode as described herein may be assembled to an energy storage device for operation. The present invention thus further relates to an energy storage device with a cathode comprising the polynitroso compound as described herein. The energy storage device is particularly a rechargeable battery having, in electrical communication, an electrolyte, an anode, and a cathode comprising the polynitroso compound as described herein. The selection of anode as well as the electrolyte may depend on the type of battery. For example, when the battery is a Li-ion battery, the anode may be the lithium metal, the alloy thereof, or any other materials embedded with lithium ion, such as graphite material embedded with lithium ion; whereas the electrolyte may be the one containing lithium ion. The electrolyte may be in aqueous solution form, organic solution form, solid form, gel (e.g., hydrogel) form, etc. When the electrolyte is in aqueous solution or in organic solution form, the battery is preferred to have a separator for preventing short circuit of the battery during operation. The shape of the battery may vary, such as being a coin shape, a rod shape, a rectangular shape, a cylindrical shape and the like.

In an embodiment, the energy storage device may be a rechargeable Li-ion battery. The battery may be implemented as a coin cell, which contains a cathode containing the polynitroso compound of the present invention, such as the polynitroso compound having a structure of Formula (VII), an anode comprising lithium, such as lithium metal, and an electrolyte comprising LiTFSI and PY13TFSI. The coin cell may include a separator separating the anode and the cathode within the cell.

As mentioned herein, the polynitroso compounds of the present invention are believed to be suitable for use in energy storage device. In particular, it is believed that the redox active sites provided by the nitrogen or oxygen atoms of nitroso groups as well as the monocyclic or polycyclic core, particularly those with aromaticity, may facilitate diffusion of ions (e.g., ion insertion and extraction) of the device, and therefore providing excellent stability of the electrode in the electrolyte, and maximizing the capacity and reversibility of the device.

In an embodiment, the device may have a stabilized discharge capacity from about 270 mA h $g^{-1}$ to about 117 mA h $g^{-1}$ at a current density from about 50 mA $g^{-1}$ to about 1 A $g^{-1}$ over a voltage window of about 1.3 V to about 4.3 V.

In another embodiment, the the device may have a specific capacity of about 300 mA h $g^{-1}$ after 100 charge/discharge cycles under a current density of about 100 mA $g^{-1}$.

In a further embodiment, the device may have about 85% capacity retention after about 1000 charge/discharge cycles under a current density of about 1 A $g^{-1}$.

EXAMPLES

Materials and Reagents Used

All reagents and solvents were obtained from commercial suppliers and were used without further purification. Triphenylamine (TPA) and 1-bromo-2,5-pyrolidinedione (NBS) were purchased from TCI; Nitrosonium tetrafluoroborate ($BF_4NO$) was purchased from Thermo Scientific (Alfa Aesar); n-butyllithium (2.5 M in hexane), 1-bromo-4-(trimethylsilyl)benzene and trimethylsilyl chloride were purchased from Macklin. Tetrahydrofuran was dried and distilled through treated with sodium.

The cathode was prepared by coating the ground slurry of active materials (tris(4-nitrosophenyl)amine, TPA-3NO (Formula (VII) of the present invention) with Ketjen Black as conductive carbon and polyvinylidene fluoride (Sigma-Aldrich) (PVDF) as the binder in a weight ratio of 3:5:2 with 1-methyl-2-pyrrolidinone (NMP) as solvent on aluminum foil. Then, the slurry was cast on the Al foil current collector and dried at 60° C. for 12 h under vacuum. CR2032 coin cells were fabricated in an Ar-filled glove box (MIKROUNA Super) with 0.3 M LiTFSI in PY13TFSI (v:v=1:1), Celgard 2500 as the separator and lithium as the counter electrode.

Instrumentation and Characterization

High-resolution mass spectra (HRMS, m/z) were obtained by electrospray ionization (ESI) coupled to a quadrupole-time-of-flight detector (Bruker maXis). UV-vis spectra were recorded by a Hitachi UH4150 UV-VIS-NIR Spectrophotometer. Fourier transform infrared (FT-IR) spectra were acquired on PerkinElmer FTIR Spectrometer. NMR spectra were recorded on Bruker Avance-300 and Avance-400 (400 MHz for $^1H$, 100 MHz for $^{13}C$) spectrometers. Chemical shifts (δ) were reported in parts per million (ppm) relative to TMS as internal standard. The following abbreviations were used to describe peak splitting patterns when appropriate: br=broad, s=singlet, d=doublet, t=triplet, q=quartet, m=multiplet, dd=doublet of doublet, dt=doublet of triplet.

Coupling constants J were reported in hertz (Hz). Thermal analyses were performed using a PerkinElmer TGA 8000 thermogravimetric analyser. Crystallographic Analysis XRD data were collected on X-ray Diffractometer (Rigaku Smart-Lab 9 kW—Advance). EPR spectra were acquired on a commercial X-band CW EPR spectrometer (Bruker EMX), with the following settings: frequency, 9.4489 GHz; microwave power, 29.0 mW; modulation amplitude, 100 µT; time constant, 0.092 s.

Electrochemical measurement, including CV and EIS were conducted on CHI Instruments electrochemical workstation (CHI660E). Land CT2001A battery instrument was used to test the galvanostatic discharge-charge and rate performance within potential 1.3-4.3 V at diverse current densities.

The kinetics of the charge/discharge process may be determined by calculating the slope (b) in a plot of peak current against scanning rate, with the following the formula:

$$\log i = b \log v + \log a$$

where i is the peak current, v is the scanning rate, and a, and b are the constants. The b value is the slopes of the log v and log i plots. When b=0.5, the Li-ion storage process is mainly diffusion controlled. As b=1, pseudocapacitive behavior dominates the Li-ion storage process.

Example 1A

Preparation of Polynitroso Compound I

Figure 4:
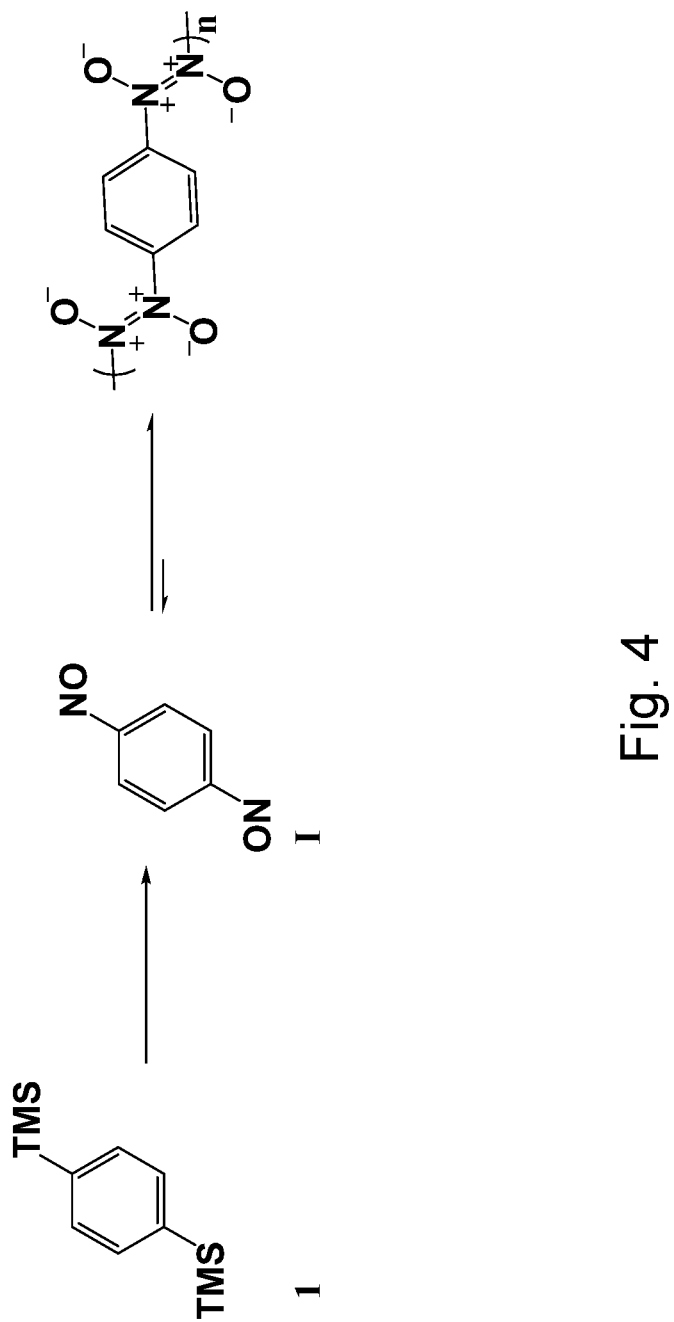
FIG. 4 is a synthetic scheme of polynitroso compound I.

The synthetic scheme of polynitroso compound I (i.e. the polynitroso compound of Formula (I) of the present invention) is shown in FIG. 4. Specifically, under argon atmosphere, to a solution of commercially available 1,4-bis(trimethylsilyl)benzene 1 (222 mg, 1.0 mmol) in dry $CH_3CN$ (15 ml) was added $BF_4NO$ (394 mg, 3.4 mmol) once at room temperature. After that, the reaction mixture was stirred for 30 min. The reaction was quenched by slowly dropping deoxygenated deionized water (30 mL). The precipitates formed after quenching were filtered and washed with the deoxygenated deionized water several times, and then dried in the dark under vacuum. Samples were stored and handled under $N_2$ atmosphere prior and during experiments. Yield: 120 mg (88%), yellow solid.

Example 1B

Preparation of Polynitroso Compound II

Figure 5:
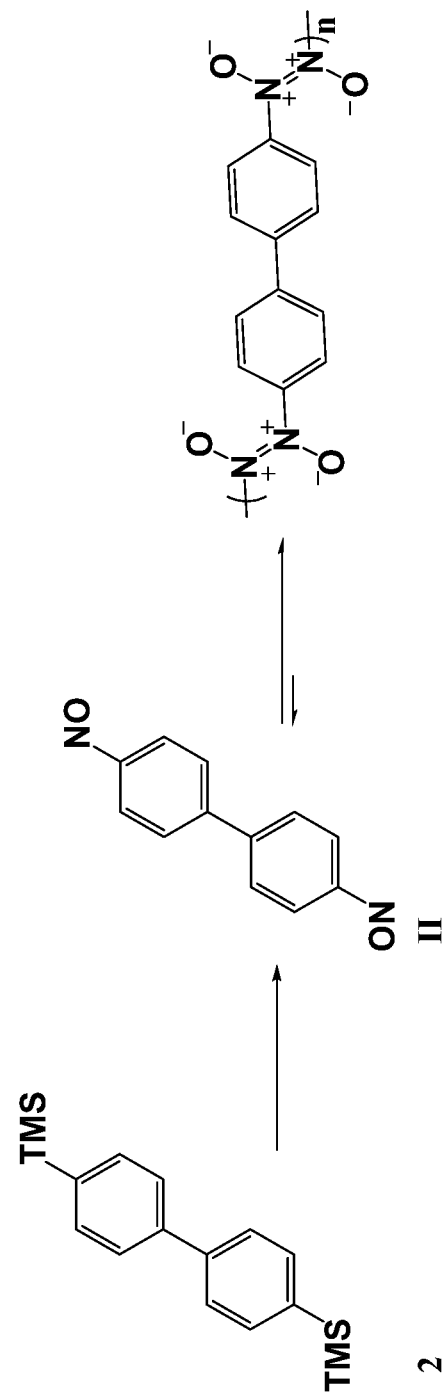
FIG. 5 is a synthetic scheme of polynitroso compound II.

The synthetic scheme of polynitroso compound II (i.e. the polynitroso compound of Formula (II) of the present invention) is shown in FIG. 5. Specifically, under argon atmosphere, to a solution of commercially available 2 (298 mg, 1.0 mmol) in dry $CH_3CN$ (15 ml) was added $BF_4NO$ (394 mg, 3.4 mmol) once at room temperature. After that, the reaction mixture was stirred for 30 min. The reaction was quenched by slowly dropping deoxygenated deionized water (30 mL). The precipitates formed after quenching were filtered and washed with the deoxygenated deionized water several times and then dried in the dark under vacuum. Samples were stored and handled under $N_2$ atmosphere prior and during experiments. Yield: 200 mg (94%), light yellow solid.

Example 1C

Preparation of Polynitroso Compound III

Figure 6:
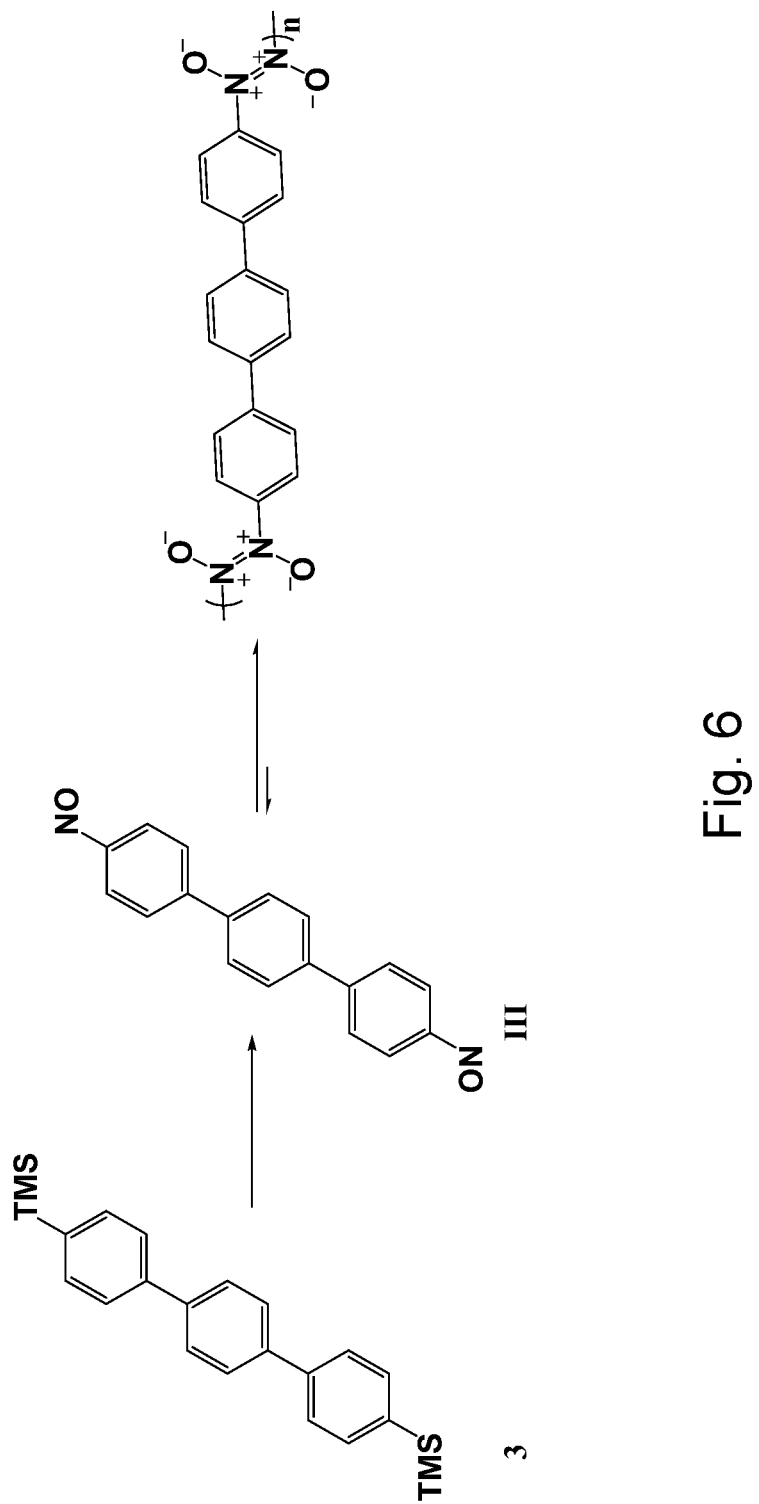
FIG. 6 is a synthetic scheme of polynitroso compound III.

The synthetic scheme of polynitroso compound III (i.e. the polynitroso compound of Formula (III) of the present invention) is shown in FIG. 6. Specifically, under argon atmosphere, to a solution of commercially available 3 (374 mg, 1.0 mmol) in dry $CH_3CN$ (15 ml) was added $BF_4NO$ (394 mg, 3.4 mmol) once at room temperature. After that, the reaction mixture was stirred for 30 min. The reaction was quenched by slowly dropping deoxygenated deionized water (30 mL). The precipitates formed after the quenching were filtered and washed with the deoxygenated deionized water several times and then dried in the dark under vacuum. Samples were stored and handled under $N_2$ atmosphere prior and during experiments. Yield: 267 mg (95%), light yellow solid.

Example 1D

Preparation of Polynitroso Compound V

Figure 7:
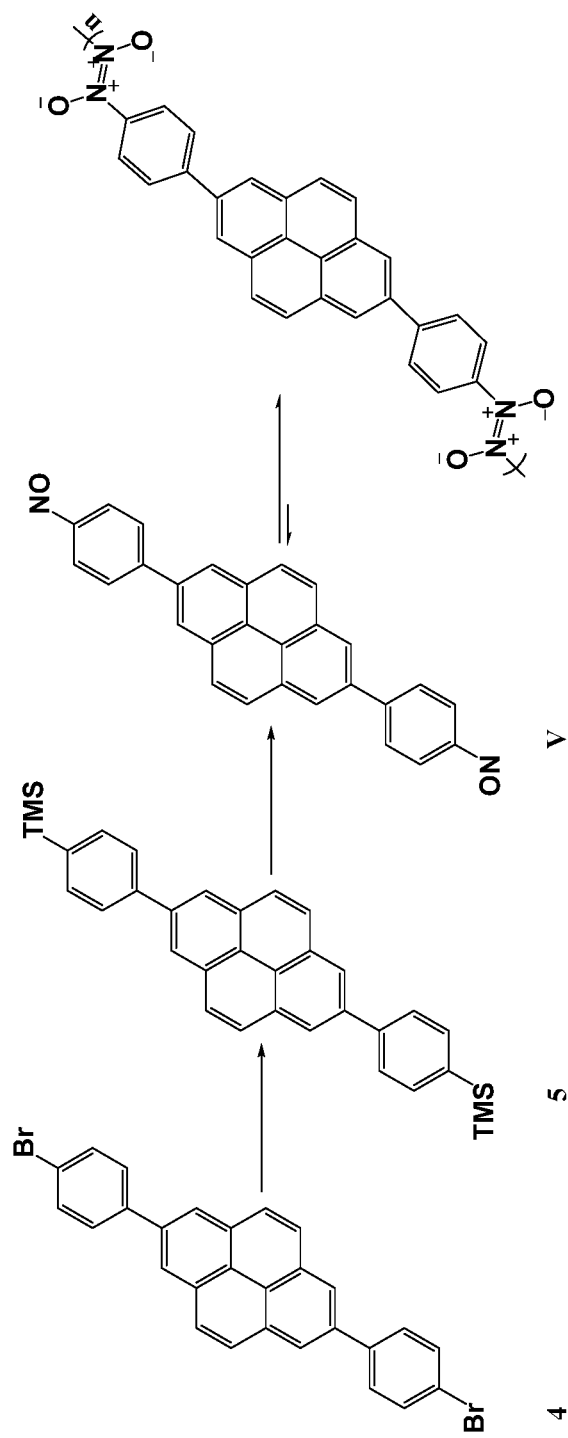
FIG. 7 is a synthetic scheme of polynitroso compound V.

The synthetic scheme of polynitroso compound V (i.e. the polynitroso compound of Formula (V) of the present invention) is shown in FIG. 7. Specifically, the preparation comprises two steps.

Step 1: a 500 mL three-neck round-bottom flask equipped with a magnetic stir bar was charged with 2,7-bis(4-bromophenyl)pyrene 4 (5 g, 1 mmol), and dry THF (250 mL). The solution was cooled down to −78° C. A solution of n-butyllithium (2.5 M in hexane, 12 mL, 3 mmol), was added dropwise over 10 min. After that, the reaction mixture was stirred for 30 min. Then, trimethylsilyl chloride (7 mL, 6 mmol) was added dropwise over 5 min and warmed up to room temperature (RT) for 3 hours. The resulting mixture was quenched with water (250 mL), extracted with ethyl acetate (250 mL×2). The organic phase was separated, washed twice with brine, dried over anhydrous $MgSO_4$. The organic phase was concentrated under reduced pressure, and the residue was washed with ethanol several times and dried in vacuum at 50° C. to afford 5 as a white powder (Yield: 4 g, 80%). $^1H$ NMR (400 MHz, $CDCl_3$) δ 8.41 (s, 4H), 8.15 (s, 4H), 7.90 (s, 4H), 7.73 (s, 4H), 0.37 (s, 18H). $^{13}C$ NMR (101 MHz, $CDCl_3$) δ 134.24, 128.13, 127.55, 124.05, −0.84.

Step 2: Under argon atmosphere, to a solution of 5 (498 mg, 1.0 mmol) in dry $CH_3CN$ (15 ml) was added $BF_4NO$ (394 mg, 3.4 mmol) once at room temperature. After that, the reaction mixture was stirred for 30 min. Then, the reaction was quenched by slowly dropping deoxygenated deionized water (30 mL). The precipitates formed after the quenching were filtered and washed with the deoxygenated deionized water several times and then dried in the dark under vacuum. Samples were stored and handled under $N_2$ atmosphere prior and during experiments. Yield: 367 mg (89%), light yellow solid.

Example 1E

Preparation of Polynitroso Compound VI

Figure 8:
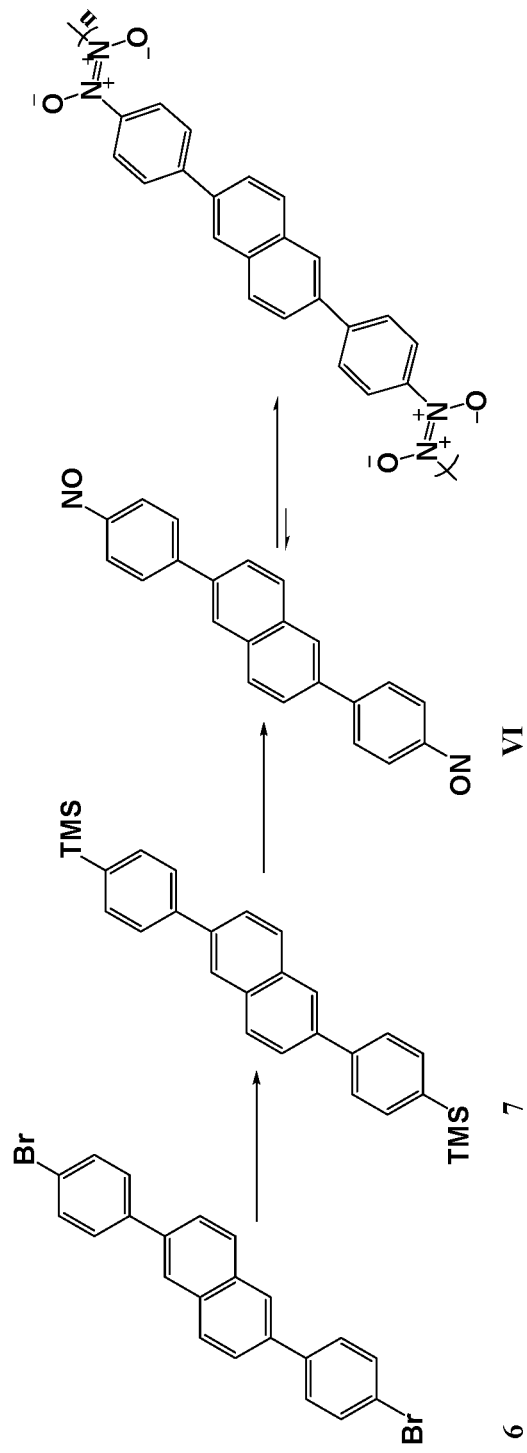
FIG. 8 is a synthetic scheme of polynitroso compound VI.

The synthetic scheme of polynitroso compound V (i.e. the polynitroso compound of Formula (VI) of the present invention) is shown in FIG. 8. Specifically, the preparation comprises two steps.

Step 1: A 500 mL three-neck round-bottom flask equipped with a magnetic stir bar was charged with 2,6-bis(4-bromophenyl)naphthalene 6 (4.35 g, 1 mmol), and dry THF (250 mL). The solution was cooled down to −78° C. A solution of n-butyllithium (2.5 M in hexane, 12 mL, 3 mmol), was added dropwise over 10 min. After that, the reaction mixture was stirred for 30 min. Then, trimethylsilyl chloride (7 mL, 6 mmol) was added dropwise over 5 min and warmed up to RT for 3 hours. The resulting mixture was quenched with water (250 mL), extracted with ethyl acetate (250 mL×2). The organic phase was separated, washed twice with brine, dried over anhydrous $MgSO_4$. The organic phase was concentrated under reduced pressure, and the residue was washed with ethanol several times and dried in vacuum at 50° C. to afford 7 as a white powder (Yield: 3.92 g, 92%). $^1$H NMR (400 MHz, $CDCl_3$) δ 8.08 (s, 1H), 7.98 (d, J=8.4 Hz, 1H), 7.77 (m, 3H), 7.67 (d, J=8.0 Hz, 2H), 0.34 (s, 9H). $^{13}$C NMR (101 MHz, $CDCl_3$) δ 141.39, 139.46, 138.57, 133.94, 132.92, 128.76, 126.70, 125.98, 125.56, -1.04.

Step 2: Under argon atmosphere, to a solution of 7 (424 mg, 1.0 mmol) in dry $CH_3CN$ (15 ml) was added $BF_4NO$ (394 mg, 3.4 mmol) once at room temperature. After that, the reaction mixture was stirred for 30 min. Then, the reaction was quenched by slowly dropping deoxygenated deionized water (30 mL). The precipitates formed after the quenching were filtered and washed with the deoxygenated deionized water several times and then dried in the dark under vacuum. Samples were stored and handled under $N_2$ atmosphere prior and during experiments. Yield: 276 mg (82%), light yellow solid.

Example 1F

Preparation of Polynitroso Compound VII, TPA-3NO

Figure 9:
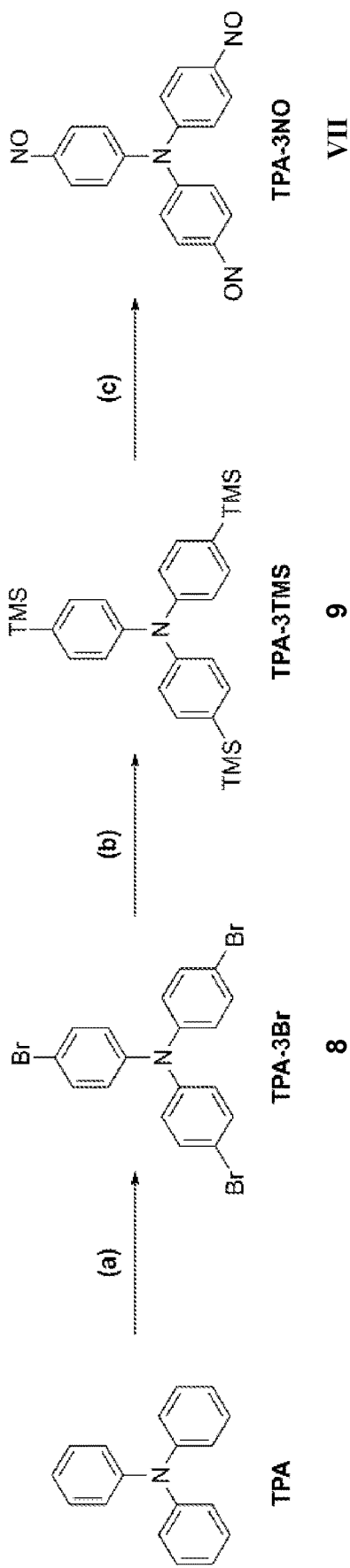
FIG. 9 is a synthetic scheme of polynitroso compound VII.

The synthetic scheme of polynitroso compound VII, TPA-3NO (i.e. the polynitroso compound of Formula (VII) of the present invention) is shown in FIG. 9. Specifically, the preparation comprises three steps.

Step (a): Triphenylamine (TPA) (25 g, 10.5 mmol) and silica gel (100 g) were added to a solution of NBS (56 g, 31.5 mmol, 3 equiv.) in DCM (1000 mL) and the suspension was stirred overnight at room temperature. The silica gel was removed by filtration and the organic phase was washed thoroughly with water and brine followed by drying over $MgSO_4$. Removal of the solvent under reduced pressure yielded tris(4-bromophenyl)amine (TPA-3Br, 8) as white solid (Yield: 45 g, 89%). $^1$H-NMR (400 MHz, $CDCl_3$) δ 7.36 (d, J=8.8 Hz, 6H), 6.92 (d, J=8.8 Hz, 6H). $^{13}$C—NMR (101 MHz, $CDCl_3$): δ=146.2, 132.7, 125.8, 116.2.

Step (b): A 1000 mL three-neck round-bottom flask equipped with a magnetic stir bar was charged with 8 (14.46 g, 3 mmol), and dry THF (600 mL). The solution was cooled down to -78° C. A solution of n-butyllithium (2.5 M in hexane, 54 mL, 13.5 mmol), was added dropwise over 20 min. After that, the reaction mixture was stirred for 30 min. Then, trimethylsilyl chloride (22 mL, 18 mmol) was added dropwise over 5 min and warmed up to RT for 3 hours. The resulting mixture was quenched with water (1000 mL), extracted with ethyl acetate (500 mL×2). The organic phase was separated, washed twice with brine, dried over anhydrous $MgSO_4$. The organic phase was concentrated under reduced pressure, and the residue was washed with ethanol several times and dried in vacuum at 50° C. to afford 4-(trimethylsilyl)-N,N-bis[4-(trimethylsilyl)phenyl]benzenamine (TPA-3TMS, 9) as a white powder (12.6 g, 91% yield). $^1$H NMR (400 MHz, $CDCl_3$) δ 7.41 (d, J=8.2 Hz, 2H), 7.11 (d, J=8.2 Hz, 2H), 0.29 (s, 9H). $^{13}$C NMR (101 MHz, $CDCl_3$) δ 148.13, 134.45, 134.11, 123.58, -0.77.

Step (c): Under argon atmosphere, to a solution of 9 (600 mg, 1.3 mmol) in dry $CH_3CN$ (42 ml, 0.03M) was added $BF_4NO$ (682 mg, 5.85 mmol) once at room temperature. After that, the reaction mixture was stirred for 30 min. Then, the reaction was quenched by slowly dropping deoxygenated deionized water (42 mL). The precipitates formed after the quenching were filtered and washed with the deoxygenated deionized water several times and then dried in the dark under vacuum. Samples (i.e., tris(4-nitrosophenyl)amine, TPA-3NO) were stored and handled under $N_2$ atmosphere prior and during experiments. The above synthetic procedure is believed to be minimizing exposure and oxidation to the ambient. Yield: 400 mg (92.6%), brown solid. $^1$H NMR (400 MHz, $CDCl_3$) δ 7.92 (d, J=8.7 Hz, 6H), 7.36 (d, J=9.0 Hz, 6H). $^{13}$C NMR (101 MHz, $CDCl_3$) δ 163.04, 151.37, 124.91, 123.54. HRMS $C_{18}H_{12}N_4O_3$ (M+H), Calculated mass: 333.09822, Found 333.09780.

Example 1G

Preparation of Polynitroso Compound VIII

Figure 10:
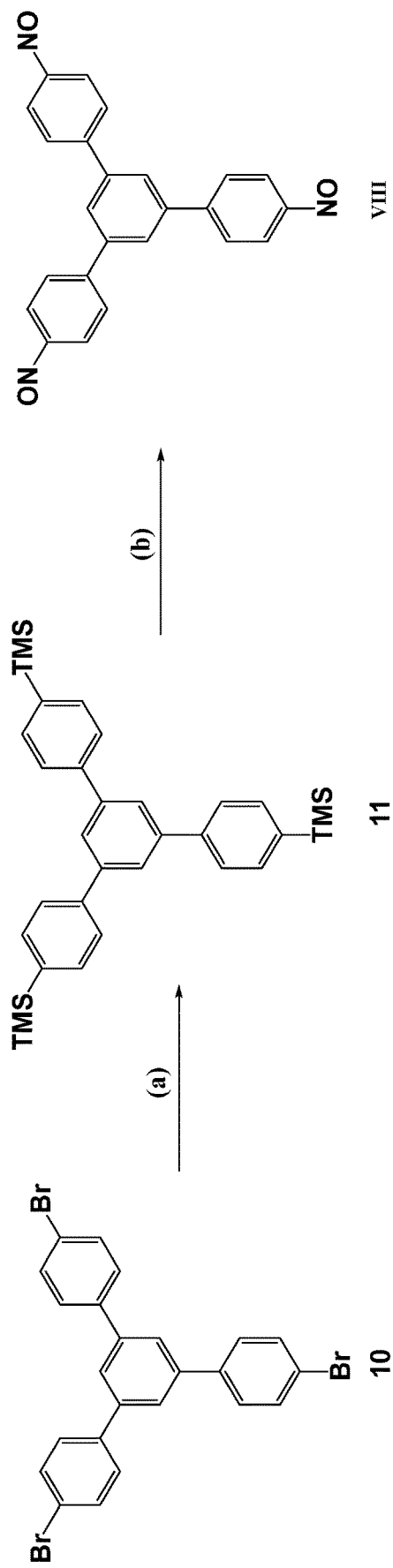
FIG. 10 is a synthetic scheme of polynitroso compound VIII (i.e., the polynitroso compound of Formula (VII) of the present invention, TPA-3NO).

The synthetic scheme of polynitroso compound VIII (i.e. the polynitroso compound of Formula (VIII) of the present invention) is shown in FIG. 10. Specifically, the preparation comprises two steps.

Step (a): A 1000 mL three-neck round-bottom flask equipped with a magnetic stir bar was charged with 1,3,5-tris(4-bromophenyl)benzene 10 (16 g, 3 mmol), and dry THF (600 mL). The solution was cooled down to -78° C. A solution of n-butyllithium (2.5 M in hexane, 54 mL, 13.5 mmol), was added dropwise over 20 min. After that, the reaction mixture was stirred for 30 min. Then, trimethylsilyl chloride (22 mL, 18 mmol) was added dropwise over 5 min and warmed up to RT for 3 hours. The resulting mixture was quenched with water (1000 mL), extracted with ethyl acetate (500 mL×2). The organic phase was separated, washed twice with brine, dried over anhydrous $MgSO_4$. The organic phase was concentrated under reduced pressure, and the residue was washed with ethanol several times and dried in vacuum at 50° C. to afford 11 as a white powder (Yield: 14 g, 90%). $^1$H NMR (300 MHz, $CDCl_3$) δ 7.79 (s, 3H), 7.71-7.62 (m, 12H), 0.33 (s, 27H). $^{13}$C NMR (101 MHz, $CDCl_3$) δ 142.49, 141.70, 139.80, 134.11, 126.87, 125.46, 77.52, 77.20, 76.88, -0.86.

Step (b): Under argon atmosphere, to a solution of 11 (200 mg, 0.38 mmol) in dry $CH_3CN$ (12 ml) was added $BF_4NO$ (227 mg, 1.95 mmol) once at room temperature. After that, the reaction mixture was stirred for 30 min. Then, the reaction was quenched by slowly dropping the deoxygenated deionized water (12 mL). The precipitates formed after quenching were filtered and washed with the deoxygenated deionized water several times and then dried in the dark under vacuum. Samples were stored and handled under $N_2$ atmosphere prior and during experiments. Yield: 140 mg (93%), green solid. $^1$H NMR (300 MHz, DMSO-$d_6$) δ 8.39 (d, J=8.5 Hz, 2H), 8.37 (s, 1H), 8.11 (d, J=8.3 Hz, 2H).

Example 1H

Preparation of Polynitroso Compound X

Figure 11:
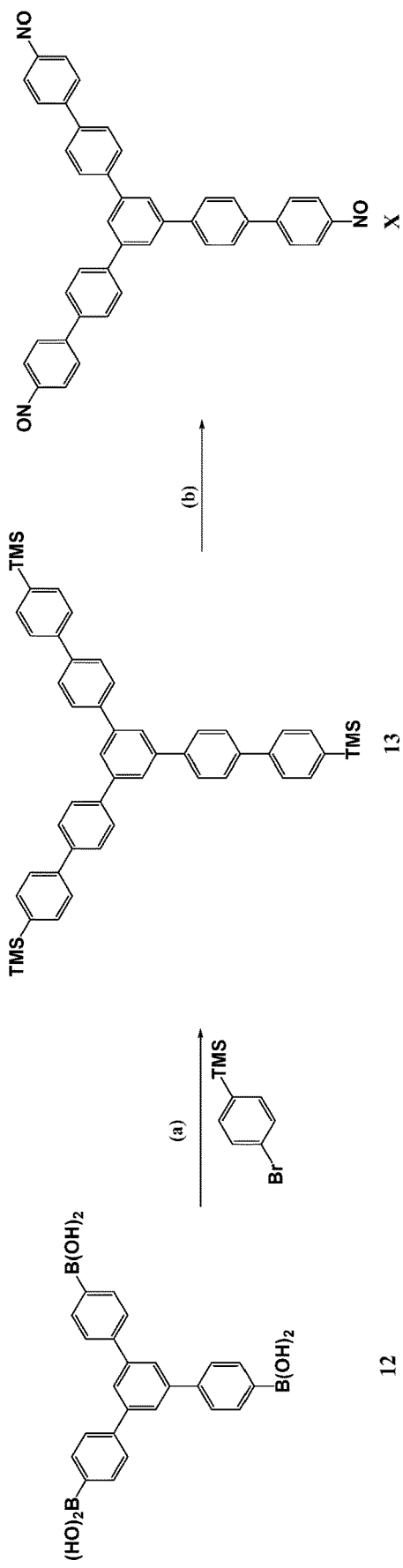
FIG. 11 is a synthetic scheme of polynitroso compound X.

The synthetic scheme of polynitroso compound X (i.e. the polynitroso compound of Formula (X) of the present invention) is shown in FIG. 11. Specifically, the preparation comprises two steps.

Step (a): Commercially available 1,3,5-Tris (4-bromophenyl) benzene 12 (5.0 g, 11.42 mmol) was dissolved in 250 mL of solvent (THF/Toluene, (v/v): 1:1). Then 1-bromo-4-(trimethylsilyl)benzene (9.4 g, 41 mmol), $PdCl_2(PPh_3)_2$ (961 mg, 12 mol %), and a solution of $K_2CO_3$ (9.7 g, 61.5 mmol) in 20 mL of distilled water were added to it. The reaction mixture was refluxed at 110° C. for 40 hours and then quenched with water and extracted with dichloromethane thrice. The combined organic layer was then dried over MgSO$_4$. After evaporation of solvent the crude product was purified by flash chromatography with hexanes as the eluent to obtain 6.9 g of pure compound 13 as a colorless solid (unstable under UV (254/365 nm) light), yield 81%. $^1$H NMR (400 MHz, CDCl$_3$) δ 7.90 (s, 3H), 7.81 (d, J=8.4 Hz, 6H), 7.76 (d, J=8.4 Hz, 6H), 7.69 (d, J=1.8 Hz, 12H), 0.37 (s, 27H). $^{13}$C NMR (101 MHz, CDCl$_3$) δ 142.09, 141.14, 140.51, 140.20, 139.63, 134.09, 127.90, 127.77, 126.57, 125.15, −0.87.

Step (b): Under argon atmosphere, to a solution of 13 (200 mg, 0.26 mmol) in dry CH$_3$CN (10 ml) was added BF$_4$NO (158 mg, 1.36 mmol) once at room temperature. Then, the reaction mixture was stirred for 30 min. After that, the reaction was quenched by slowly dropping deoxygenated deionized water (10 mL). The precipitates formed after quenching were filtered and washed with the deoxygenated deionized water several times and then dried in the dark under vacuum. Samples were stored and handled under N$_2$ atmosphere prior and during experiments. Yield: 160 mg (96%), green solid.

Example 1I

Preparation of Polynitroso Compound XI

Figure 12:
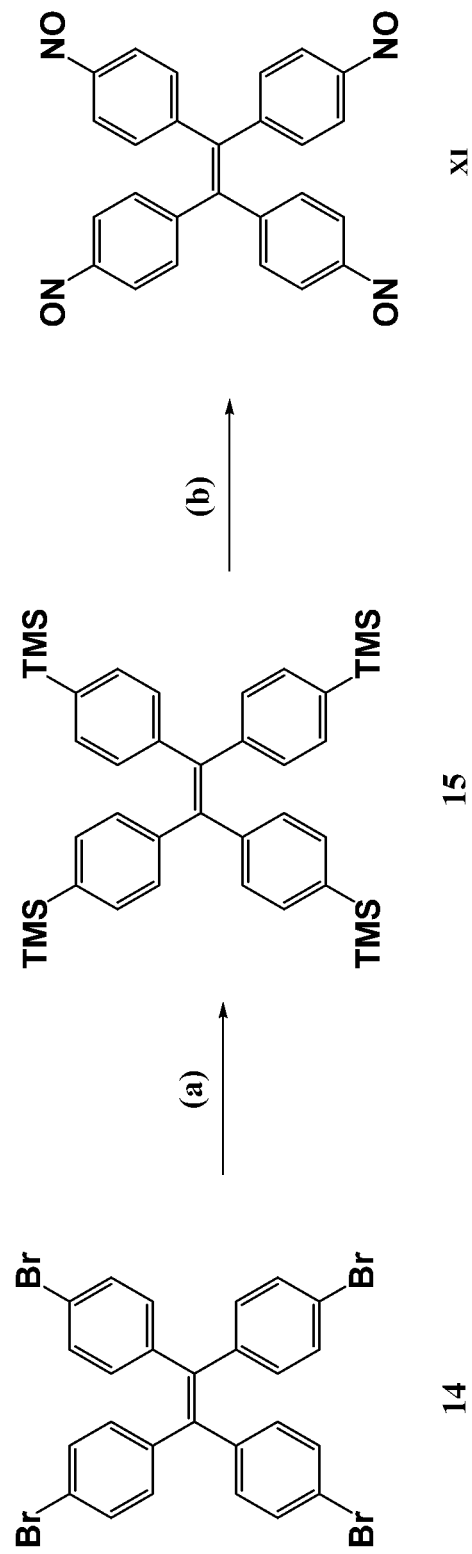
FIG. 12 is a synthetic scheme of polynitroso compound XI.
Figure 13A:
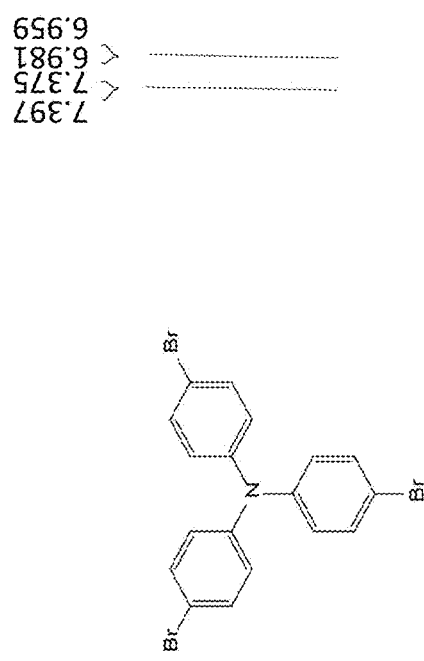
FIG. 13A is a $^1$H-nuclear magnetic resonance (NMR) spectrum of TPA-3Br prepared in accordance with an embodiment of the present invention.
Figure 13A:
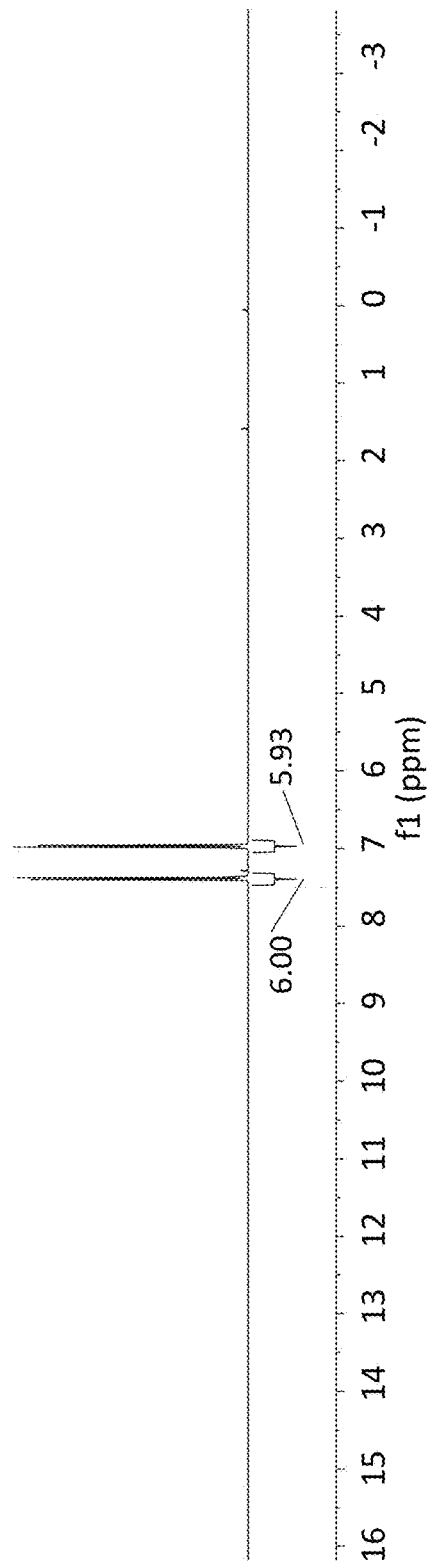
Figure 13B:
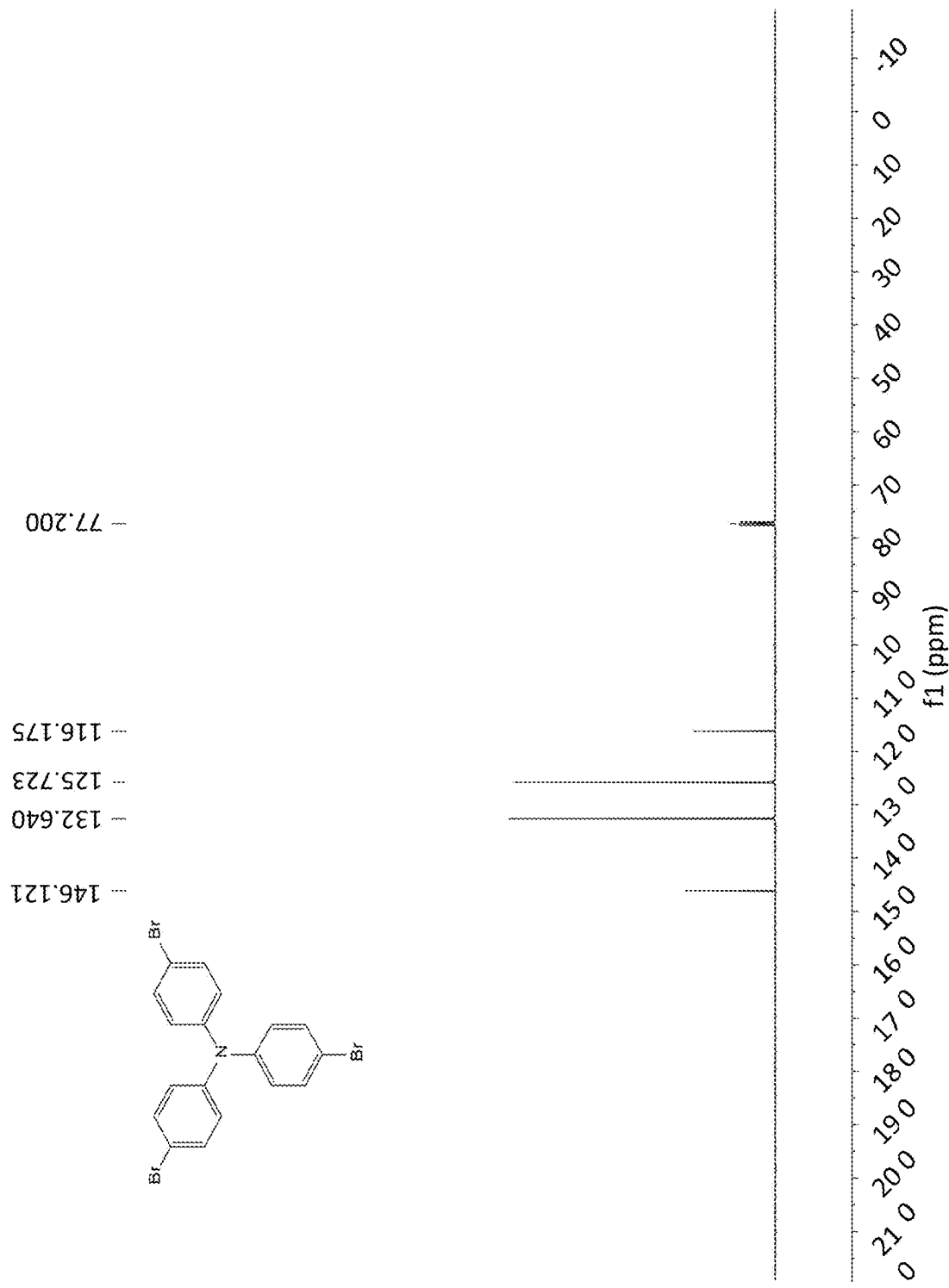
FIG. 13B is a $^{13}$C-NMR spectrum of TPA-3Br prepared in accordance with an embodiment of the present invention.
Figure 14A:
FIG. 14A is a $^1$H-NMR spectrum of TPA-3TMS prepared in accordance with an embodiment of the present invention.
Figure 14B:
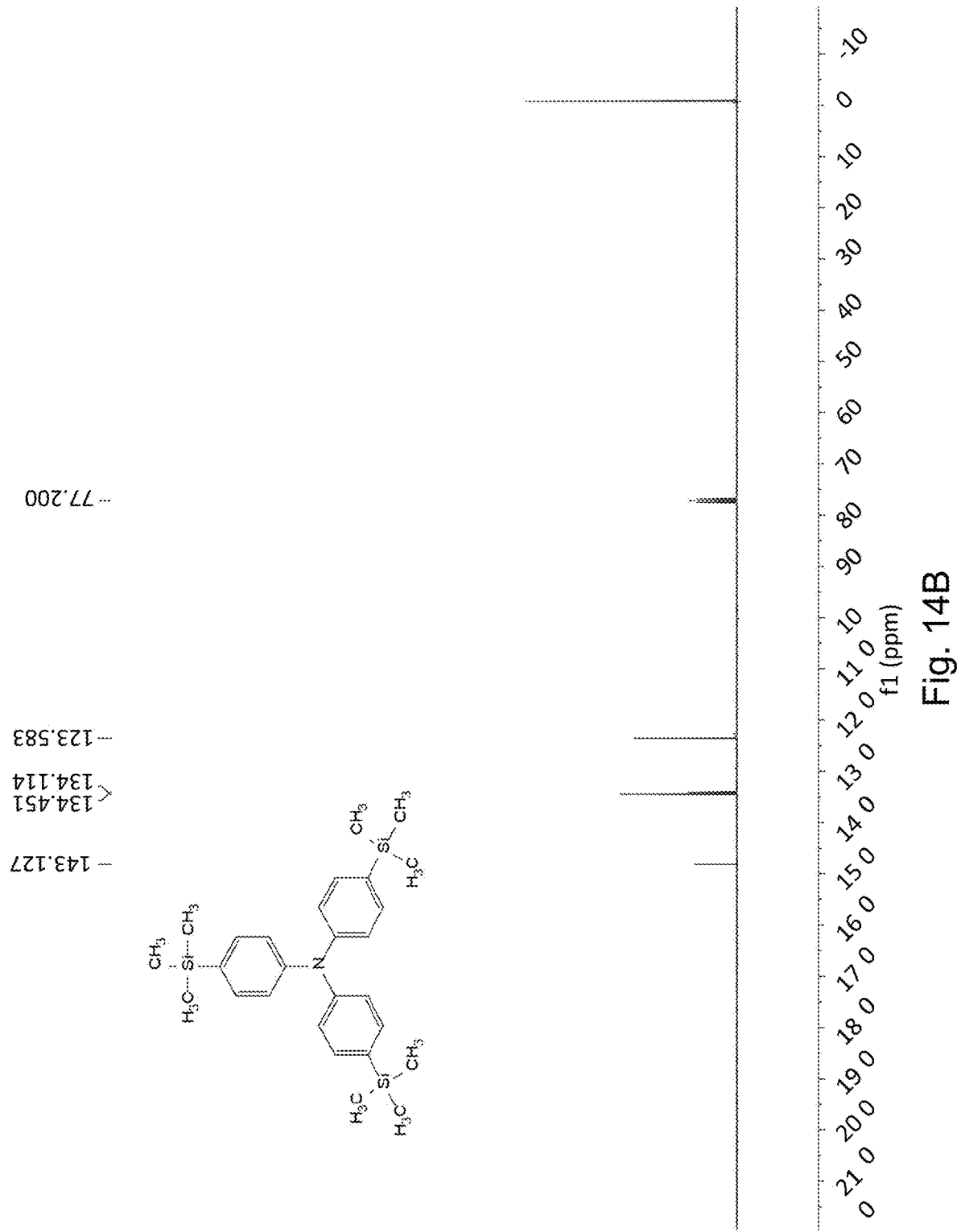
FIG. 14B is a $^{13}$C-NMR spectrum of TPA-3TMS prepared in accordance with an embodiment of the present invention.
Figure 15A:
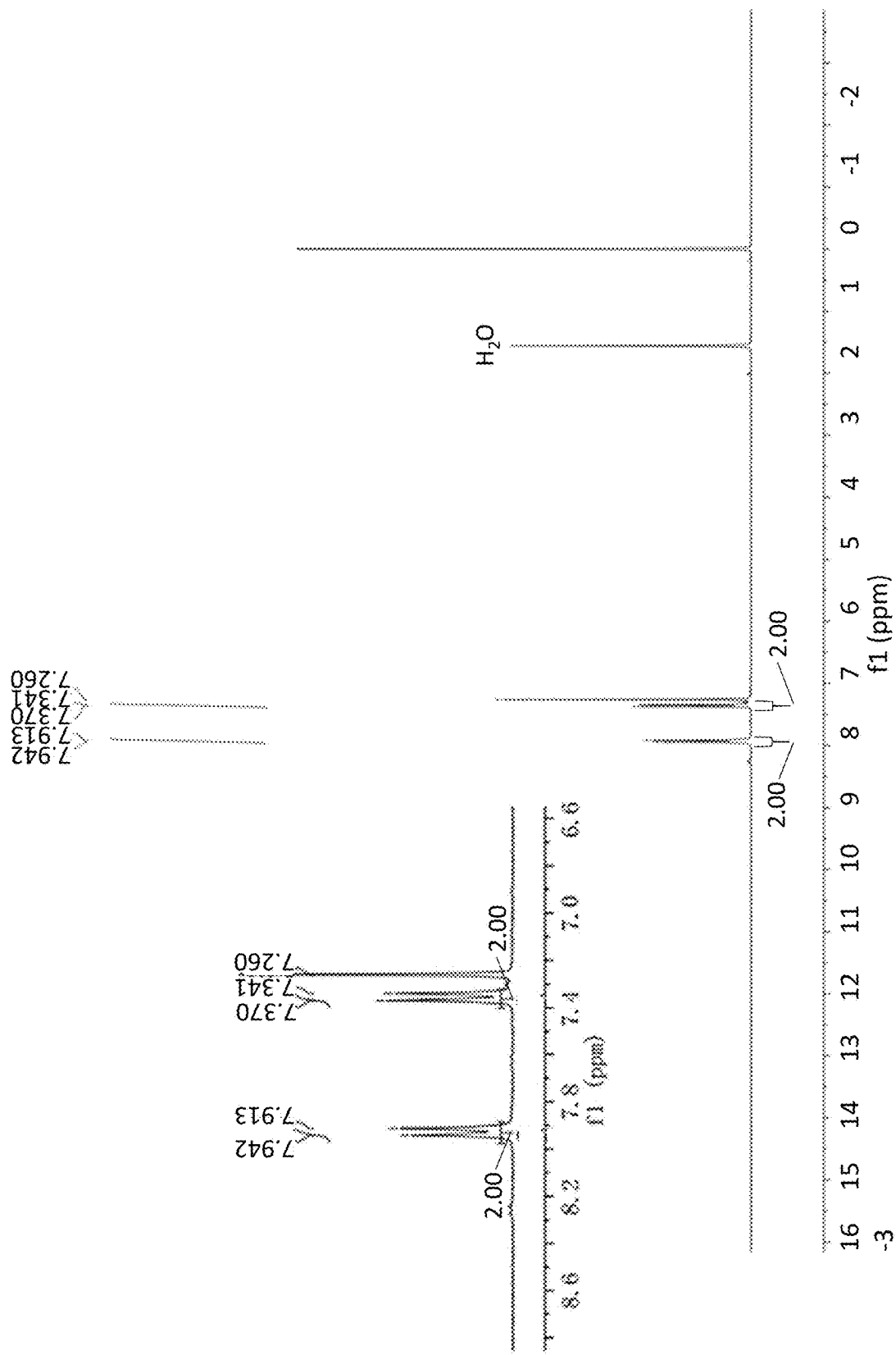
FIG. 15A is a $^1$H-NMR spectrum of TPA-3NO prepared in accordance with an embodiment of the present invention. The insert is the enlarged spectrum of about 6.6 to about 8.6 ppm.
Figure 15B:
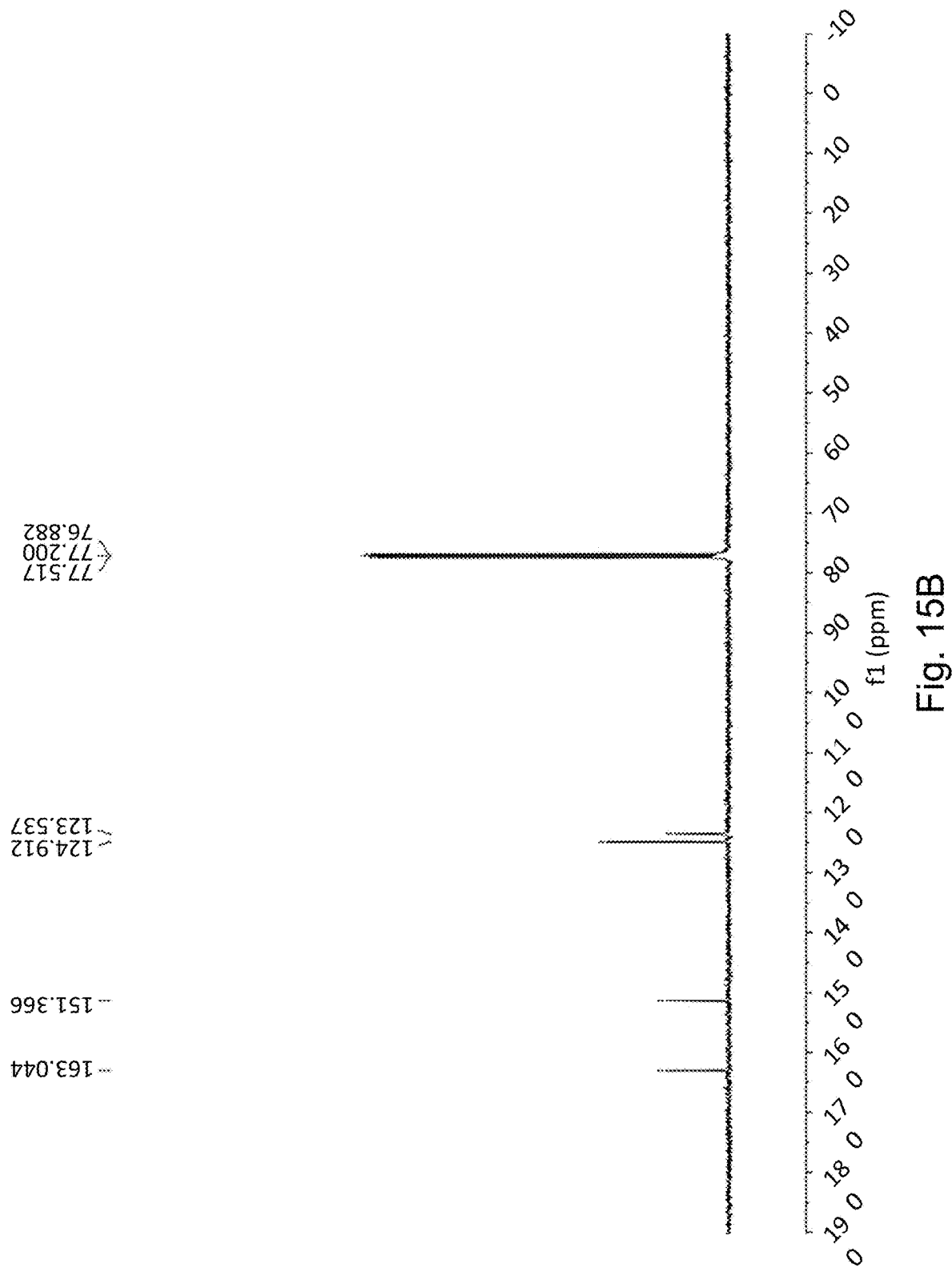
FIG. 15B is $^{13}$C-NMR spectrum of TPA-3NO prepared in accordance with an embodiment of the present invention.

The synthetic scheme of polynitroso compound XI (i.e. the polynitroso compound of Formula (XI) of the present invention) is shown in FIG. 12. Specifically, the preparation comprises two steps.

Step (a): A 2000 mL three-neck round-bottom flask equipped with a magnetic stir bar was charged with 1,1,2,2-tetrakis(4-bromophenyl)ethylene 14 (19.3 g, 3 mmol), and dry THF (1000 mL). The solution was cooled down to −78° C. A solution of n-butyllithium (2.5 M in hexane, 72 mL, 18 mmol), was added dropwise over 20 min. After that, the reaction mixture was stirred for 30 min. Then, trimethylsilyl chloride (29 mL, 24 mmol) was added dropwise over 5 min and warmed up to RT for 3 hours. The resulting mixture was quenched with water (1000 mL), extracted with ethyl acetate (500 mL×2). The organic phase was separated, washed twice with brine, dried over anhydrous MgSO$_4$. The organic phase was concentrated under reduced pressure, and the residue was washed with ethanol several times and dried in vacuum at 50° C. to afford 15 as a white powder (16 g, 86% yield). $^1$H NMR (400 MHz, CDCl$_3$) δ 7.24 (d, J=7.9 Hz, 2H), 7.00 (d, J=7.9 Hz, 2H), 0.22 (s, 9H). $^{13}$C NMR (101 MHz, CDCl$_3$) δ 144.24, 141.38, 138.32, 132.65, 130.73, −0.93.

Step (b): Under argon atmosphere, to a solution of 15 (200 mg, 0.32 mmol) in dry CH$_3$CN (10.7 ml) was added BF$_4$NO (252 mg, 2.1 mmol) once at room temperature. Then, the reaction mixture was stirred for 30 min. After that, the reaction was quenched by slowly dropping deoxygenated deionized water (12 mL). The precipitates formed after quenching were filtered and washed with the deoxygenated deionized water several times and then dried in the dark under vacuum. Samples were stored and handled under N$_2$ atmosphere prior and during experiments. Yield: 120 mg (83%), yellow-green solid. $^1$H NMR (300 MHz, DMSO-d6) δ 7.82 (d, J=8.5 Hz, 1H), 7.47 (d, J=8.5 Hz, 1H). $^{13}$C NMR (101 MHz, DMSO-d6) δ 163.97, 148.87, 142.09, 132.45, 120.83.

Example 2

Characterization of Polynitroso Compound VII, TPA-3NO

Figure 16:
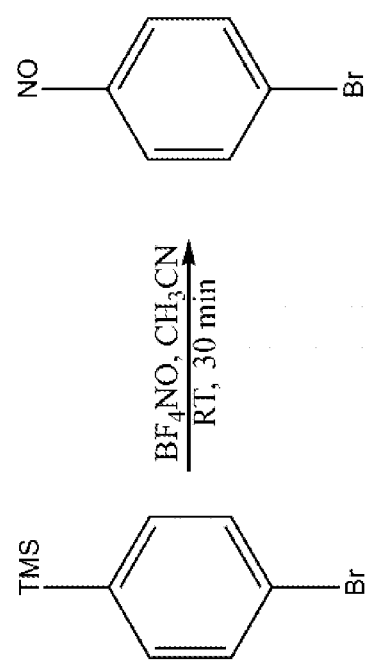
FIG. 16 is a synthetic scheme of 1-bromo-4-nitrosobenzene.
Figure 17A:
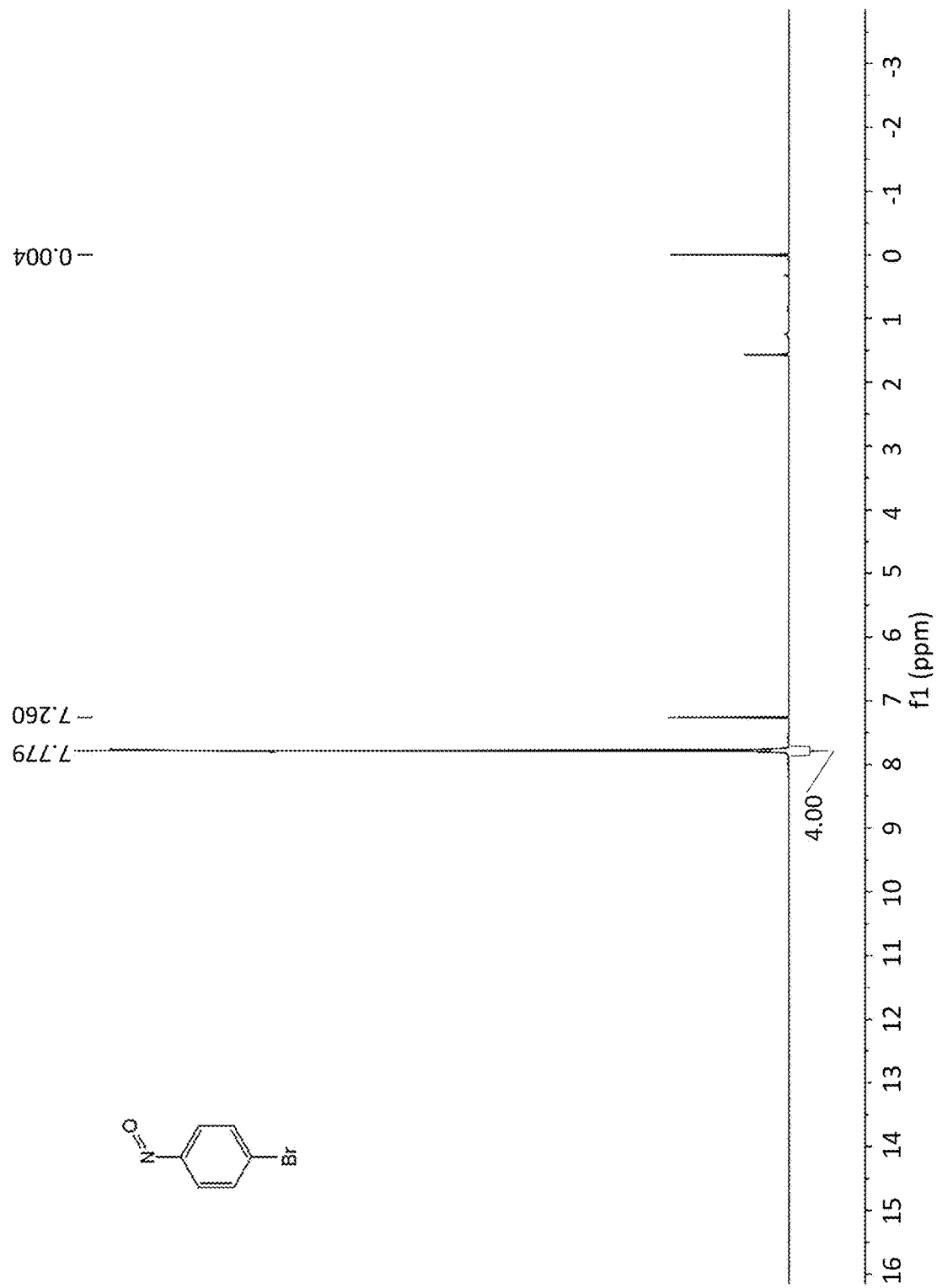
FIG. 17A is a $^1$H-NMR spectrum of (4-bromophenyl)trimethylsilane.
Figure 17B:
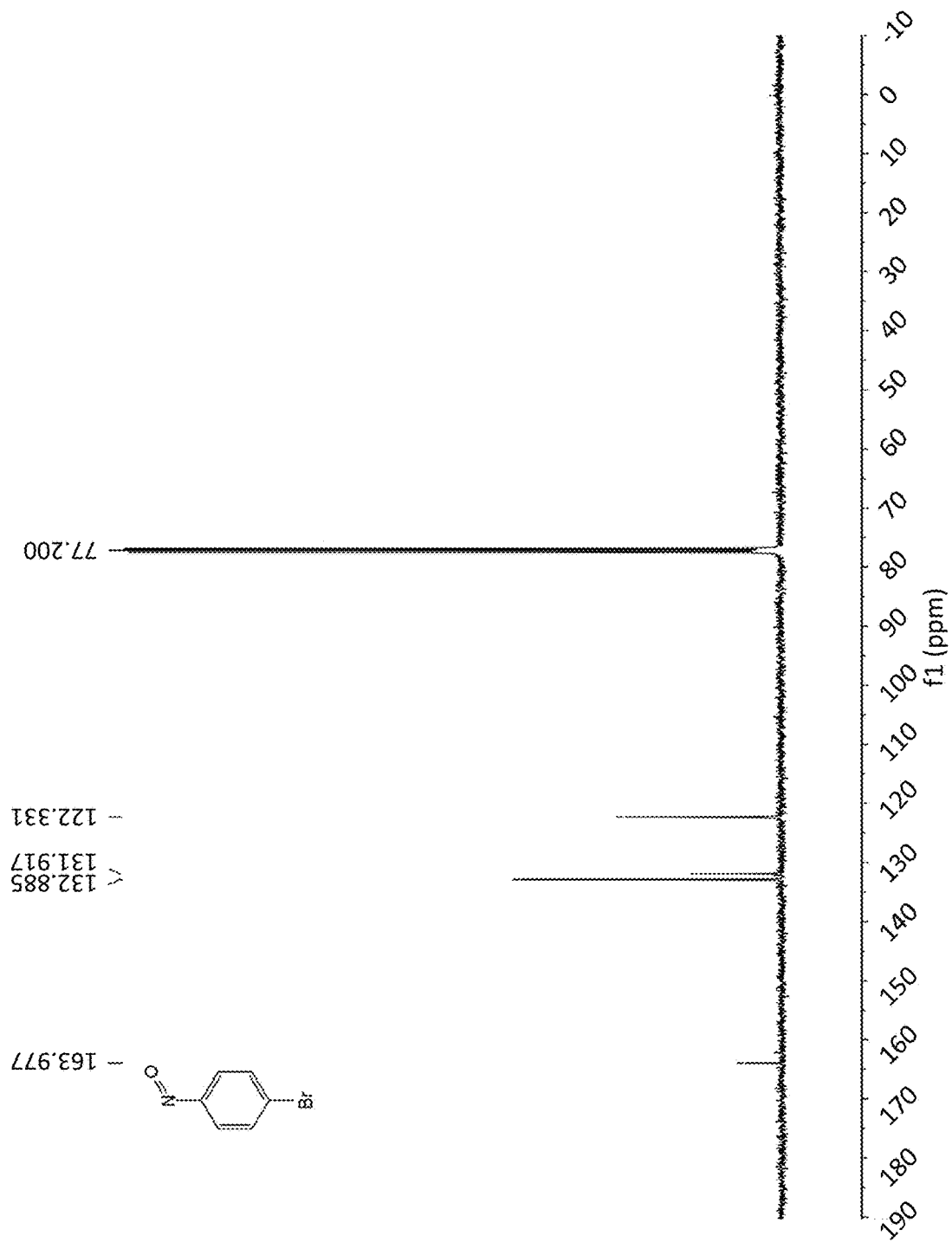
FIG. 17B is a $^{13}$C-NMR spectrum of (4-bromophenyl)trimethylsilane.

The synthesis of TPA-3NO (i.e., the polynitroso compound of Formula (VII)) was commenced with the preparation of intermediate TPA-3Br by the bromination of TPA at room temperature for 12 hours (FIG. 9). The treatment of TPA-3Br with n-BuLi under −78° C., followed by the addition of trimethylsilyl chloride, formed the key intermediate of TPA-3TMS with a yield of 91%. Then, the targeting product of TPA-3NO can be readily prepared by nitrosating intermediate of TPA-3TMS with BF$_4$NO in quantitative yields. The as-obtained light brown solid showed high purity after a simple work-up procedure as detailed in Example 1F, which had been confirmed by nuclear magnetic resonance (NMR) spectra (FIGS. 13A to 15B). For subsequent comparison studies, 1-bromo-4-nitrosobenzene was prepared in the same way (FIG. 16). NMR spectra of the as-prepared 1-bromo-4-nitrosobenzene are shown in FIGS. 17A to 17B. $^1$H NMR (400 MHz, CDCl$_3$) δ 7.79 (s, 4H); $^{13}$C NMR (101 MHz, CDCl$_3$) δ 163.97, 132.85, 131.97, 122.33.

Figure 18A:
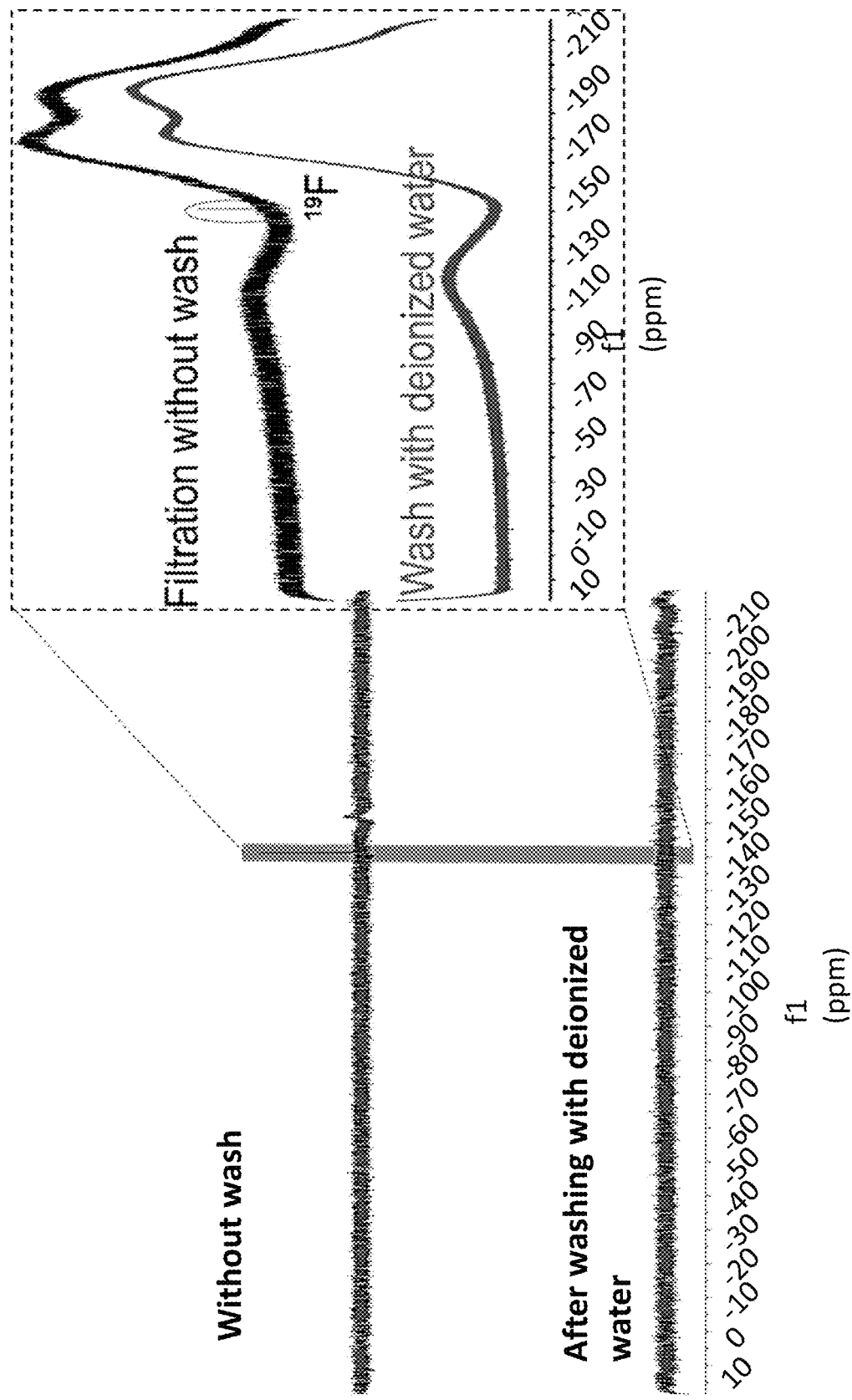
FIG. 18A is a $^{19}$F-NMR spectra of TPA-3NO prepared in accordance with an embodiment of the present invention, with or without washed with deionized water. The insert is an enlarged portion of the highlighted part of the spectra. The absence of $^{19}$F signals indicating that no inorganic residue is present in the resultant TPA-3NO.
Figure 18B:
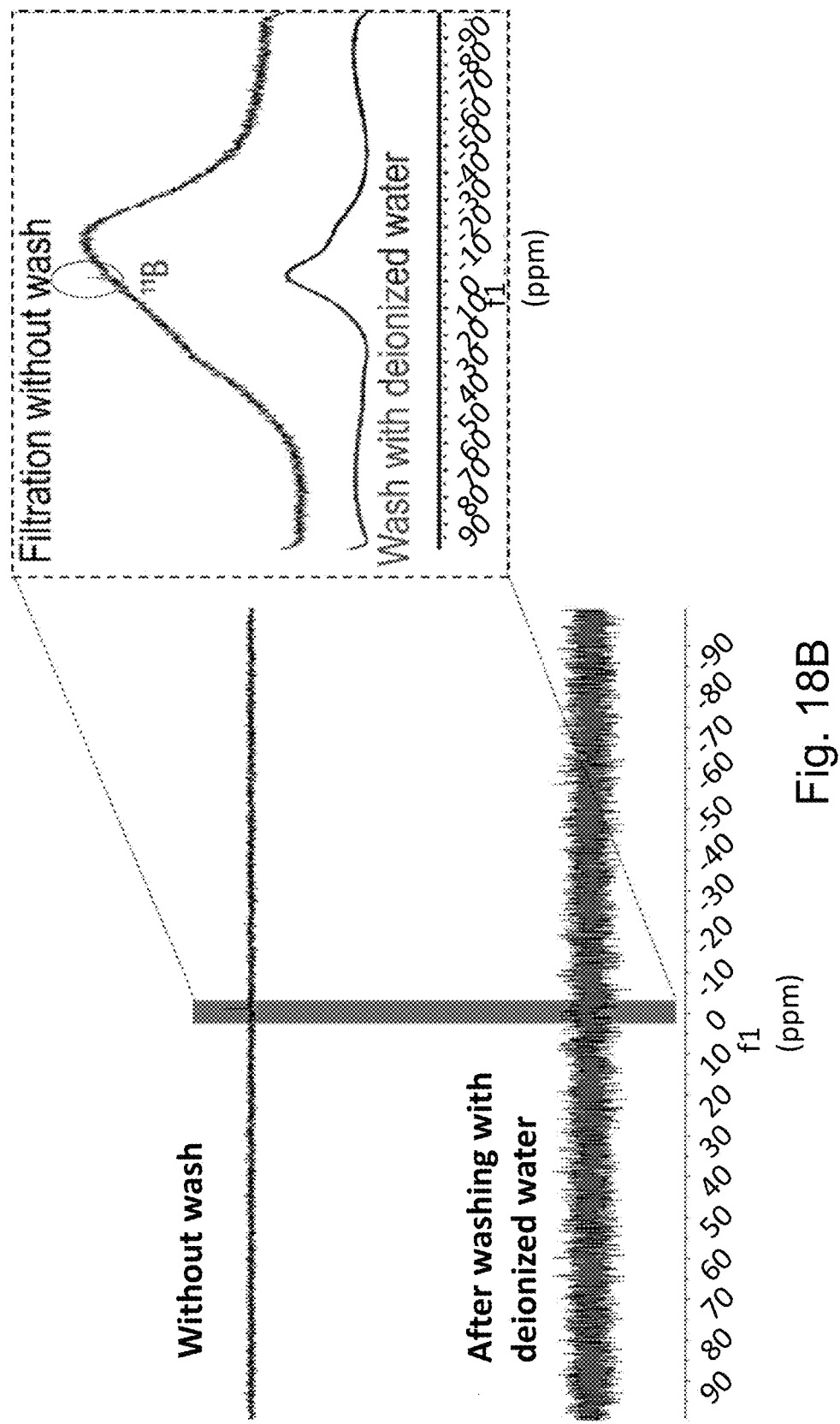
FIG. 18B is a $^{11}$B-NMR spectra of TPA-3NO prepared in accordance with an embodiment of the present invention, with or without washed with deionized water. The insert is an enlarged portion of the highlighted part of the spectra. The absence of $^{11}$B signals indicating that no inorganic residue is present in the resultant TPA-3NO.
Figure 19:
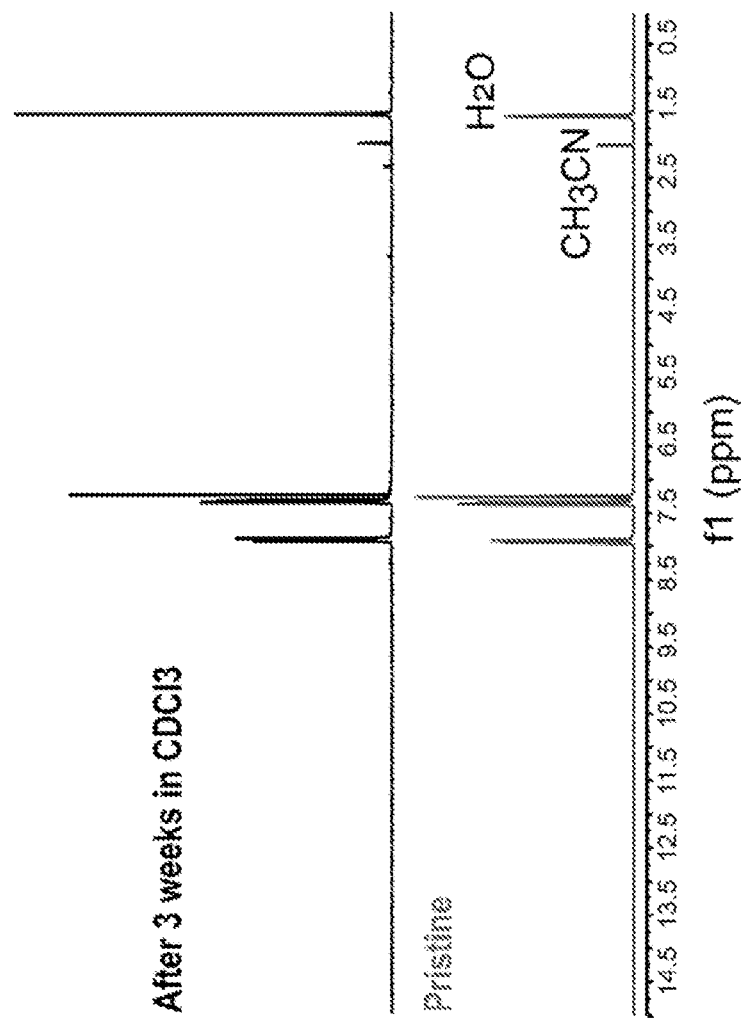
FIG. 19 is a $^1$H-NMR spectrum of TPA-3NO in CDCl$_3$ before and after 3 weeks.
Figure 20:
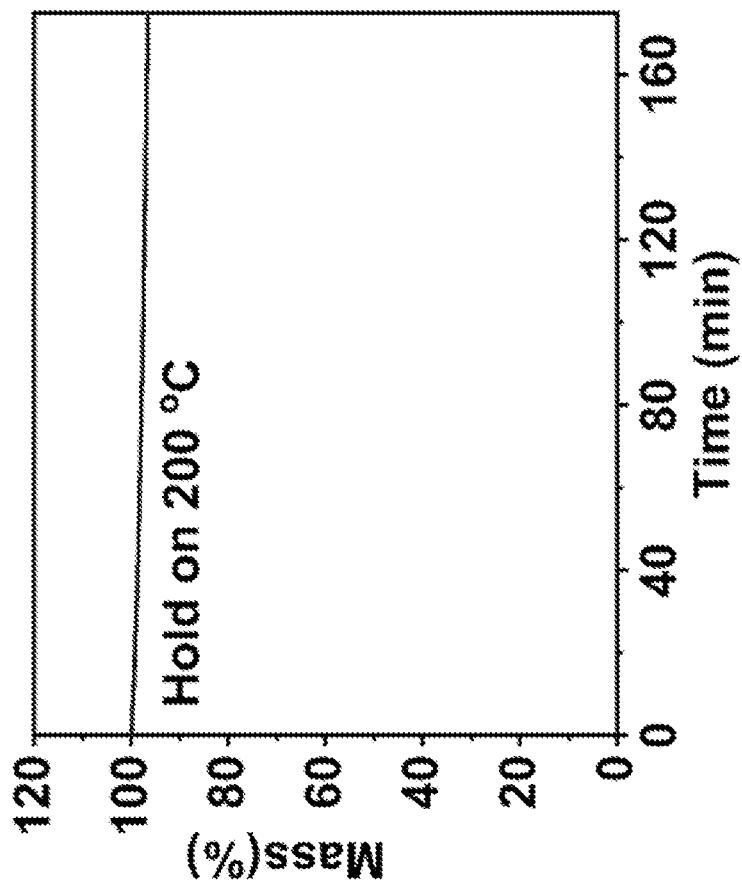
FIG. 20 is a plot of weight against time under 200° showing the thermogravimetric analysis (TGA) result of TPA-3NO.

As evidenced by the $^9$F and $^{11}$B NMR spectra shown in FIGS. 18A and 18B, even after a long time scanning, no inorganic residues were observed. In addition, as illustrated in FIG. 19, the nitroso groups on TPA-3NO showed substantial stability and could persist in solvent for a few weeks without noticeable decomposition. Thermogravimetric analysis (TGA) also indicates that TPA-3NO can be stabilized at 200° C. for 180 minutes with less than 5% weight loss (FIG. 20).

The form (i.e., monomeric/dimeric/oligomeric/polymeric) of which TPA-3NO exists was determined by UV-Visible (UV-Vis) spectroscopy, Fourier-transform infrared (FT-IR) spectroscopy, and single-crystal X-ray Diffraction (SCXRD). The UV-Vis absorption spectra of TPA-3NO were recorded in a diluted chloroform solution ($10^{-5}$ M, FIG. 21A) as well as in films (FIG. 21B). The maximum absorbance around 440 nm in chloroform is the characteristic of the π*←n$_N$ absorption of nitroso monomer. The absorption bands at 256 and 274 nm correspond to the π*←n$_O$ and π*←π transitions of nitroso groups. The optical bandgap based on the onset absorption in the film is calculated to be $E_g^{opt}$=2.27 eV.

Figure 21C:
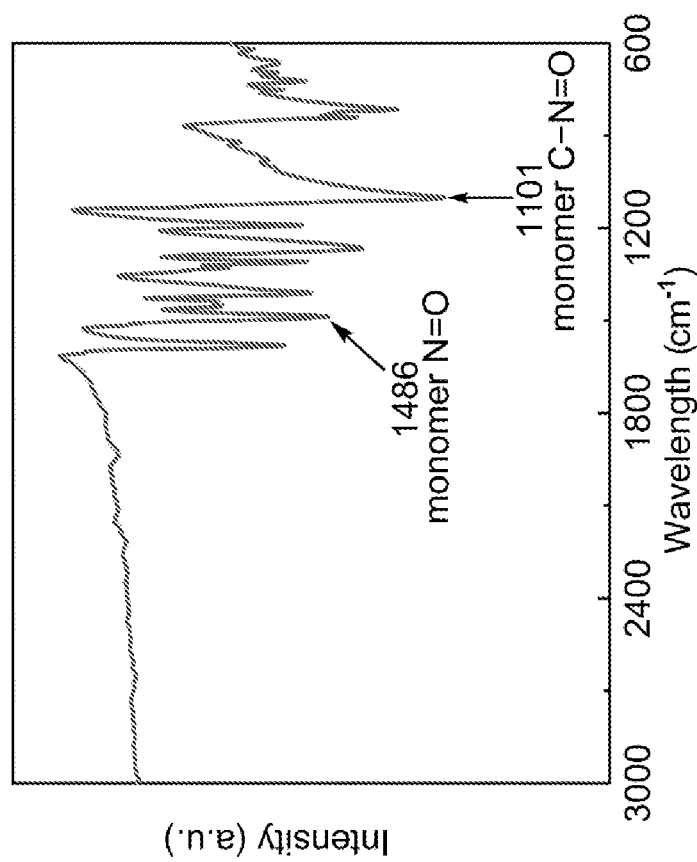
FIG. 21C is a FT-IR spectrum of TPA-3NO.

The monomeric structural feature of TPA-3NO was further confirmed by FT-IR analysis. As shown in FIG. 21C, the characteristic absorption peak at 1486 cm$^{-1}$ is attributed to the monomeric nitroso group. The strongest signal at 1101 cm$^{-1}$, which is generally appeared in the FT-IR spectra of multi-nitroso compounds, can be attributed to the C—N═O stretching vibration of the monomer. Meanwhile, the intensive bands at 1266 cm$^{-1}$ (due to vibrations of the core N—C(sp$^2$) stretching) and the intense vibrations at 1581 cm$^{-1}$ together with a shoulder peak near 1486 cm$^{-1}$ were attributed to the phenyl rings of TPA-3NO.

Figure 21D:
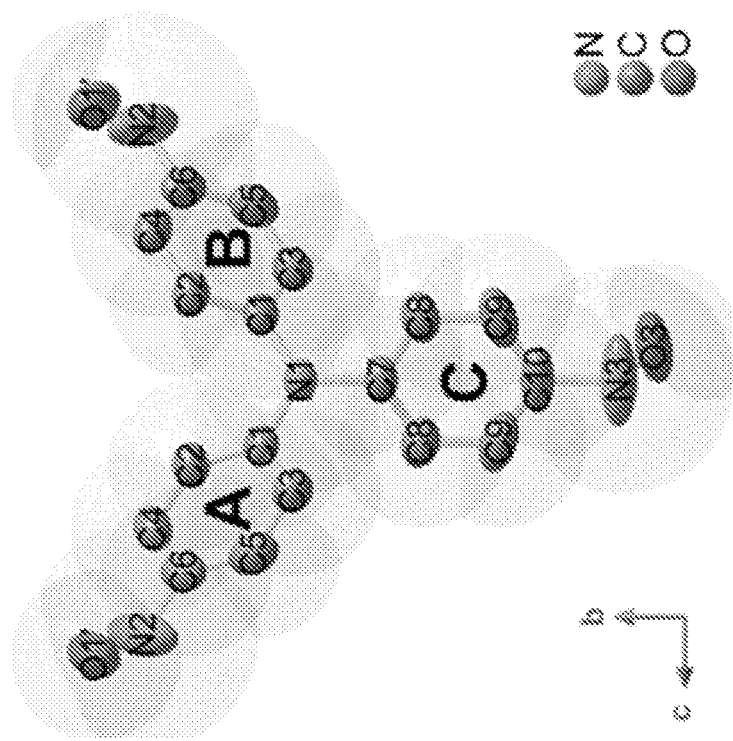
FIG. 21D is a solid-state structure of TPA-3NO resolved by SCXRD analysis (CCDC Number: 2207880).

The suitable single crystals of TPA-3NO for SCXRD analysis were readily obtained through the evaporation of its chloroform solution. As shown in FIG. 21D, the single crystal structure indicates that N1 is in the plane of C1C1C7, from which the three p-phenylene rings A, B, and C are tilted by about 32.1°, about 32.1°, and about 46.1°, respectively. The bond lengths on the benzene rings are in the range of about 1.37-1.39 Å and the bonds connecting the nitroso groups with the benzene rings are in the range of about 1.41-1.42 Å. However, the N═O bonds in the nitroso groups are about 0.97-0.98 Å, which are significantly shorter than those of the formal lengths in nitroso compounds (about 1.2-1.3 Å), suggesting the distinct characters of nitroso groups in TPA-3NO.

Figure 21F:
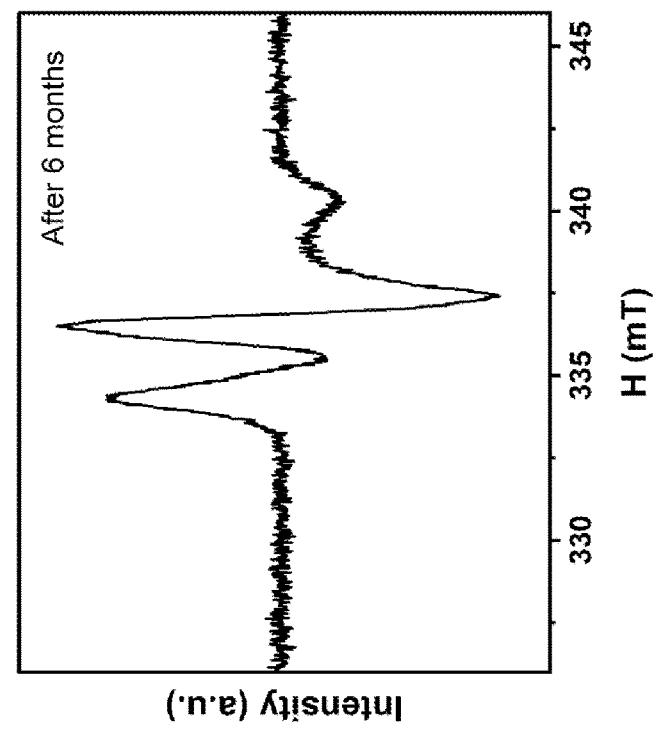
FIG. 21F is an EPR spectrum of TPA-3NO powders under ambient atmosphere for 6 months.
Figure 21E:
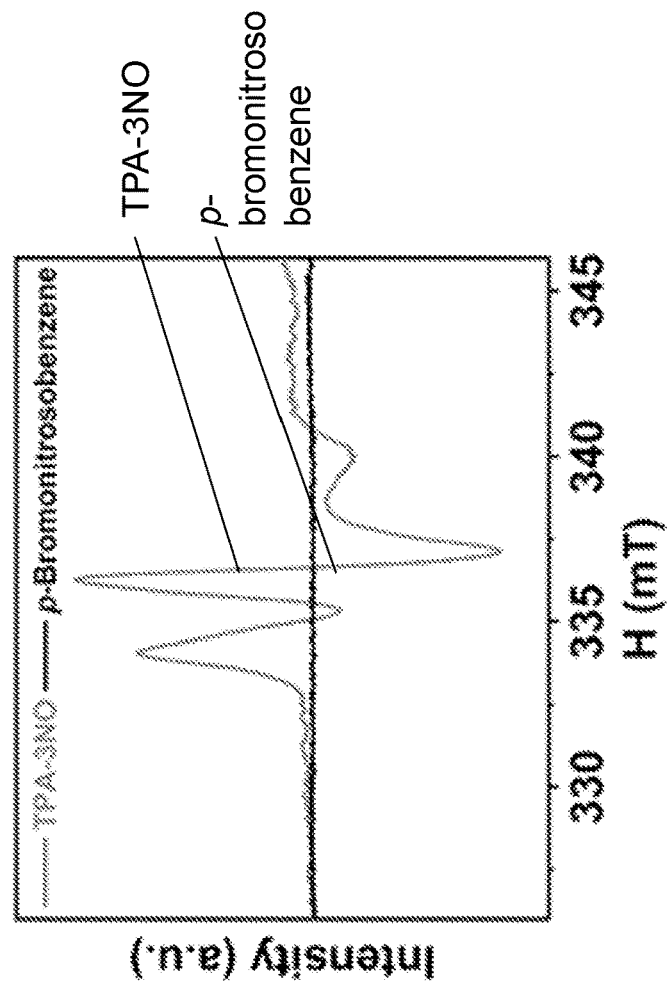
FIG. 21E is an EPR spectra of TPA-3NO and 1-bromo-4-nitrosobenzene powder samples.

It is believed that nitroso group is a powerful electron-withdrawing substitute, whereas triphenylamine (TPA) moiety is an electron-donating substituent, thus, it is believed that TPA-3NO would be a donor-acceptor (D-A) molecule with strong captodative effect (i.e., stabilization of radicals by a synergistic effect of an electron-withdrawing substituent and an electron-donating substituent). To investigate the electronic behavior of TPA-3NO, electron paramagnetic resonance (EPR) analysis was conducted. As shown in FIG. 21E, TPA-3NO showed intense signals in the EPR spectrum, with the g value being about 2.0051. It is believed that mono-nitroso molecules would never show any evidence in respect of the existence of free radicals. Meanwhile, it is noted that the comparing molecule 1-bromo-4-nitrosobenzene, which was prepared by the same way as TPA-3NO as mentioned above, showed negligible EPR signal (FIG. 21E). Given that there were no $^{19}$F and $^{11}$B-NMR signals were observed in FIGS. 18A and 18B, which indicates that counterions are absent in the as-prepared solid, it is believed that the neutral radical signals in FIG. 21E originate from the intrinsic character of the highly pure TPA-3NO.

Figure 22:
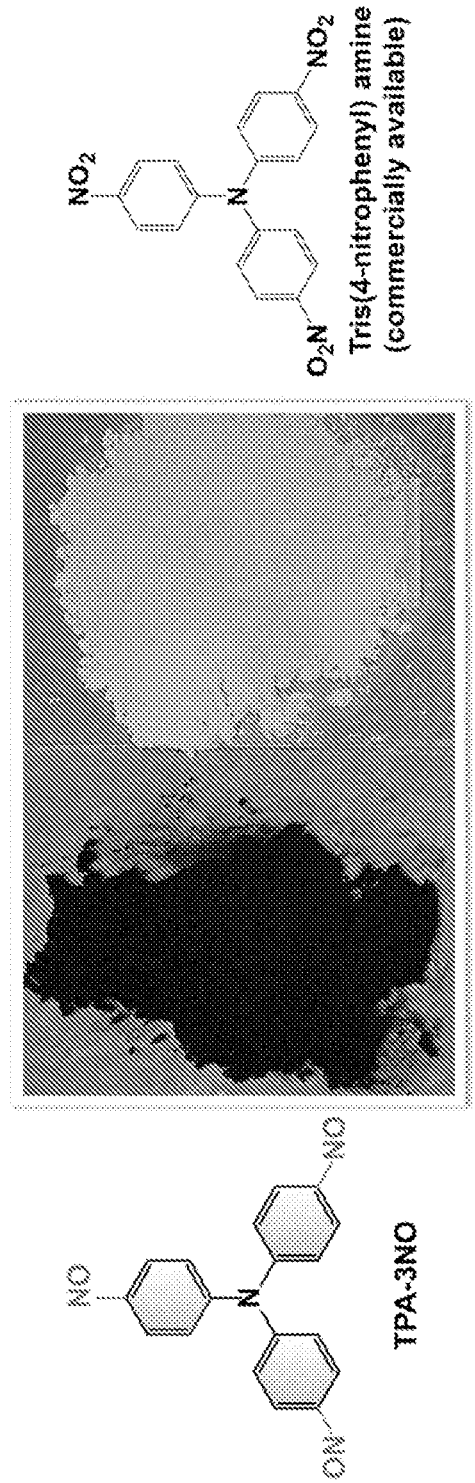
FIG. 22 is a photo showing the fluorescence between TPA-3NO and commercially available tris(4-nitrophenyl) amine excited by 365 nm light.

The radical character of TPA-3NO is further supported by its non-fluorescence, which is believed to be a consequence of excitons quenching by the unpaired electrons (FIG. 22). Unexpectedly, the inventors found that the radical of TPA-3NO shows substantial persistence in ambient atmosphere, even 6 months passed, the radical nature still retained (FIG. 21F). In view of the outstanding stability of the structure and the persistence of the radical feature, it is believed that TPA-3NO would be a promising candidate for rechargeable battery applications (e.g., Li-ion battery (LIBs), organic radical battery (ORBs), etc.).

Example 3

Electrochemical Performance of Polynitroso Compound VII, TPA-3NO

Figure 23:
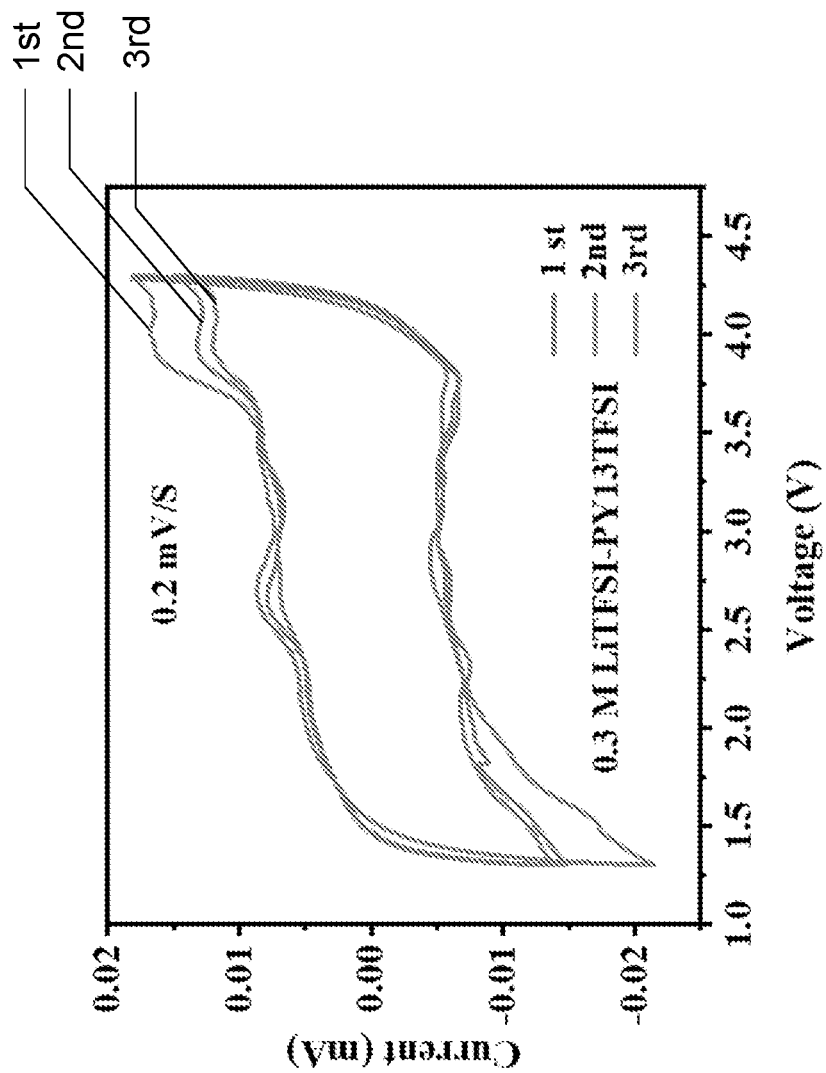
FIG. 23 is a cyclic voltammogram showing the cyclic voltammetry (CV) curves of TPA-3NO at 0.2 mV s$^{-1}$ in 0.3 M LiTFSI-PY13TFSI.

To investigate the electrochemical performance of TPA-3NO and its potential application as an energy storage material, TPA-3NO was assembled as a cathode for a LIBs with the electrolyte being 0.3 M LiTFSI-PY13TFSI (PY13TFSI=N-methyl-N-propylpyrrolidinium bis(trifluoromethanesulfonyl)amide). Cyclic voltammetry (CV) curves were recorded in the range of about 1.3-4.3 V (vs. Li/Li$^+$) at a scan rate of 0.2 mV s$^{-1}$ (FIG. 23). The results indicate that there are two oxidation peaks at about 2.6 V/3.8 V and two reduction peaks at about 2.4 V/3.7 V. Simultaneously, the CV curves show a slight change in the peak area while the basic peak shape remains intact, suggesting the complete reversibility of the lithium-ion insertion and extraction process.

Figure 24B:
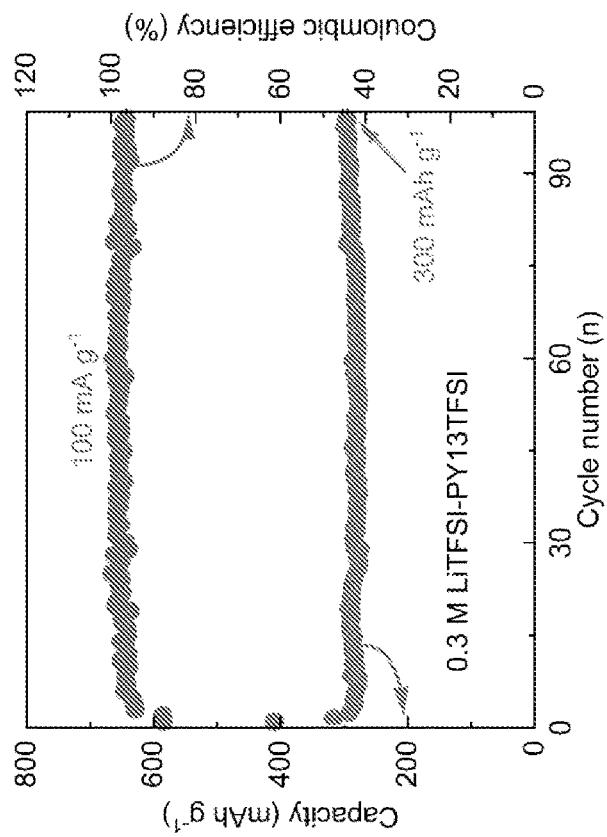
FIG. 24B is a plot showing the cycling performance of TPA-3NO in 0.3 M LiTFSI-PY13TFSI at 100 mA g$^{-1}$.
Figure 24A:
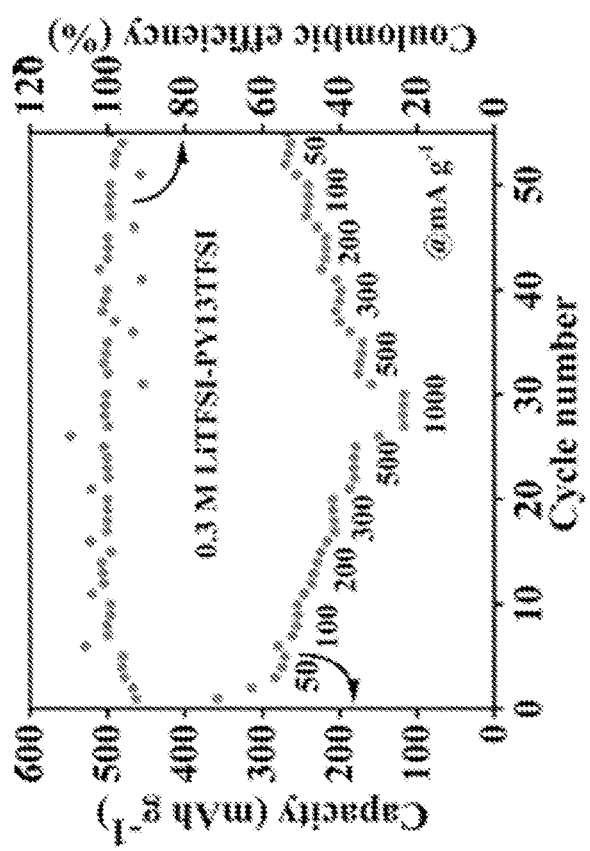
FIG. 24A is a plot of capacity against cycle number showing the rate performance of TPA-3NO in 0.3 M LiTFSI-PY13TFSI.
Figure 24C:
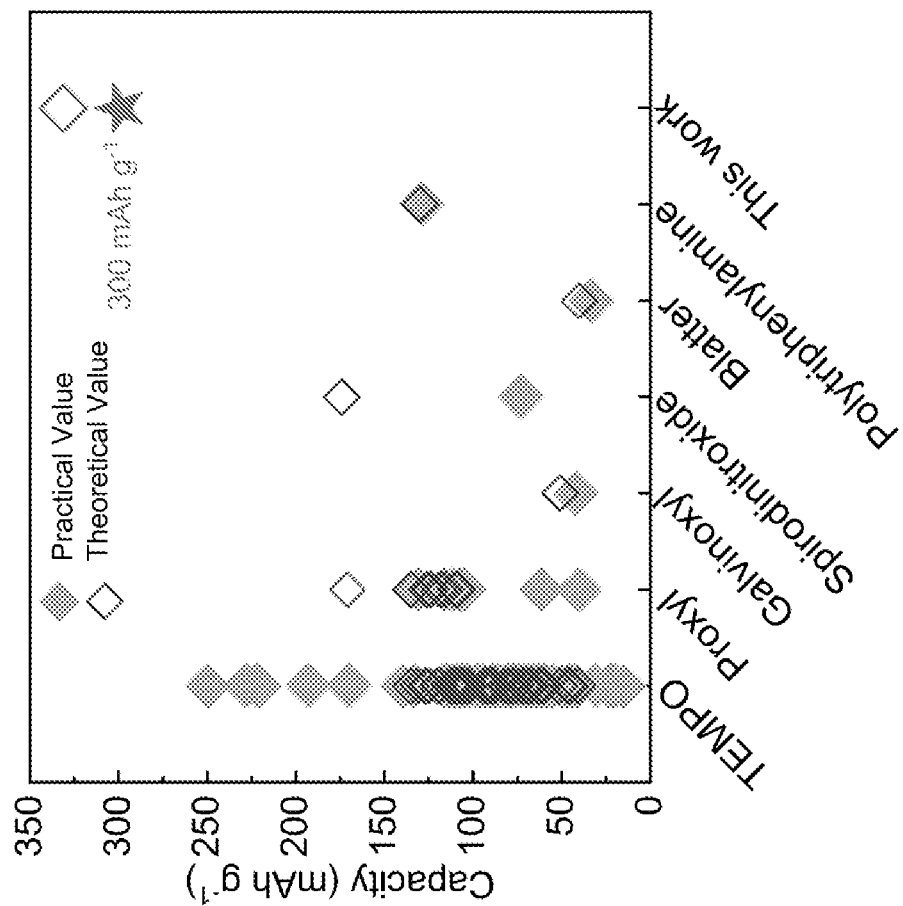
FIG. 24C is a plot illustrating the theoretical and practical capacities comparison of the organic radical cathode materials in LIBs.
Figure 25A:
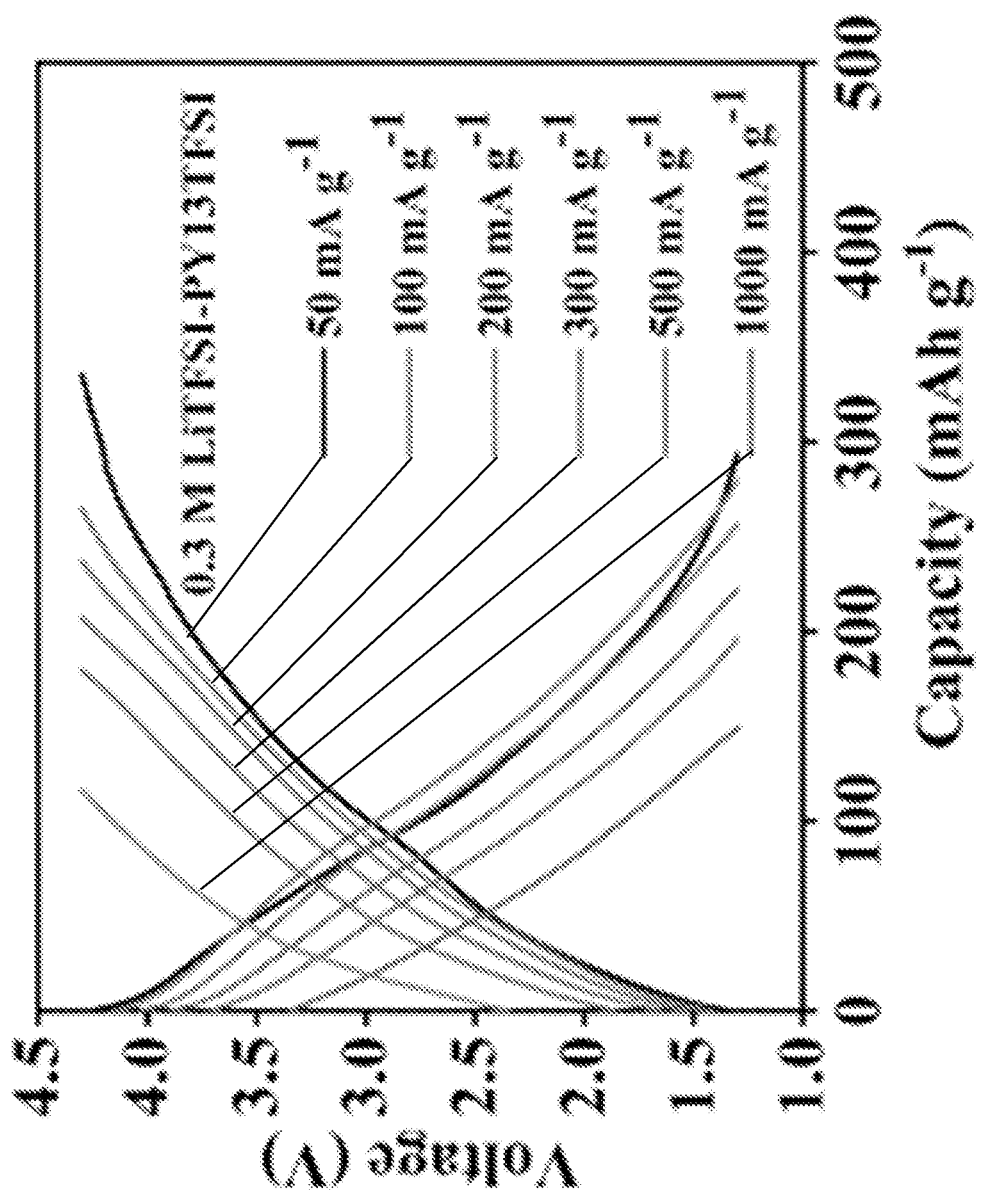
FIG. 25A is a plot of voltage against capacity showing the charging/discharging curves at different current densities of TPA-3NO in 0.3 M LiTFSI-PY13TFSI.
Figure 25B:
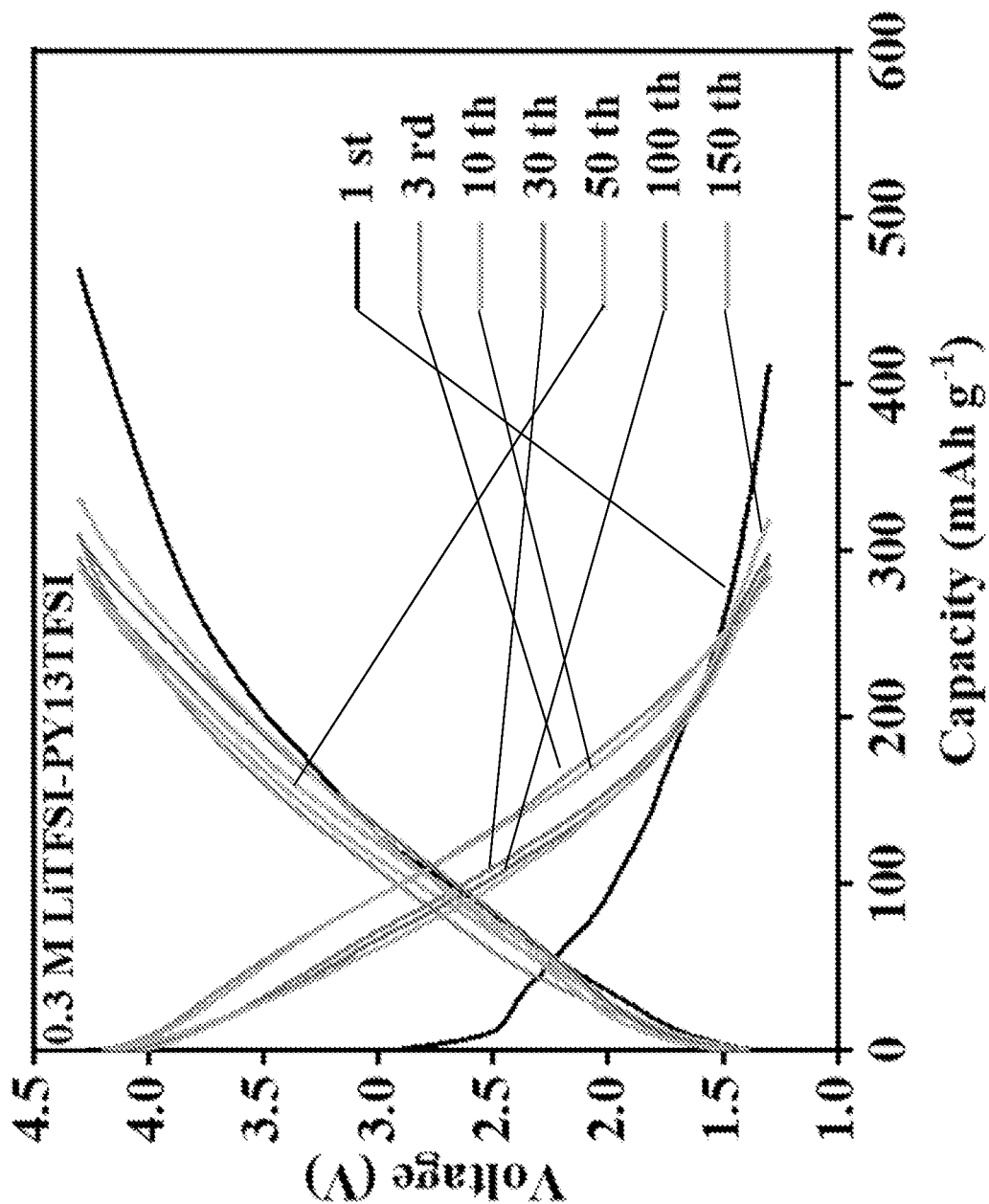
FIG. 25B is a plot of voltage against capacity showing the charging/discharging curves of TPA-3NO in 0.3 M LiTFSI-PY13TFSI at 100 mAg$^{-1}$ with respect to different cycle numbers.

The rate performances of TPA-3NO cathode were conducted at various current densities (FIG. 24A). The discharge capacity of TPA-3NO could be stabilized at nearly 270 mAh g$^{-1}$ with 96% recovery rate at 50 mA g$^{-1}$ after cycling under different current densities, revealing the remarkable reversibility of the material. Along with the increasing current density, the cathode still exhibits excellent capacities. For example, 181 and 117 mAh g$^{-1}$ capacities are achieved at 500 and 1000 mA g$^{-1}$, respectively, indicating its superior performance as a radical cathode material in LIBs. Furthermore, a specific capacity of 300 mAh g$^{-1}$ is maintained after 100 cycles at the current density of 100 mA g$^{-1}$ (FIG. 24B), which is much higher than those of reported radical materials (FIG. 24C). Besides, it can be intuitively seen from the charge-discharge curves (FIGS. 25A and 25B) that even the current density is raised to 1000 mA g$^{-1}$, it can still retain high capacity and stability in the wide voltage window of 1.3-4.3 V.

Figure 26A:
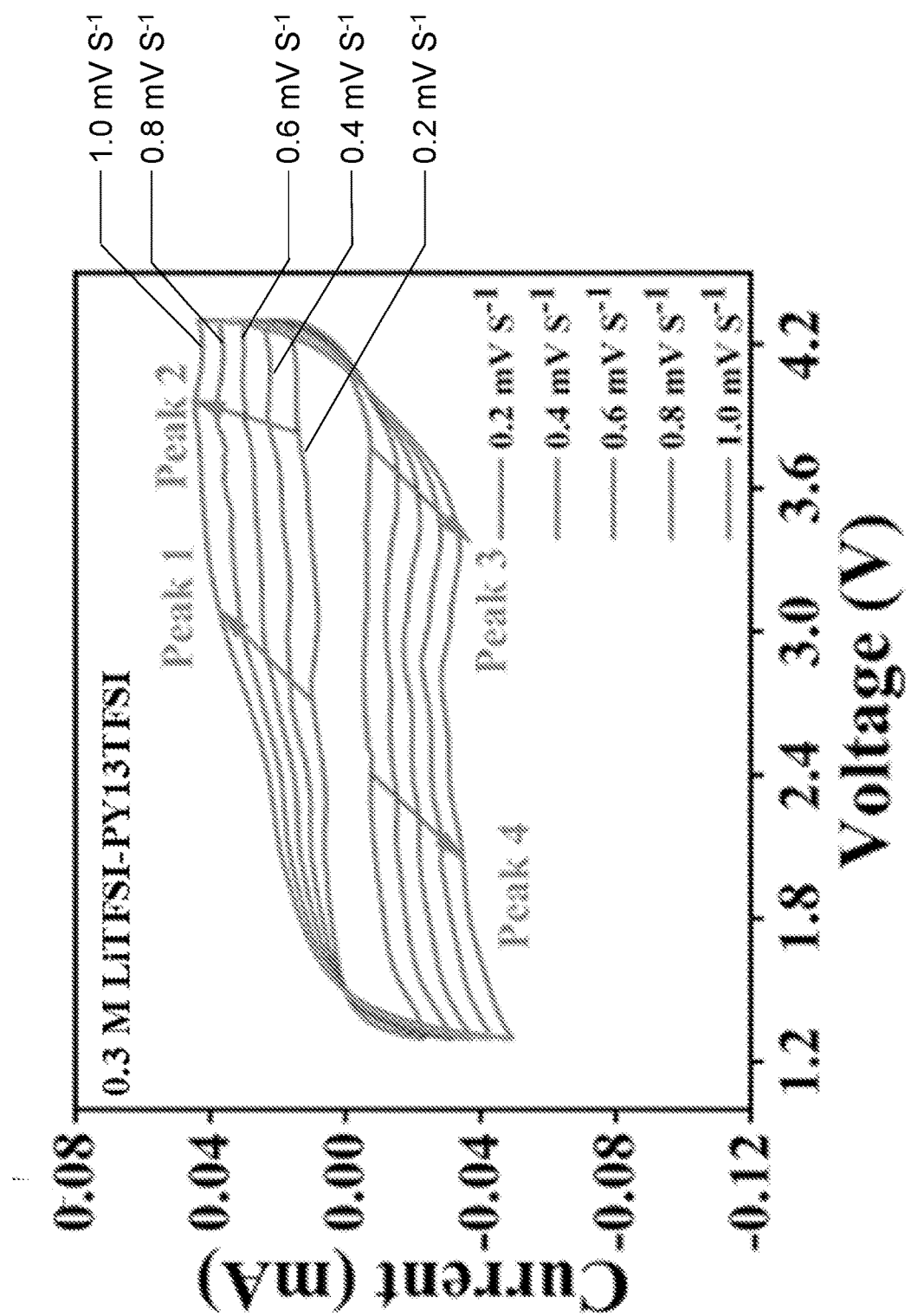
FIG. 26A is a cyclic voltammogram showing the CV curves of TPA-3NO in 0.3 M LiTFSI-PY13TFSI at different scan rates.
Figure 26B:
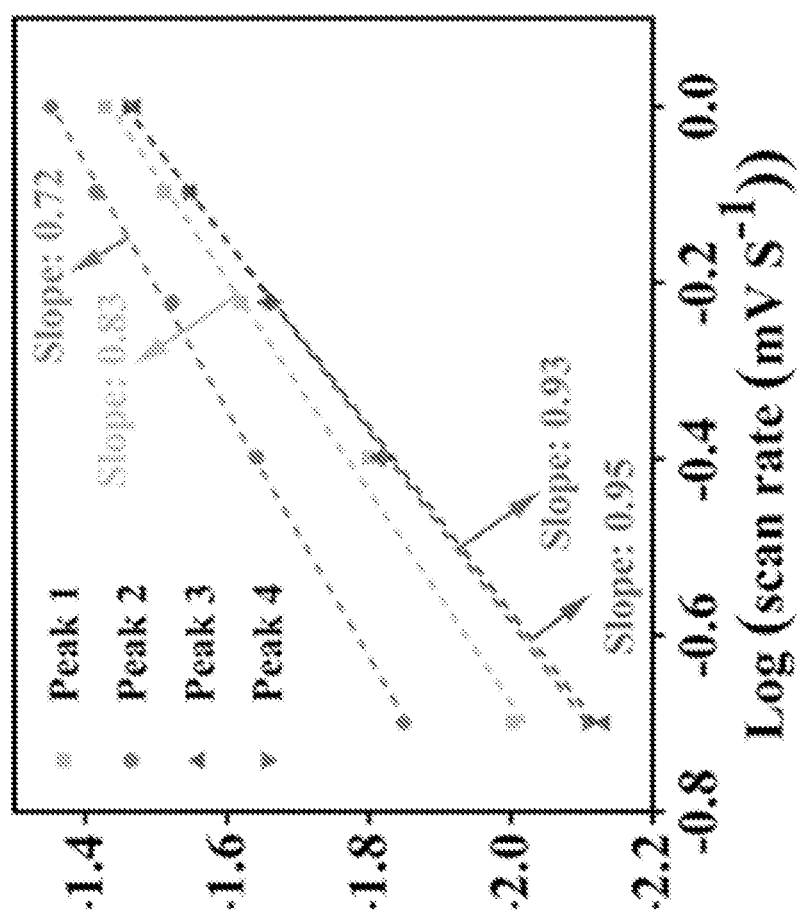
FIG. 26B is a plot showing the relationship between log i and log v.
Figure 26C:
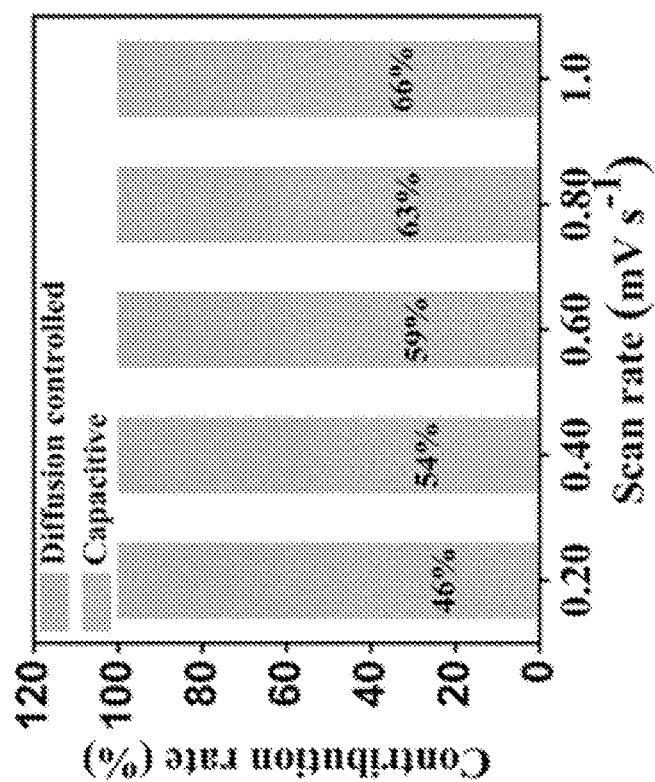
FIG. 26C is a bar chart showing the capacitive and diffusion-controlled capacity contribution at different scan rates of TPA-3NO in 0.3 M LiTFSI-PY13TFSI.

To understand the rate capability of the TPA-3NO electrode, a series of CV curves at different scan rates of 0.2, 0.4, 0.6, 0.8, and 1 mV s$^{-1}$ were recorded. It can be seen from FIG. 26A that with the increase in scanning rate, the altitude of the redox peak becomes distinct. On the contrary, their shapes are highly concordant, suggesting the negligible electrochemical polarization of the electrode. The kinetics process was explored to explain why the performance is outstanding. As illustrated in FIG. 26B, the small values of the slope rates (i.e., b is less than 1) unambiguously demonstrate that the charge storage is a fast surface-controlled pseudocapacitive process. Furthermore, the diffusion-controlled and capacitive contributions in the battery system can also be separately quantitatively analyzed (FIG. 26C). The capacitive contribution is determined to be 46% at a scan rate of 0.2 mV s$^{-1}$, which further increases to 66% at a scan rate of 1.0 mV s$^{-1}$. The result is in accord with the analysis mentioned above. Unambiguously, the kinetically fast pseudocapacitive process endowed the superior rate performance of the resulting battery system.

Figure 26D:
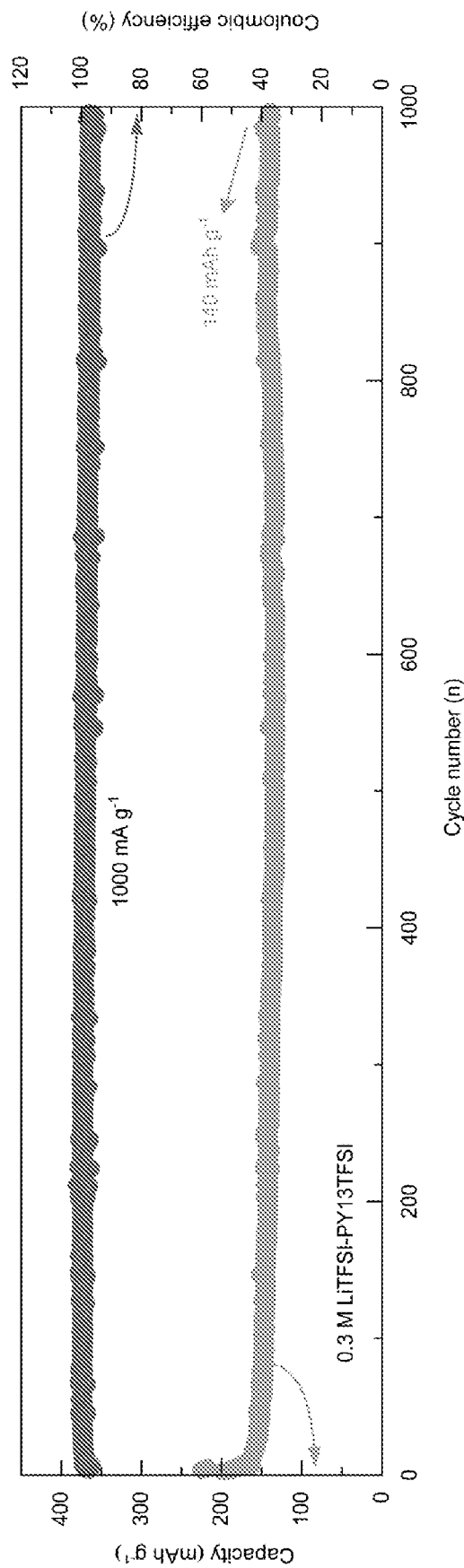
FIG. 26D is a plot illustrating the cycling performance of TPA-3NO in 0.3 M LiTFSI-PY13TFSI at 1 Ag$^{-1}$.
Figure 26E:
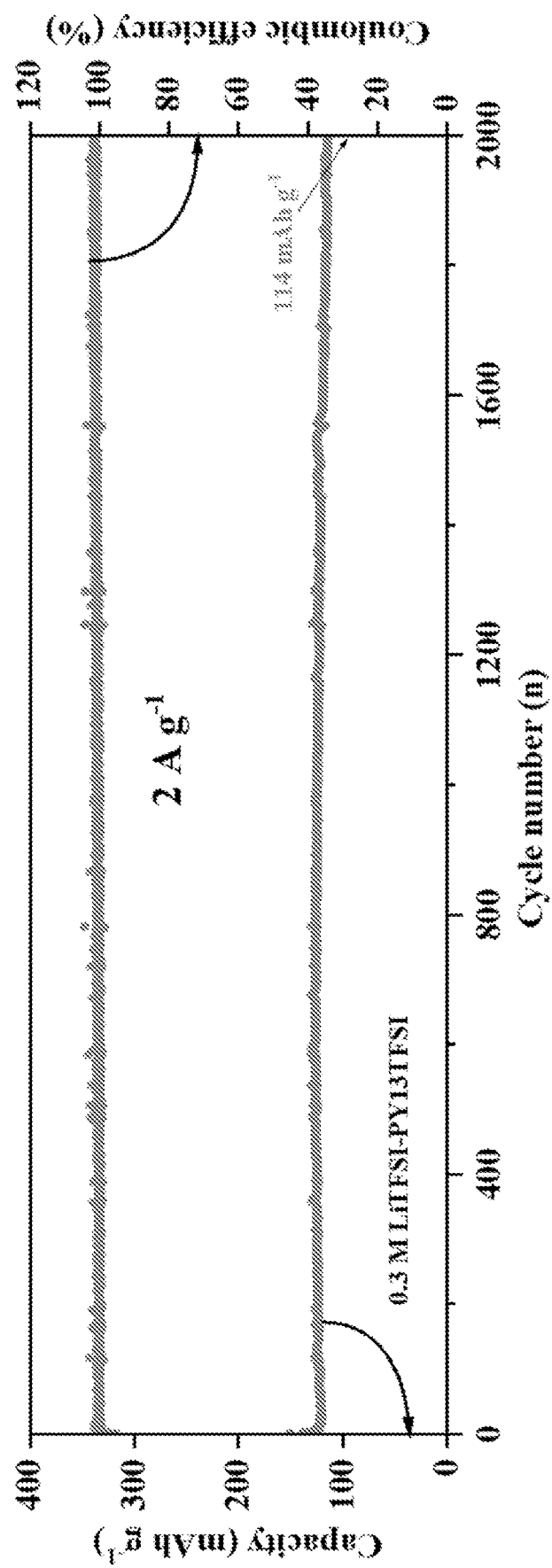
FIG. 26E is a plot showing the cycling performance of TPA-3NO in 0.3 M LiTFSI-PY13TFSI at 2 A g$^{-1}$.

In addition, the long cyclic performance of the TPA-3NO cathode was investigated. Notably, about 140 mAh g$^{-1}$ (85%) of capacity was retained after 1000 cycles at 1 A g$^{-1}$ (FIG. 26D), which surpasses most of the reported organic radical electrode materials (FIG. 24C). It is noteworthy that even at 2 A g$^{-1}$, after 2000 cycles, a capacity of about 114 mAh g$^{-1}$ was achieved (FIG. 26E). It is believed that such a wide voltage window (about 1.3-4.1 V) and a long cycling stability (>about 2000 cycles) are highly unexpected properties found in ORBs.

Figure 27:
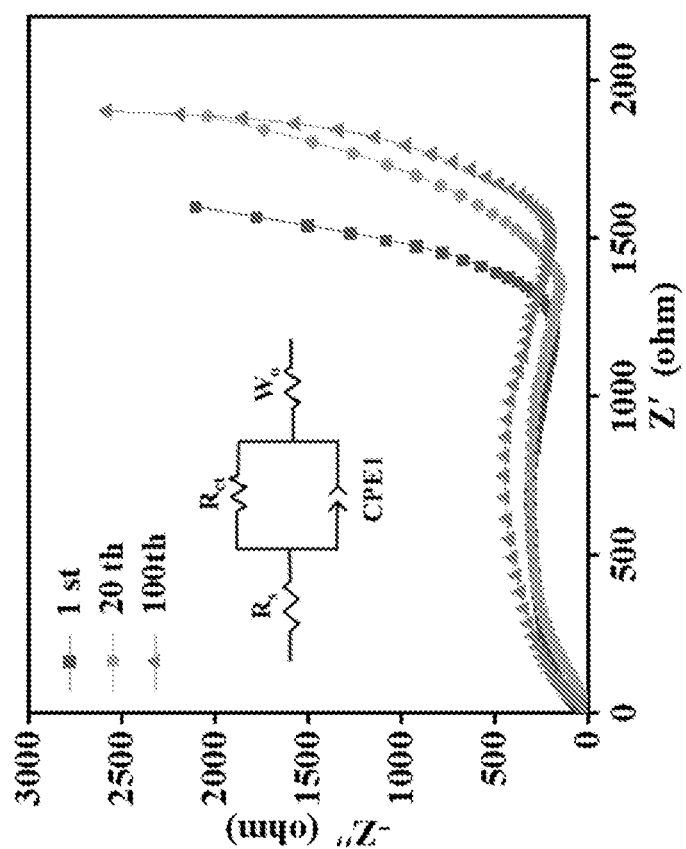
FIG. 27 is an electrochemical impedance spectrogram of TPA-3NO in 0.3 M LiTFSI-PY13TFSI.

Furthermore, the electrochemical impedance spectrogram (EIS) was performed at 10$^{-2}$ Hz to 10$^5$ Hz (FIG. 27). Although the impedance rises with the cycle, it eventually stabilizes. This trend is consistent with the cycling performance as discussed above, where the capacity initially decreases and ultimately tends to be stable.

Figure 28:
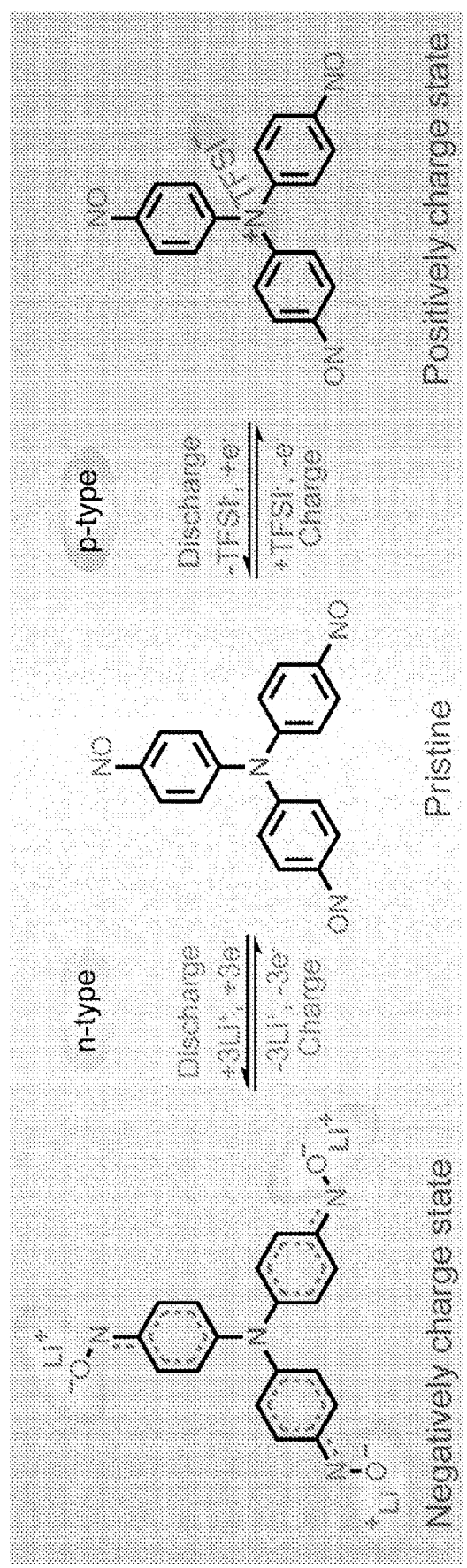
FIG. 28 is a schematic representation illustrating the proposed mechanism of charge and discharge process of TPA-3NO.

The charging and discharging mechanism of TPA-3NO was investigated. As shown in FIG. 28, the whole redox process can be divided into four stages. The n-type charge-discharge process involves the insertion and deintercalation of Li$^+$ towards TPA-3NO. And like other TPA-based redox-active organic electrode materials, the p-type charge-discharge process includes the combination and the separation between the central nitrogen atom on TPA and the TFSI$^-$ anion in the electrolyte. TPA-3NO is first reduced by accepting three electrons to form a wholly reduced state during the discharging. Accordingly, three N═O redox-active groups are converted into —N—O—Li with the insertion of three Li$^+$. Subsequently, TPA-3NO is oxidized by the loss of three electrons and recovers to its initial state during charging, which is accompanied by the deintercalation of three Li$^+$. In short, the first two stages are related to the oxidation-reduction process of the n-type doping reaction of the N═O group. Subsequently, the last two processes are attributed to the p-type doping of C—N moiety. When employed as the cathode material for lithium-ion batteries, the redox-active groups of central C—N and the peripheral N═O work together to provide a theoretical capacity as high as 323 mAh g$^{-1}$.

Figure 29B:
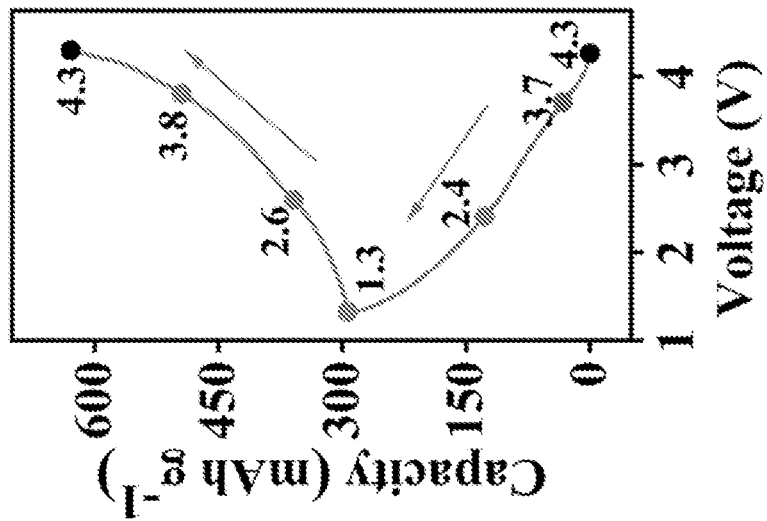
FIG. 29B is a plot of capacity against voltage corresponding to FIG. 29A.
Figure 29A:
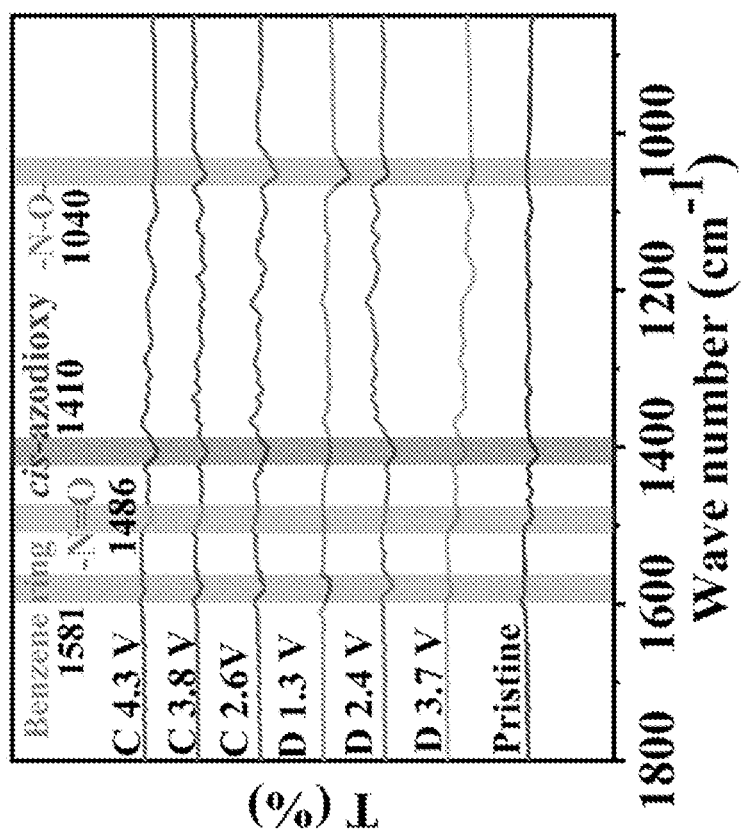
FIG. 29A is an ex-situ FTIR spectra of TPA-3NO during the charge and discharge processes.

The proposed redox mechanism was further exclusively verified by ex-situ FT-IR and X-ray photoelectron spectroscopy (XPS). During the discharge process, as the Li⁺ intercalated into N=O group to form =N—O—Li, the peak of nitroso groups at 1486 cm⁻¹ in the FT-IR spectrum was progressively weakened (FIGS. 29A and 29B). Simultaneously, the peak corresponding to =N—O—Li bond at 1040 cm⁻¹ emerged and strengthened gradually. However, in the charging process, Li⁺ leaves the N—O—Li unit, and the N—O—Li bond gradually disappears, along with the recurrence of the N=O bond. Besides, a similar change was also observed near the stretching of the benzene ring bond (1581 cm⁻¹) during the interaction of N=O groups with Li⁺. In addition, it is worth noting that the peak change at 1410 cm¹ belongs to cis-azodioxy bond because the reversible dimerization of nitroso group was also concomitantly occurred, which is the common phenomenon in nitroso derivatives. It is believed that these results have proven that N=O is the reversible redox active center during the charge and discharge process.

Furthermore, it is believed that that ex-situ XPS results have solidified the proposed mechanism and the obtained results. As shown in FIGS. 30A to 30E, when the battery discharged from pristine to 1.3 V, a new C peak appears at about 286.7 eV, revealing the state change of the benzene ring. After charging to 4.3 V, the peak was weakened and gradually returned to its original state. At the same time, by observing N is (FIG. 30B), a new n peak appears at about 398.6 eV, implying the interaction between TFSI⁻ anion and the central N atom, thus forming TFSI—TPA-3NO structure. However, when the discharge reaches 1.3 V, this peak also disappears. The peak changes of F is (FIG. 30D, about 285.2 eV) and S 2p (FIG. 30E, about 169.8 eV) further proved the insertion and deintercalation of TFSI⁻ anion directly. Therefore, N Is, F is and S 2p all proved the insertion and detachment of TFSI⁻ anion in the process of charge and discharge and revealed the characteristics of TPA-3NO as a p-type material.

Figure 30B:
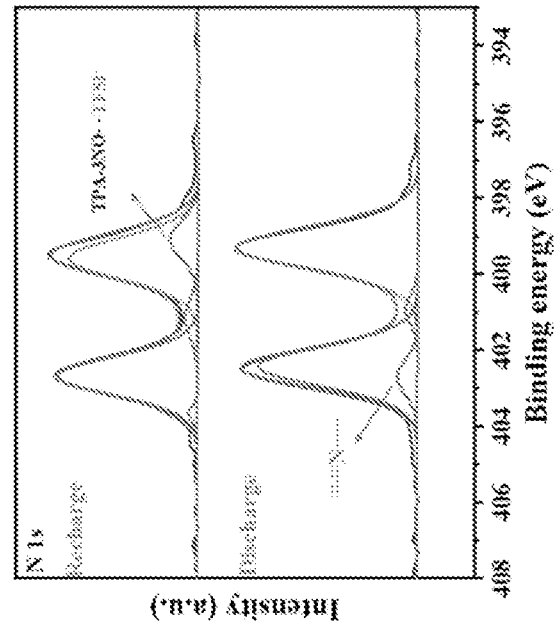
FIG. 30B is the ex-situ XPS spectra of N1s of TPA-3NO at recharged/discharged states.
Figure 30A:
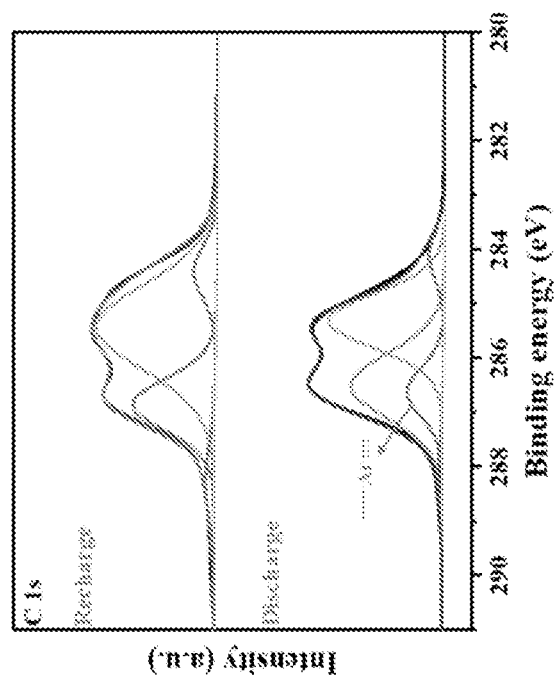
FIG. 30A is the ex-situ XPS spectra of C 1s of TPA-3NO at recharged/discharged states.
Figure 30D:
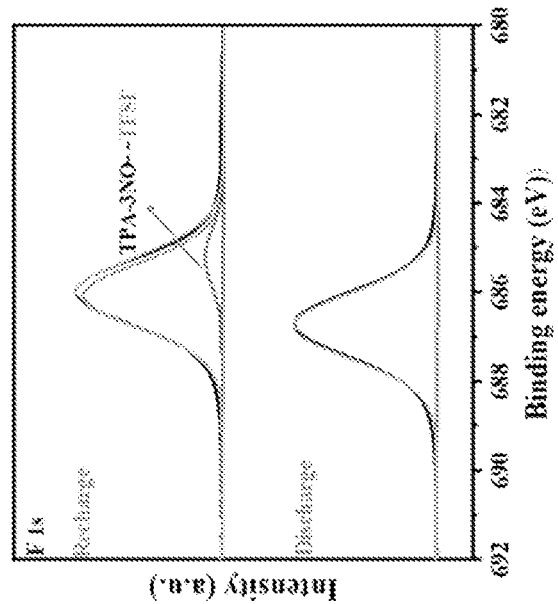
FIG. 30D is the ex-situ XPS spectra of F is of TPA-3NO at recharged/discharged states.
Figure 30C:
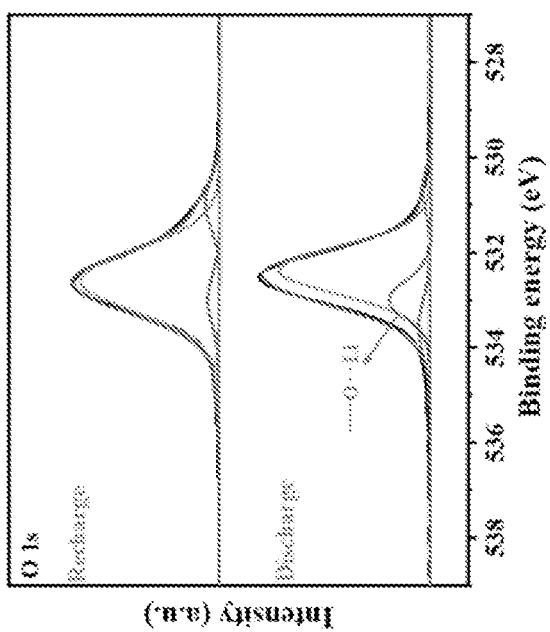
FIG. 30C is the ex-situ XPS spectra of O 1s of TPA-3NO at recharged/discharged states.
Figure 30E:
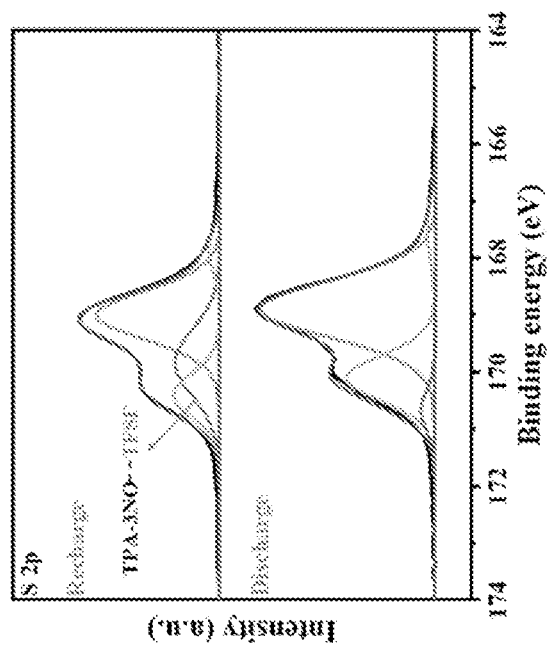
FIG. 30E is the ex-situ XPS spectra of S 2p of TPA-3NO at recharged/discharged states.

In another aspect, a new N peak at about 402.7 eV appeared when discharged to 1.3 V (FIG. 30B), which can be attributed to the formation of C=N—O— during the lithiation. The peak gradually disappeared after charging to 4.3 V. In addition, a similar variation was observed in O is spectrum (FIG. 30C). It can be seen that with the discharge to about 1.3 V, a new O peak appears at about 532.2 eV, and subsequently disappears, which can be assigned to the formation of the N—O—Li bond, thus proving the success of the reversible intercalation and deintercalation of Li⁺ towards the N=O bond. Therefore, the n-type characteristics of TPA-3NO were also verified by the N is and O is spectra changes. Based on these results, it is believed that the proposed charge/discharge mechanism of TPA-3NO in LIBs has been affirmed.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

All references specifically cited herein are hereby incorporated by reference in their entireties. However, the citation or incorporation of such a reference is not necessarily an admission as to its appropriateness, citability, and/or availability as prior art to/against the present invention.

What is claimed is:

1. A polynitroso compound, wherein the compound comprises a structure having a formula of:

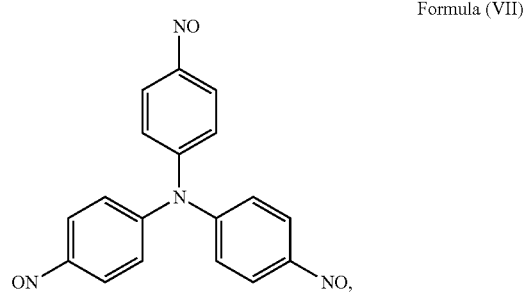

Formula (VII)

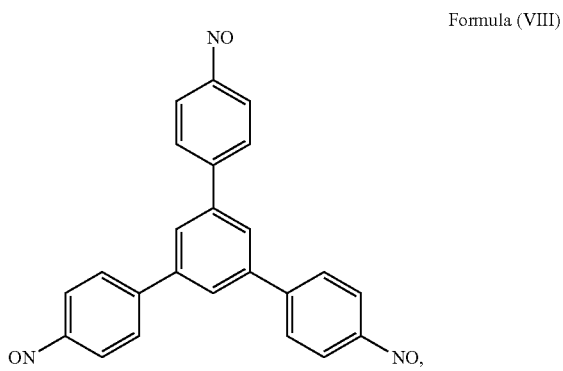

Formula (VIII)

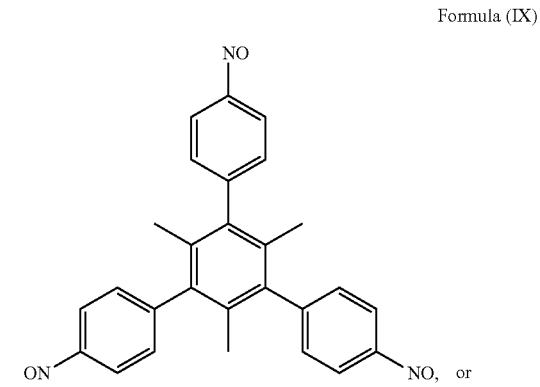

Formula (IX)

or

Formula (X)

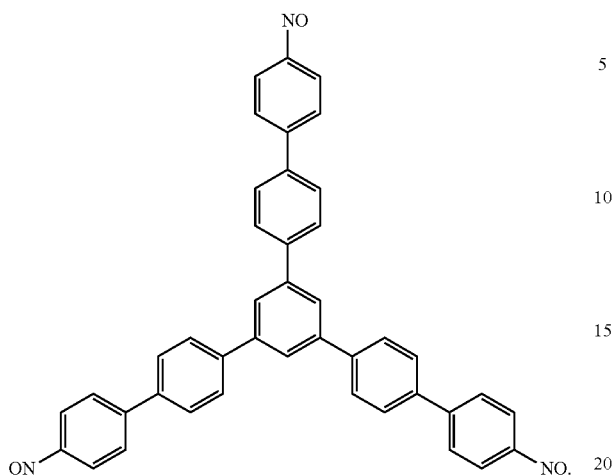

2. An energy storage device with a cathode comprising the polynitrosocompound as claimed in claim 1.

3. The energy storage device as claimed in claim 2, wherein the device is a rechargeable lithium-ion battery.

4. The energy storage device as claimed in claim 2, wherein the device has a stabilized discharge capacity from about 270 mA h g$^{-1}$ to about 117 mA h g$^{-1}$ at a current density from about 50 mA g$^{-1}$ to about 1 A g$^{-1}$ over a voltage window of about 1.3 V to about 4.3 V.

5. The energy storage device as claimed in claim 2, wherein the device has a specific capacity of about 300 mA h g$^{-1}$ after 100 charge/discharge cycles under a current density of about 100 mA g$^{-1}$.

6. The energy storage device as claimed in claim 2, wherein the device has about 85% capacity retention after about 1000 charge/discharge cycles under a current density of about 1 A g$^{-1}$.

7. A method for preparing the polynitroso compound as claimed in claim 1, comprising the steps of:
a) providing a precursor compound comprising two or more terminal trifluoroborate groups or silyl groups; and
b) conducting nitrosation to the precursor compound with a nitrosating agent wherein the precursor compound is selected from the group consisting of:

Formula (B1)

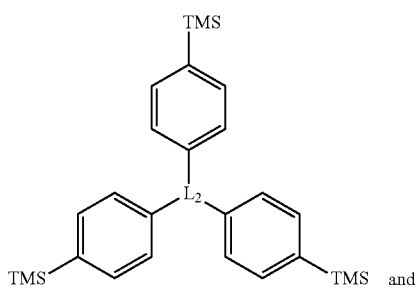

Formula (B2)

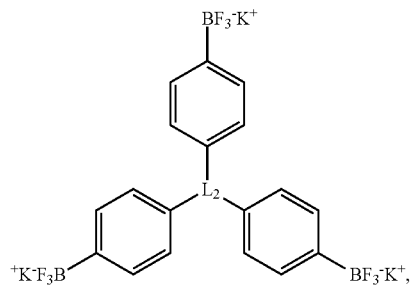

wherein L$_2$ is a nitrogen atom or

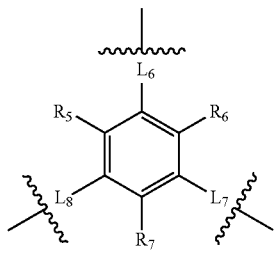

where R$_5$, R$_6$, and R$_7$ are either all hydrogen or all methyl when L$_6$, L$_7$, and L$_8$ are all absent or R$_5$, R$_6$, and R$_7$ are all hydrogen when L$_6$, L$_7$, and L$_8$ are all 1,4-phenylene.

8. The method as claimed in claim 7, wherein the nitrosating agent comprises a nitrosonium salt.

9. The method as claimed in claim 8, wherein the nitrosonium salt is selected from the group consisting of nitrosyl bromide, nitrosyl chloride, nitrosylsulfuric acid, posattium nitrite, sodium nitrite, silver nitrite, nitrosonium tetrafluoroborate, and a combination thereof.

10. The method as claimed in claim 7, wherein the nitrosation is conducted under a neutral or acidic condition.

11. The method as claimed in claim 10, wherein the acidic condition is adjusted by hydrochloric acid, hydrobromic acid, sulfuric acid or a combination thereof.

12. The method as claimed in claim 7, wherein the precursor compound is provided in form of a reaction solvent mixture.

13. The method as claimed in claim 12, wherein the reaction solvent is selected from the group consisting of 1,2-dichlorobenzene, dichloromethane, 1,2-dichloroethane, tetrahydrofuran, n-hexane, heptane, ethyl acetate, toluene, acetonitrile and a combination thereof.

14. The method as claimed in claim 13, wherein the reaction solvent is acetonitrile.

15. The method as claimed in claim 7, wherein step b) comprises the step of preparing a reaction mixture of the precursor compound and the nitrosating agent at a mole ratio of A:B, where A is from about 2 to about 4, and B is from about 3 to about 10.

16. The method as claimed in claim 9, wherein the nitrosonium salt is nitrosonium tetrafluoroborate.

* * * * *